US011684475B2

(12) United States Patent
Bishop et al.

(10) Patent No.: US 11,684,475 B2
(45) Date of Patent: *Jun. 27, 2023

(54) METHOD AND APPARATUS FOR TRANSVASCULAR IMPLANTATION OF NEO CHORDAE TENDINAE

(71) Applicant: Pipeline Medical Technologies, Inc., Santa Rosa, CA (US)

(72) Inventors: Gordon B. Bishop, Santa Rosa, CA (US); Randall T. Lashinski, Windsor, CA (US)

(73) Assignee: Pipeline Medical Technologies, Inc., Santa Rosa, CA (US)

( * ) Notice: Subject to any disclaimer, the term of this patent is extended or adjusted under 35 U.S.C. 154(b) by 502 days.

This patent is subject to a terminal disclaimer.

(21) Appl. No.: 16/881,935

(22) Filed: May 22, 2020

(65) Prior Publication Data

US 2020/0345496 A1 Nov. 5, 2020

Related U.S. Application Data

(63) Continuation of application No. 15/808,158, filed on Nov. 9, 2017, now Pat. No. 10,667,910, which is a
(Continued)

(51) Int. Cl.
*A61F 2/24* (2006.01)
*A61B 17/08* (2006.01)
(Continued)

(52) U.S. Cl.
CPC ........ *A61F 2/2457* (2013.01); *A61B 17/0401* (2013.01); *A61B 17/08* (2013.01);
(Continued)

(58) Field of Classification Search
CPC ... A61B 17/08; A61B 17/0401; A61F 2/2457; A61F 2/2409; A61F 2/2466
See application file for complete search history.

(56) References Cited

U.S. PATENT DOCUMENTS

| 4,677,065 A | 6/1987 | Buchbjerg et al. |
| 5,329,923 A | 7/1994 | Lundquist |

(Continued)

FOREIGN PATENT DOCUMENTS

| CN | 101495049 | 7/2009 |
| CN | 101553190 | 10/2009 |

(Continued)

OTHER PUBLICATIONS

International Search Report and Written Opinion received in PCT Application No. PCT/US2019/065814, dated Apr. 1, 2020 in 14 pages.

(Continued)

*Primary Examiner* — Ashley L Fishback
(74) *Attorney, Agent, or Firm* — Knobbe, Martens, Olson & Bear, LLP

(57) ABSTRACT

Methods and devices for transvascular prosthetic chordae tendinea implantation are disclosed. A catheter is advanced into the left atrium, through the mitral valve, and into the left ventricle. A ventricular anchor is deployed from the catheter and into a wall of the left ventricle, leaving a ventricular suture attached to the ventricular anchor and extending proximally through the catheter. A leaflet anchor is deployed to secure a mitral valve leaflet to a leaflet suture, with the leaflet suture extending proximally through the catheter. The leaflet suture is secured to the ventricular suture to limit a range of travel of the leaflet in the direction of the left atrium. Also disclosed is an assembled in situ mitral valve leaflet restraint, having a neo papillary muscle and a neo chordae tendinea.

20 Claims, 49 Drawing Sheets

Related U.S. Application Data continuation of application No. 15/638,176, filed on Jun. 29, 2017, now Pat. No. 9,877,833.

(60) Provisional application No. 62/441,031, filed on Dec. 30, 2016.

(51) Int. Cl.

| | | |
|---|---|---|
| A61B 17/04 | (2006.01) | |
| A61B 18/02 | (2006.01) | |
| A61B 17/06 | (2006.01) | |
| A61B 17/00 | (2006.01) | |
| A61B 18/00 | (2006.01) | |
| A61B 17/3205 | (2006.01) | |

(52) U.S. Cl.
CPC .......... *A61F 2/2409* (2013.01); *A61F 2/2466* (2013.01); *A61B 17/0485* (2013.01); *A61B 17/0487* (2013.01); *A61B 17/32053* (2013.01); *A61B 2017/00309* (2013.01); *A61B 2017/00358* (2013.01); *A61B 2017/0406* (2013.01); *A61B 2017/0409* (2013.01); *A61B 2017/0414* (2013.01); *A61B 2017/0417* (2013.01); *A61B 2017/0419* (2013.01); *A61B 2017/0441* (2013.01); *A61B 2017/0464* (2013.01); *A61B 2017/0488* (2013.01); *A61B 2017/0496* (2013.01); *A61B 2017/06052* (2013.01); *A61B 2018/00369* (2013.01); *A61B 2018/0212* (2013.01); *A61F 2220/0016* (2013.01)

(56) References Cited

U.S. PATENT DOCUMENTS

| | | |
|---|---|---|
| 5,456,708 A | 10/1995 | Doan et al. |
| 5,674,217 A | 10/1997 | Wahlstrom et al. |
| 6,269,819 B1 | 8/2001 | Oz |
| 6,458,107 B1 | 10/2002 | Ockuly |
| 6,461,366 B1 | 10/2002 | Seguin |
| 6,569,105 B1 | 5/2003 | Kortenbach et al. |
| 6,626,930 B1 | 9/2003 | Allen et al. |
| 6,629,534 B1 | 10/2003 | St. Goar et al. |
| 6,743,239 B1 | 6/2004 | Kuehn et al. |
| 6,752,813 B2 | 6/2004 | Goldfarb et al. |
| 6,770,083 B2 | 8/2004 | Seguin |
| 6,840,246 B2 | 1/2005 | Downing |
| 6,978,176 B2 | 12/2005 | Lattouf |
| 7,048,754 B2 | 5/2006 | Martin et al. |
| 7,083,628 B2 | 8/2006 | Bachman |
| 7,191,545 B2 | 3/2007 | Yi |
| 7,226,467 B2 | 6/2007 | Lucatero et al. |
| 7,288,097 B2 | 10/2007 | Seguin |
| 7,464,712 B2 | 12/2008 | Oz et al. |
| 7,563,267 B2 | 7/2009 | Goldfarb et al. |
| 7,604,646 B2 | 10/2009 | Goldfarb et al. |
| 7,608,091 B2 | 10/2009 | Goldfarb et al. |
| 7,632,308 B2 | 12/2009 | Loulmet |
| 7,635,386 B1 | 12/2009 | Gammie |
| 7,637,903 B2 | 12/2009 | Lentz et al. |
| 7,655,015 B2 | 2/2010 | Goldfarb et al. |
| 7,666,204 B2 | 2/2010 | Thornton et al. |
| 7,682,369 B2 | 3/2010 | Seguin |
| 7,736,388 B2 | 6/2010 | Goldfarb et al. |
| 7,871,368 B2 | 1/2011 | Zollinger et al. |
| 7,871,433 B2 | 1/2011 | Lattouf |
| 7,887,552 B2 | 2/2011 | Bachman |
| 7,914,515 B2 | 3/2011 | Heideman et al. |
| 7,914,545 B2 | 3/2011 | Ek |
| 8,075,570 B2 | 12/2011 | Bolduc et al. |
| 8,100,923 B2 | 1/2012 | Paraschac et al. |
| 8,172,872 B2 | 5/2012 | Osypka |
| 8,241,304 B2 | 8/2012 | Bachman |
| 8,252,050 B2 | 8/2012 | Maisano et al. |
| 8,273,054 B2 | 9/2012 | St. Germain et al. |
| 8,303,622 B2 | 11/2012 | Alkhatib |
| 8,382,829 B1 | 2/2013 | Call et al. |
| 8,409,273 B2 | 4/2013 | Thornton et al. |
| 8,465,500 B2 | 6/2013 | Speziali |
| 8,475,472 B2 | 7/2013 | Bachman |
| 8,475,525 B2 | 7/2013 | Maisano et al. |
| 8,480,730 B2 | 7/2013 | Maurer et al. |
| 8,545,551 B2 | 10/2013 | Loulmet |
| 8,545,553 B2 | 10/2013 | Zipory et al. |
| 8,603,066 B2 | 12/2013 | Heidman et al. |
| 8,690,939 B2 | 4/2014 | Miller et al. |
| 8,718,794 B2 | 5/2014 | Helland |
| 8,740,940 B2 | 6/2014 | Maahs et al. |
| 8,778,016 B2 | 7/2014 | Janovsky et al. |
| 8,814,824 B2 | 8/2014 | Kauphusman et al. |
| 8,852,213 B2 | 10/2014 | Gammie et al. |
| 8,940,042 B2 | 1/2015 | Miller et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,594 B2 | 2/2015 | Maisano et al. |
| 8,961,596 B2 | 2/2015 | Maisano et al. |
| 9,011,520 B2 | 4/2015 | Miller et al. |
| 9,023,065 B2 | 5/2015 | Bolduc et al. |
| 9,050,187 B2 | 6/2015 | Sugimoto et al. |
| 9,131,939 B1 | 9/2015 | Call et al. |
| 9,180,007 B2 | 11/2015 | Reich et al. |
| 9,198,649 B2 | 12/2015 | Karapetian et al. |
| 9,241,702 B2 | 1/2016 | Maisano et al. |
| 9,259,218 B2 | 2/2016 | Robinson |
| 9,277,994 B2 | 3/2016 | Miller et al. |
| 9,307,980 B2 | 4/2016 | Gilmore et al. |
| 9,314,242 B2 | 4/2016 | Bachman |
| 9,474,606 B2 | 10/2016 | Zipory et al. |
| 9,492,264 B2 | 11/2016 | Fifer et al. |
| 9,572,667 B2 | 2/2017 | Solem |
| 9,636,205 B2 | 5/2017 | Lee et al. |
| 9,636,224 B2 | 5/2017 | Zipory et al. |
| 9,668,860 B2 | 6/2017 | Kudlik et al. |
| 9,681,864 B1 | 6/2017 | Gammie et al. |
| 9,681,964 B2 | 6/2017 | MacKenzie |
| 9,693,865 B2 | 7/2017 | Gilmore et al. |
| 9,724,195 B2 | 8/2017 | Goodwin et al. |
| 9,750,493 B2 | 9/2017 | Robinson et al. |
| 9,788,948 B2 | 10/2017 | Gilmore et al. |
| 9,801,720 B2 | 10/2017 | Gilmore et al. |
| 9,814,454 B2 | 11/2017 | Sugimoto et al. |
| 9,877,833 B1 | 1/2018 | Bishop et al. |
| 9,907,547 B2 | 3/2018 | Gilmore et al. |
| 9,907,681 B2 | 3/2018 | Tobis et al. |
| 10,022,114 B2 | 7/2018 | Gilmore et al. |
| 10,039,643 B2 | 8/2018 | Gilmore et al. |
| 10,039,644 B2 | 8/2018 | Navia et al. |
| 10,052,095 B2 | 8/2018 | Gilmore et al. |
| 10,058,323 B2 | 8/2018 | Maisano |
| 10,076,327 B2 | 9/2018 | Ellis et al. |
| 10,076,658 B2 | 9/2018 | Hastings et al. |
| 10,130,791 B2 | 11/2018 | Heideman et al. |
| 10,159,571 B2 | 12/2018 | de Canniere |
| 10,206,673 B2 | 2/2019 | Maisano et al. |
| 10,213,291 B2 | 2/2019 | Berra et al. |
| 10,231,727 B2 | 3/2019 | Sutherland et al. |
| 10,238,491 B2 | 3/2019 | Tobis |
| 10,285,686 B2 | 5/2019 | Gammie et al. |
| 10,543,090 B2 | 1/2020 | Griswold et al. |
| 10,548,733 B2 | 2/2020 | Purcell et al. |
| 10,595,994 B1 | 3/2020 | Christianson et al. |
| 10,617,523 B2 | 4/2020 | Purcell et al. |
| 10,624,743 B2 | 4/2020 | Keidar et al. |
| 10,660,753 B2 | 5/2020 | Pham et al. |
| 10,667,910 B2 | 6/2020 | Bishop et al. |
| 10,675,150 B2 | 6/2020 | Bishop et al. |
| 10,682,230 B2 | 6/2020 | Bishop et al. |
| 10,925,731 B2 | 2/2021 | Bishop et al. |
| 11,083,580 B2 | 8/2021 | Purcell et al. |
| 2003/0105519 A1 | 6/2003 | Fasol et al. |
| 2003/0120341 A1 | 6/2003 | Shennib et al. |
| 2003/0130598 A1 | 7/2003 | Manning et al. |

(56) References Cited

U.S. PATENT DOCUMENTS

| | | |
|---|---|---|
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0073216 A1 | 4/2004 | Lieberman |
| 2004/0097979 A1 | 5/2004 | Svanidze et al. |
| 2005/0119735 A1 | 6/2005 | Spence et al. |
| 2005/0177132 A1 | 8/2005 | Lentz et al. |
| 2005/0177180 A1 | 8/2005 | Kaganov et al. |
| 2005/0251210 A1 | 11/2005 | Westra et al. |
| 2007/0038230 A1 | 2/2007 | Stone et al. |
| 2007/0118151 A1 | 5/2007 | Davidson |
| 2007/0123979 A1 | 5/2007 | Perier et al. |
| 2007/0219565 A1 | 9/2007 | Saadat |
| 2008/0177281 A1 | 7/2008 | Weitzner et al. |
| 2008/0177304 A1 | 7/2008 | Westra et al. |
| 2008/0195126 A1 | 8/2008 | Solem |
| 2008/0228165 A1 | 9/2008 | Spence et al. |
| 2008/0228223 A1 | 9/2008 | Alkhatib |
| 2008/0288061 A1 | 11/2008 | Maurer et al. |
| 2008/0294188 A1 | 11/2008 | Appling et al. |
| 2009/0043153 A1 | 2/2009 | Zollinger et al. |
| 2009/0069847 A1 | 3/2009 | Hashiba et al. |
| 2009/0082828 A1 | 3/2009 | Ostroff |
| 2009/0088837 A1 | 4/2009 | Gillinov et al. |
| 2009/0287304 A1 | 11/2009 | Dahlgren et al. |
| 2009/0312790 A1 | 12/2009 | Forsberg et al. |
| 2010/0023118 A1 | 1/2010 | Medlock et al. |
| 2010/0161042 A1 | 6/2010 | Maisano et al. |
| 2010/0161043 A1 | 6/2010 | Maisano et al. |
| 2010/0249919 A1 | 9/2010 | Gillinov et al. |
| 2010/0280604 A1 | 11/2010 | Zipory et al. |
| 2011/0011917 A1 | 1/2011 | Loulmet |
| 2011/0022083 A1 | 1/2011 | DiMatteo et al. |
| 2011/0040326 A1 | 2/2011 | Wei |
| 2011/0060407 A1 | 3/2011 | Ketai et al. |
| 2011/0106245 A1 | 5/2011 | Miller et al. |
| 2011/0301698 A1 | 12/2011 | Miller et al. |
| 2012/0065464 A1 | 3/2012 | Ellis et al. |
| 2012/0095505 A1 | 4/2012 | Shluzas |
| 2012/0116418 A1 | 5/2012 | Belson et al. |
| 2012/0116489 A1 | 5/2012 | Khairkhahan et al. |
| 2012/0158021 A1 | 6/2012 | Morrill |
| 2012/0172915 A1 | 7/2012 | Fifer et al. |
| 2013/0035757 A1 | 2/2013 | Zentgraf et al. |
| 2013/0046380 A1 | 2/2013 | Maisano et al. |
| 2013/0096672 A1 | 4/2013 | Reich et al. |
| 2013/0190741 A1 | 7/2013 | Moll et al. |
| 2013/0197575 A1 | 8/2013 | Karapetian et al. |
| 2013/0197577 A1 | 8/2013 | Wolf et al. |
| 2013/0197578 A1 | 8/2013 | Gregoire et al. |
| 2013/0253639 A1 | 9/2013 | Alkhatib |
| 2014/0142687 A1 | 5/2014 | De Canniere et al. |
| 2014/0142689 A1 | 5/2014 | De Canniere et al. |
| 2014/0243877 A9 | 8/2014 | Lee et al. |
| 2014/0243963 A1 | 8/2014 | Sheps et al. |
| 2014/0350417 A1 | 11/2014 | Van Bladel et al. |
| 2015/0032127 A1 | 1/2015 | Gammie et al. |
| 2015/0119979 A1 | 4/2015 | Maisano et al. |
| 2015/0182255 A1 | 7/2015 | Shivkumar |
| 2015/0230919 A1 | 8/2015 | Chau et al. |
| 2015/0250590 A1 | 9/2015 | Gries et al. |
| 2015/0313620 A1 | 11/2015 | Suri |
| 2015/0342737 A1 | 12/2015 | Biancucci et al. |
| 2015/0359632 A1 | 12/2015 | Navia et al. |
| 2016/0058557 A1 | 3/2016 | Reich et al. |
| 2016/0143737 A1 | 5/2016 | Zentgraf et al. |
| 2016/0174964 A1 | 6/2016 | Tobis |
| 2016/0192925 A1 | 7/2016 | Bachman |
| 2016/0228117 A1 | 8/2016 | Borden |
| 2016/0240941 A1 | 8/2016 | Stavrianoudakis |
| 2016/0256269 A1 | 9/2016 | Cahalane et al. |
| 2016/0262741 A1 | 9/2016 | Gilmore et al. |
| 2016/0310701 A1 | 10/2016 | Pai |
| 2016/0354082 A1 | 12/2016 | Oz et al. |
| 2016/0367367 A1 | 12/2016 | Maisano et al. |
| 2017/0042658 A1 | 2/2017 | Lee et al. |
| 2017/0043120 A1 | 2/2017 | Heideman et al. |
| 2017/0079797 A1 | 3/2017 | Maisano et al. |
| 2017/0086975 A1 | 3/2017 | Gilmore et al. |
| 2017/0119368 A1 | 5/2017 | Solem |
| 2017/0135817 A1 | 5/2017 | Tylis et al. |
| 2017/0156719 A1 | 6/2017 | Tobis |
| 2017/0156861 A1 | 6/2017 | Longoria et al. |
| 2017/0202657 A1 | 7/2017 | Lee et al. |
| 2017/0202669 A1 | 7/2017 | Schaffner et al. |
| 2017/0252032 A1 | 9/2017 | Hiorth et al. |
| 2017/0258464 A1 | 9/2017 | Gammie et al. |
| 2017/0258588 A1 | 9/2017 | Zipory et al. |
| 2017/0258594 A1 | 9/2017 | Gilmore et al. |
| 2017/0273681 A1 | 9/2017 | Gilmore et al. |
| 2017/0304050 A1 | 10/2017 | Keidar et al. |
| 2017/0304051 A1 | 10/2017 | Tobis et al. |
| 2017/0340433 A1 | 11/2017 | Berra et al. |
| 2017/0340443 A1 | 11/2017 | Stearns et al. |
| 2018/0064535 A1 | 3/2018 | Gilmore et al. |
| 2018/0185150 A1 | 7/2018 | Bishop et al. |
| 2018/0185151 A1 | 7/2018 | Bishop et al. |
| 2018/0185153 A1 | 7/2018 | Bishop et al. |
| 2018/0185179 A1 | 7/2018 | Murphy et al. |
| 2018/0206992 A1 | 7/2018 | Brown |
| 2018/0221148 A1 | 8/2018 | Guidotti et al. |
| 2018/0249993 A1 | 9/2018 | Denti et al. |
| 2018/0289480 A1 | 10/2018 | D'ambra et al. |
| 2018/0303614 A1 | 10/2018 | Schaffner et al. |
| 2018/0311007 A1 | 11/2018 | Tyler, II et al. |
| 2018/0318079 A1 | 11/2018 | Patel et al. |
| 2018/0318083 A1 | 11/2018 | Bolling et al. |
| 2018/0344311 A1 | 12/2018 | Gilmore et al. |
| 2018/0353297 A1 | 12/2018 | Griffin |
| 2018/0360439 A1 | 12/2018 | Niland et al. |
| 2019/0000624 A1 | 1/2019 | Wilson et al. |
| 2019/0015205 A1 | 1/2019 | Rajagopal et al. |
| 2019/0069891 A1 | 3/2019 | Gilmore et al. |
| 2019/0083085 A1 | 3/2019 | Gilmore et al. |
| 2019/0105027 A1 | 4/2019 | Gilmore et al. |
| 2019/0117401 A1 | 4/2019 | Cortez, Jr. et al. |
| 2019/0151090 A1 | 5/2019 | Gross et al. |
| 2019/0175345 A1 | 6/2019 | Schaffner et al. |
| 2019/0175346 A1 | 6/2019 | Schaffner et al. |
| 2019/0183480 A1 | 6/2019 | Hiorth et al. |
| 2019/0183648 A1 | 6/2019 | Trapp et al. |
| 2019/0216599 A1 | 7/2019 | Alkhatib |
| 2019/0216601 A1 | 7/2019 | Purcell et al. |
| 2019/0240023 A1 | 8/2019 | Spence et al. |
| 2019/0314155 A1 | 10/2019 | Franklin et al. |
| 2019/0328526 A1 | 10/2019 | Purcell et al. |
| 2019/0328527 A1 | 10/2019 | Pham et al. |
| 2019/0328528 A1 | 10/2019 | Purcell et al. |
| 2019/0328529 A1 | 10/2019 | Griswold et al. |
| 2019/0328530 A1 | 10/2019 | McDaniel et al. |
| 2019/0365539 A1 | 12/2019 | Rabito et al. |
| 2019/0380699 A1 | 12/2019 | Bak-Boychuk et al. |
| 2020/0155798 A1 | 5/2020 | Yang et al. |
| 2020/0297489 A1 | 9/2020 | Bishop et al. |
| 2020/0330228 A1 | 10/2020 | Anderson et al. |
| 2020/0390554 A1 | 12/2020 | Pham et al. |
| 2021/0186699 A1 | 6/2021 | Bishop et al. |
| 2021/0213259 A1 | 7/2021 | Giasolli et al. |
| 2022/0338990 A1 | 10/2022 | Hammill et al. |
| 2022/0339437 A1 | 10/2022 | Sorajja |

FOREIGN PATENT DOCUMENTS

| | | |
|---|---|---|
| CN | 101184454 | 10/2010 |
| CN | 101902975 | 12/2010 |
| CN | 103491901 | 1/2014 |
| CN | 103635160 | 3/2014 |
| CN | 103813757 | 5/2014 |
| CN | 103889345 | 6/2014 |
| CN | 104000625 | 8/2014 |
| CN | 104582637 | 4/2015 |
| CN | 105555229 | 5/2016 |
| CN | 107569301 | 1/2018 |
| EP | 1400537 | 3/2004 |

(56) References Cited

FOREIGN PATENT DOCUMENTS

| | | |
|---|---|---|
| EP | 1 898 802 | 9/2015 |
| EP | 2 979 647 | 2/2016 |
| EP | 3562410 | 11/2019 |
| FR | 2889416 | 2/2007 |
| JP | 2009-500105 | 1/2009 |
| JP | 2014-523282 | 9/2014 |
| RU | 2219853 | 12/2003 |
| WO | WO 2007/061834 | 5/2007 |
| WO | WO 2007/100268 | 9/2007 |
| WO | WO 2008/005747 | 1/2008 |
| WO | WO 2010/128502 | 11/2010 |
| WO | WO 2012/040865 | 4/2012 |
| WO | WO 2013/179295 | 12/2013 |
| WO | WO 2014/134185 | 9/2014 |
| WO | WO 2017/066888 | 4/2017 |
| WO | WO 2017/066889 | 4/2017 |
| WO | WO 2017/066890 | 4/2017 |
| WO | WO 2017/117560 | 7/2017 |
| WO | WO 2018/035378 | 2/2018 |
| WO | WO 2018/126188 | 7/2018 |
| WO | WO 2018/148324 | 8/2018 |
| WO | WO 2018/148364 | 8/2018 |
| WO | WO 2018/160456 | 9/2018 |
| WO | WO 2018/227048 | 12/2018 |
| WO | WO 2019/013994 | 1/2019 |
| WO | WO 2019/074815 | 4/2019 |
| WO | WO 2019/177909 | 9/2019 |
| WO | WO 2019/195860 | 10/2019 |
| WO | WO 2019/231744 | 12/2019 |
| WO | WO 2019/236654 | 12/2019 |
| WO | WO 2020/106705 | 5/2020 |
| WO | WO 2020/109594 | 6/2020 |
| WO | WO 2020/109596 | 6/2020 |
| WO | WO 2020/109599 | 6/2020 |
| WO | WO 2020/123719 | 6/2020 |
| WO | WO 2020/219281 | 10/2020 |
| WO | WO 2020/256853 | 12/2020 |
| WO | WO 2021/257278 | 12/2021 |

OTHER PUBLICATIONS

Notice of Allowance in Chinese Application No. 201780084920.8, dated Jun. 20, 2022, with English translation, in 5 pages.
Shikata et al., "Repair of Congenitally Absent Chordae in a Tricuspid Valve Leaflet with Hypoplastic Papillary Muscle Using Artificial Chordae", J Card Surg, 25:737-739 (2010).
Carpentier, M.D., Alain, "Cardiac Valve Surgery—the 'French Correction'", The Journal of Thoracic and Cardiovascular Surgery, Sep. 1983, vol. 86, No. 3, pp. 323-337.
International Search Report and Written Opinion received in PCT Application No. PCT/US2016/069567, dated Mar. 23, 2017 in 13 pages.
International Search Report and Written Opinion received in PCT Application No. PCT/US2017/069046, dated Jun. 14, 2018 in 11 pages.
International Search Report and Written Opinion received in PCT Application No. PCT/US2019/021480, dated Jul. 15, 2019 in 16 pages.
Júnior, Francisco Gregori et al., "Surgical Repair of Chordae Tendineae Rupture After Degenerative Valvular Regurgitation Using Standardized Bovine Pericardium", Revista Brasileira de Cirurgia Cardiovascular, Jan. 2013, vol. 28, No. 1, pp. 36-46.
Kobayashi et al., "Ten Year Experience of Chordal Replacement with Expanded Polytetrafluoroethylene in Mitral Valve Repair", Circulation, American Heart Association, Nov. 7, 2000, pp. III-30-III-34.

METHOD AND APPARATUS FOR TRANSVASCULAR IMPLANTATION OF NEO CHORDAE TENDINAE

INCORPORATION BY REFERENCE TO ANY PRIORITY APPLICATIONS

This application is a continuation of U.S. application Ser. No. 15/808,158, filed Nov. 9, 2017, which is a continuation of U.S. application Ser. No. 15/638,176, filed Jun. 29, 2017, which claims priority to U.S. Provisional Application 62/441,031, filed on Dec. 30, 2016, the entirety of each of these applications are hereby incorporated by reference herein for all purposes. Any and all applications for which a foreign or domestic priority claim is identified in the Application Data Sheet as filed with the present application are hereby incorporated by reference under 37 CFR 1.57.

BACKGROUND

Field

The disclosure relates generally to mitral valve repair devices and techniques, and in particular, to transvascular methods and devices for chordae tendinae replacement to reduce mitral regurgitation.

Description of the Related Art

The heart includes four heart valves, which allow blood to pass through the four chambers of the heart in one direction. The four valves are the tricuspid, mitral, pulmonary and aortic valves. The four chambers are the right and left atria (upper chambers) and right and left ventricle (lower chambers).

The mitral valve is formed by two leaflets, which are known as the anterior leaflet and the posterior leaflet, which open and close in response to pressure placed on the leaflets by the pumping of the heart. There are several problems that can develop or occur with respect to the mitral valve. Such problems include mitral valve regurgitation (MR), in which the mitral valve leaflets do not close properly, which can cause leakage of the mitral valve. Severe mitral regurgitation can adversely affect cardiac function and compromise a patient's quality of life and life-span.

Several techniques have been developed, for correcting mitral valve regurgitation. These include heart transplant, valve replacement or repair, chordae tendinea shortening or replacement and mitral annular repair also known as annuloplasty, depending upon the stage and underlying etiology.

As it relates to chordae tendinea replacement or repair, certain surgical and trans apical approaches have been proposed. Despite those efforts, however, there remains a need for a transvascular approach for chordae tendinea replacement or repair, to reduce or eliminate MR.

BRIEF DESCRIPTION OF THE DRAWINGS

FIGS. 35I-1 through 35I-4 illustrate deployment of a T tag type leaflet anchor.

FIGS. 35J-1 through 35J-3 illustrate deployment of a radially expandable tissue anchor.

FIG. 36A is a picture of a looped papillary muscle in a configuration it is first captured in.

SUMMARY OF THE INVENTION

Figure 1:
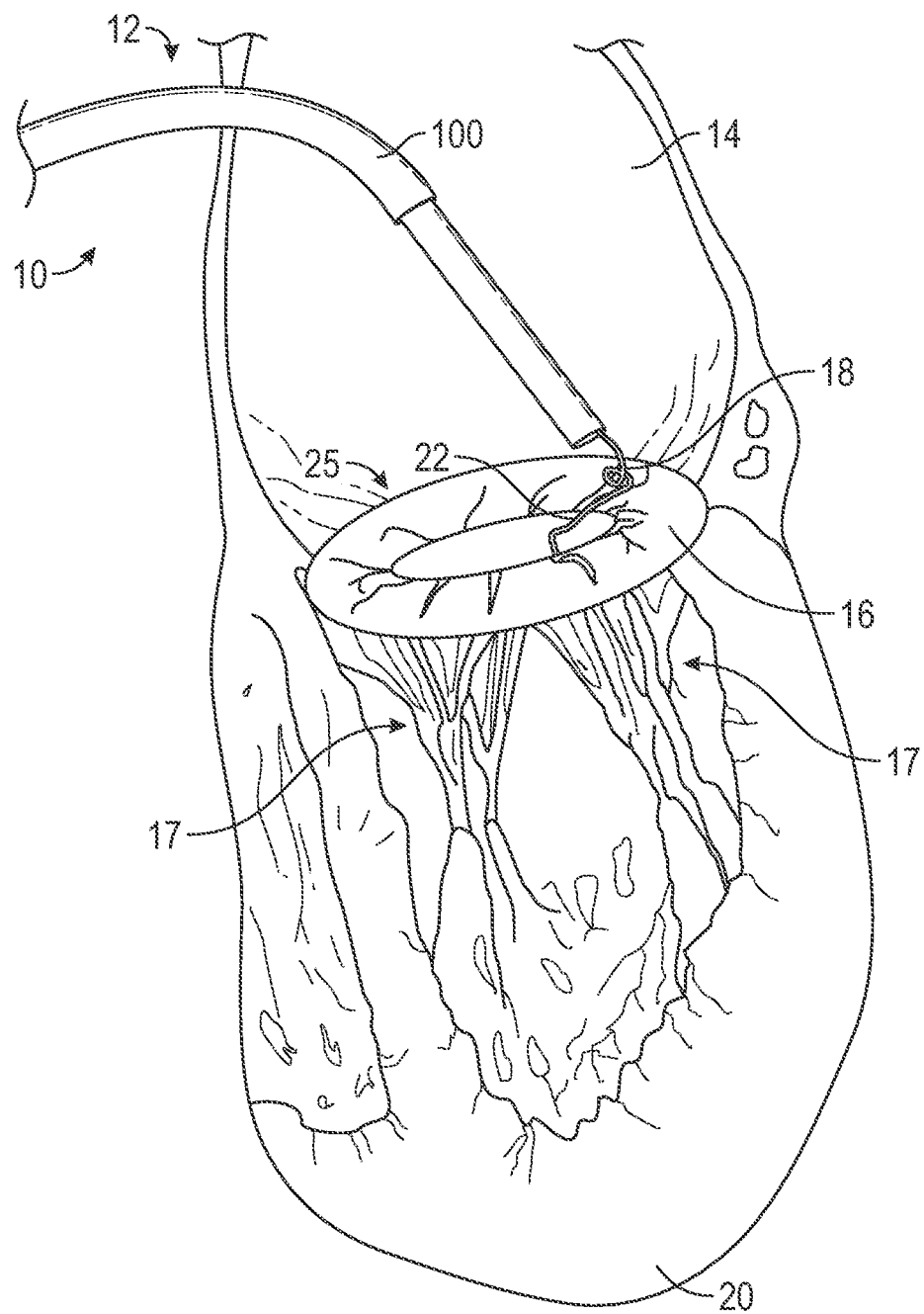
FIG. 1 illustrates the mitral valve annulus with a suture attached as delivered via catheter.

There is provided in accordance with one aspect of the present disclosure, a method of transvascular prosthetic chordae tendinea implantation. The method can comprise the steps of advancing a catheter into the left atrium, through the mitral valve, and into the left ventricle, and deploying a ventricular anchor from the catheter and into a wall of the left ventricle, leaving a ventricular suture attached to the ventricular anchor and extending proximally through the catheter. A leaflet anchor is deployed to secure a mitral valve leaflet to a leaflet suture, with the leaflet suture extending proximally through the catheter. The leaflet suture is secured to the ventricular suture to limit a range of travel of the leaflet in the direction of the left atrium.

The deploying a leaflet anchor step may comprise securing the leaflet anchor to the leaflet within the range of from about 3 mm to about 10 mm from a leaflet coaptive edge. The deploying a ventricular anchor step may comprise attaching the anchor to the ventricular septum or the ventricle wall, preferably spaced apart from the apex. The deploying a ventricular anchor step may comprise advancing an anchor driver through the mitral valve, rotating the driver to secure the ventricular anchor, and proximally retracting the anchor driver to expose the ventricular suture carried by the ventricular anchor.

The deploying a leaflet anchor step may comprise positioning a needle guide in contact with the leaflet and advancing a needle from the needle guide and through the leaflet. The method may further comprise deflecting a distal portion of the needle guide through an angle of at least about 160 degrees to position a distal end of the needle guide against the ventricle side of the leaflet. The needle guide may comprise a slotted tube and deflecting the needle guide may be accomplished by proximally retracting a pull wire.

The securing step may comprise applying a suture lock to the ventricular suture and the leaflet suture. The method may further comprise applying tension to the leaflet suture prior to the securing step, to improve leaflet function. The method may further comprise applying sufficient tension to the leaflet suture to pull the limit of leaflet travel during systole to approximately to the level of the annulus. The securing step may comprise engaging a knot to secure the leaflet suture and the ventricular suture. The method may additionally comprise the step of cutting the leaflet suture and the ventricular suture proximally of the suture lock or knot, leaving the leaflet suture and the ventricular suture to function as a native chordae.

The method may additionally comprise the initial step of identifying a patient including at least three characteristics selected from the group consisting of: the patient has been diagnosed with primary or degenerative mitral regurgitation; the patient has been diagnosed with secondary or functional Mitral Regurgitation; the patient has been diagnosed with Mixomotous Mitral Regurgitation; the patient has been diagnosed with a flail leaflet, ruptured chordae, or leaflet prolapse; the patient has Mitral regurgitation grade 1 or more; the patient has annular diameter from A2 leaflet to P2 leaflet at least 5 mm less than sum of length of P2+A2 leaflet; the patient has annular diameter from A2 to P2 leaflet of at least 10 mm; and the patient has an access vessel diameter of at least 2 mm.

The patient may additionally have at least one characteristic selected from the group consisting of: the patient has been evaluated by a heart team including at least one cardiac surgeon and determined not to be an appropriate candidate for conventional open surgical repair; the patient has STS predicted operative mortality (STS Score) of 2 or greater; the patient was offered and refused open surgical repair; the patient is age between 18 and 90; the patient will not accept blood transfusion; the patient has had prior open chest surgery; and the patient has an ejection fraction of at least 10 percent.

In accordance with a further aspect of the present disclosure, there is provided a method of increasing mitral valve leaflet coaptive area during systole. The method comprises the steps of securing at least a first ventricular tension element to a wall of the ventricle and securing at least a first leaflet tension element to a mitral valve leaflet. The leaflet tension element is proximally retracted to move the limit of travel of the leaflet during systole in the direction of the ventricle, thereby increasing mitral valve leaflet coaptive area during systole. The leaflet tension element is thereafter secured to the ventricular tension element.

The ventricular tension element may comprise a neo papillary muscle having a distal end facing the ventricular anchor, and a proximal end approximately at the height of the top of the native papillary muscle, and the securing step may comprise securing the leaflet tension element to the ventricular tension element at the proximal end of the neo papillary muscle. The neo papillary muscle may comprise an elongate, atraumatic body, and may comprise ePTFE.

The securing a leaflet tension element step may comprise advancing a needle guide having a distal end through the mitral valve and into the left ventricle, and deflecting the needle guide through an angle of at least 160 degrees to place the distal end into contact with the leaflet during diastole. The method may further comprise advancing a leaflet anchor deployment needle out of the distal end of the needle guide and through the leaflet, and deploying an anchor from the needle. The deploying an anchor step may comprise deploying an anchor from a first, reduced cross section within the deployment needle, to a second, enlarged cross section for seating against the atrial side of the leaflet. The deploying an anchor step may comprise deploying a pledget.

The proximally retracting the leaflet tension element step may comprise positioning an aperture in the left ventricle, with at least the leaflet tension element extending through the aperture, and proximally retracting the leaflet tension element with the aperture functioning as a fulcrum so that the tension element draws the leaflet in the direction of the ventricle. The fulcrum may comprise a distal opening of a catheter and the proximally retracting step may comprise proximally retracting the leaflet tension element through the catheter. The method may further comprise securing a second leaflet tension element to the leaflet and to the ventricular tension element.

In accordance with a further aspect of the present disclosure, there is provided an assembled in situ mitral valve leaflet restraint. The restraint comprises an elongate, flexible neo papillary muscle, having a proximal end and a distal end, and a helical tissue anchor attached to the distal end of the neo papillary muscle. An elongate, flexible neo chordae extends proximally from the neo papillary muscle, and a leaflet anchor is attached to a proximal end of the neo chordae. The leaflet anchor is enlargeable from a first reduced cross section for advancing through the leaflet, to a second, enlarged cross section for contacting an atrial side of the leaflet. The neo chordae may be attached to a suture extending distally through the neo papillary muscle to the helical tissue anchor.

DETAILED DESCRIPTION OF THE PREFERRED EMBODIMENTS

An embodiment to attach a ruptured or flail chord could include a catheter delivered through the femoral vein and traversed up into the IVC and trans-septal to the left atrium where an attachment is made to the mitral annulus. This attachment could be a single suture loop through the mitral annular tissue or an anchor inserted into the annulus either rotated, pierced into or threaded to the local tissue where the mitral leaflet meets the atrial tissue at or near the mitral annulus. The anchor could be constructed of a coiled-wire anchor which would be rotated into the tissue with a suture receiver for chordal replacement or a pre-attached chordal affixed to the anchor.

A connection to the mitral annulus can provide a secure and positive attachment point as a stable anchor through a piercing, hook or corkscrew anchoring device. To this attachment point a chord can be connected to drape over the mitral valve leaflet and further attached or anchor into the apex of the left ventricle. It could also be pierced through the anterior or posterior mitral leaflets at any position. The chord can be made of round, flat PTFE, PE or nylon as conventionally used in surgery for chordal repair.

Anchoring to the annulus can provide an attachment point which is positive and immobile with respect to the mitral leaflets which are difficult to capture with a ruptured chord due to the movement at each heartbeat. This movement can be halted with a grasping of the flail leaflet by a mechanical gripper tool, suction tube or a cryo-catheter to freeze-grab the leaflet. As the upper anchor is positively attached to the mitral annulus it can be draped over the mitral leaflet and between the existing chords to limit the location laterally with respect to the leaflet. Locating the leaflet between existing chords provides the artificial chord a positive anchor at the upper anchor point, a secured angular location passing through the existing chords and another positive location at the apex of the left ventricle. The replacement chord can be a single suture strand or a plurality of chords traversing up and down the pathway as described above allowing the load to be carried by a plurality of chords.

The lower apical anchor located in the left ventricle can be secured via rotational screw or plug to hold positively. The anchor could be short in height and close to the base of the apex or have an extended length to better match the native papillary muscles of about 20-22 millimeters above the apex of the left ventricle. A single or plurality chord could be attached to one or more anchors at the base of the left ventricle. The anchor could be constructed of an implantable grade of stainless steel, Nitinol or other metallic material that would be visible on fluoroscopy or a polymeric material such as PEEK, PTFE or other implantable materials. These polymers could be doped with a radiopaque marker for visibility if needed.

An embodiment for the anchoring system could comprise of the apical tissue anchor which couples or attaches to the left ventricle, a riser which projects the attachment from the apical tissue anchor and could be constructed from a monolithic material or a combination of materials including polymers and metallic components. The construction could be rigid throughout or have flexible joints to allow movement or an elastic zone or zones for controlled motion and flexibility. It could be constructed of a round crossing profile or any other profile including a varying shape longitudinally. The diameter could be about 6 to 24 French (2 to 8 millimeters) and length about 20 to 40 millimeters and delivered via steerable catheter with or without a guidewire generally along the central axis. Once the upper leaflet anchor is attached to the mitral annulus or leaflet and draped over the mitral leaflets and further coupled to the lower anchor a tension force would allow for an adjustment under live echo while monitoring the leaflet motions and regurigtent flow reduction. The final step could be to tension, lock and disconnect the chord from the delivery system. A tension of the chord would apply tension to the connected mitral valve leaflet strain relief and a locking device such as a Cor-Knot from LSI Solutions could be advanced down the chord and lastly the suture tail could be cut.

Figure 2:
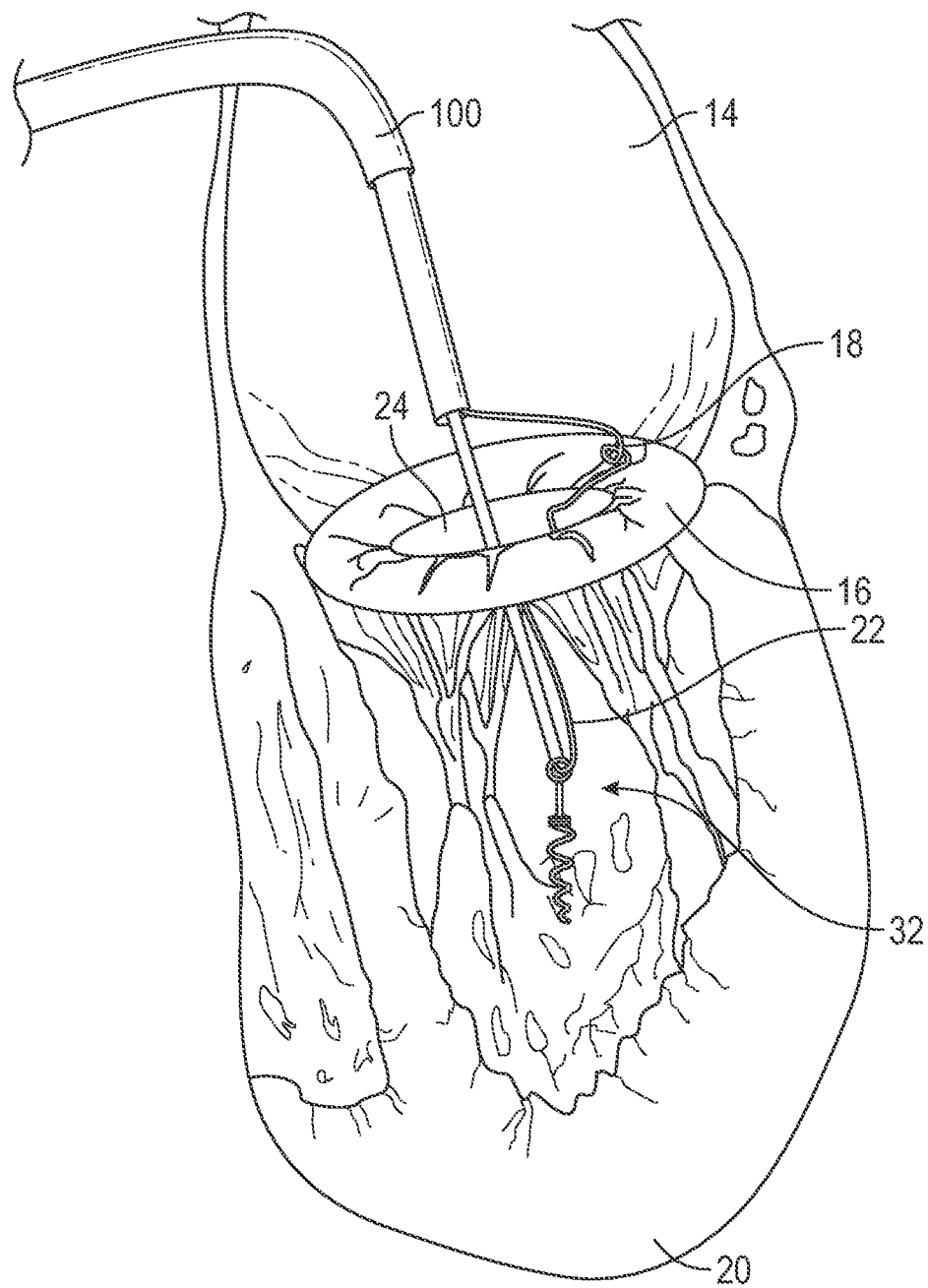
FIG. 2 illustrates the distal anchor being delivered via catheter and attached to a suture further connected to the mitral annulus.
Figure 3:
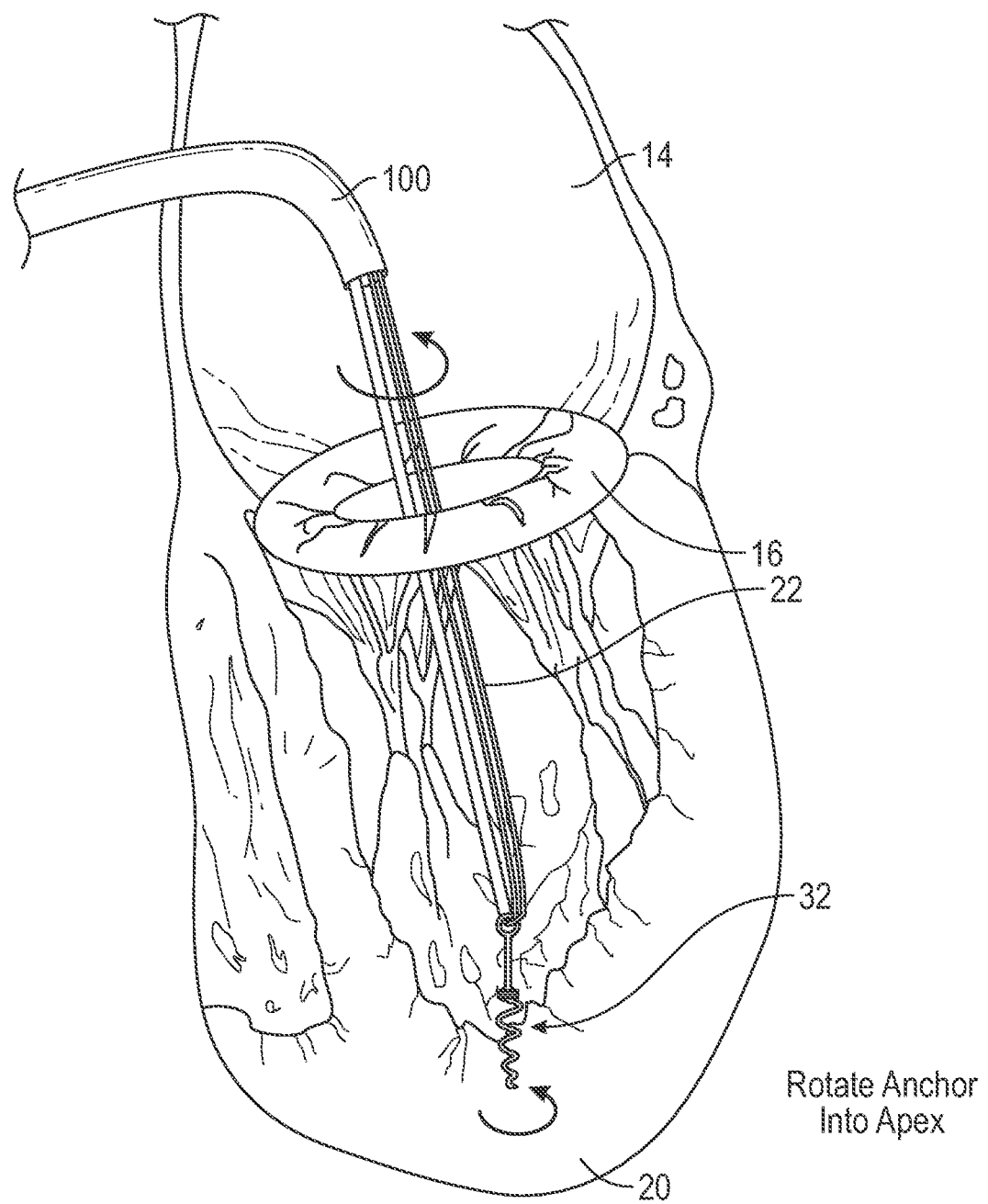
FIG. 3 illustrates the distal anchor being rotated into the apex of the heart with suture lines attached for later attachment to the mitral leaflet or the mitral annulus.
Figure 4:
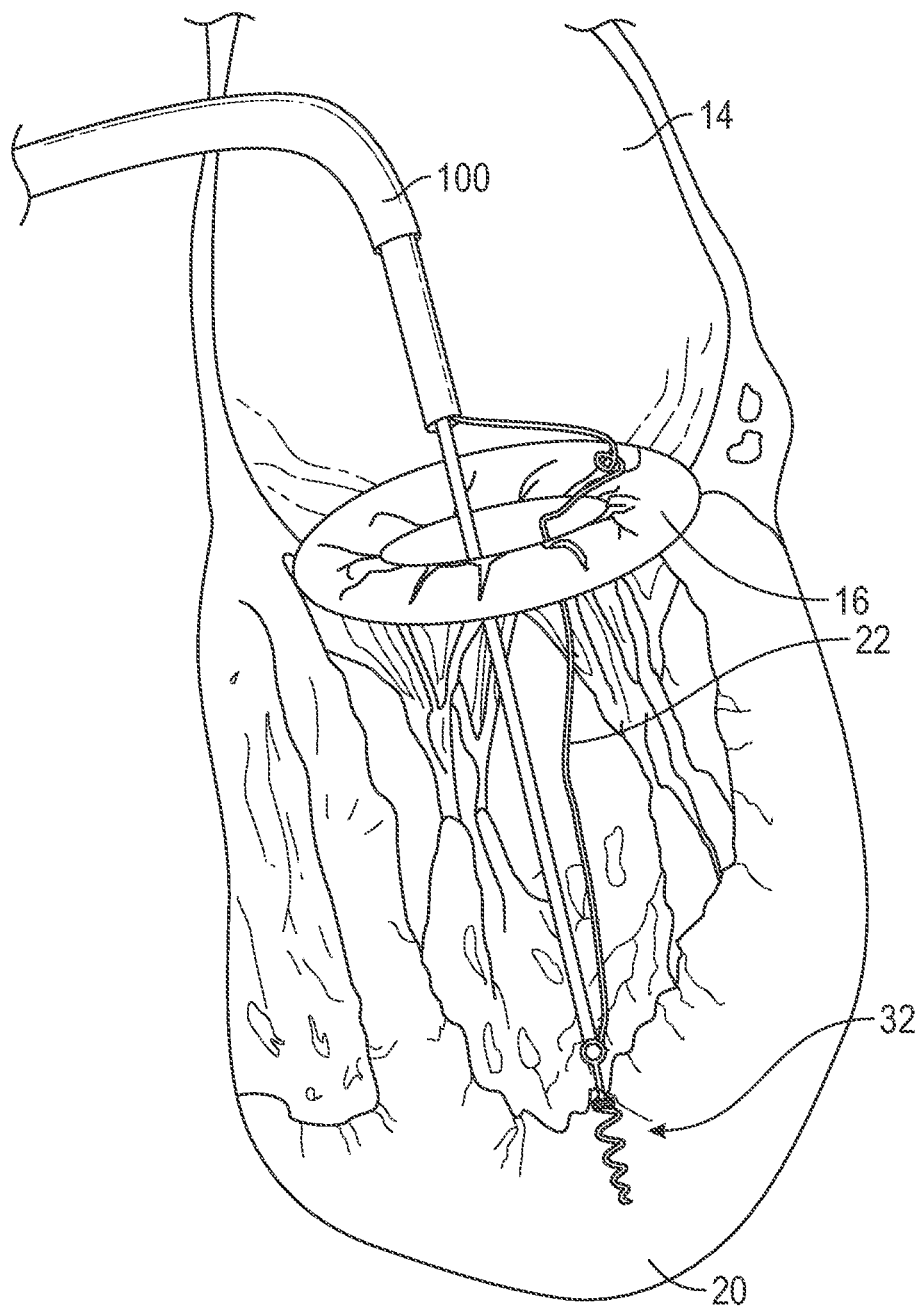
FIG. 4 illustrates the distal anchor rotated into the apex of the heart with suture lines attached to the mitral leaflet or the mitral annulus.
Figure 5:
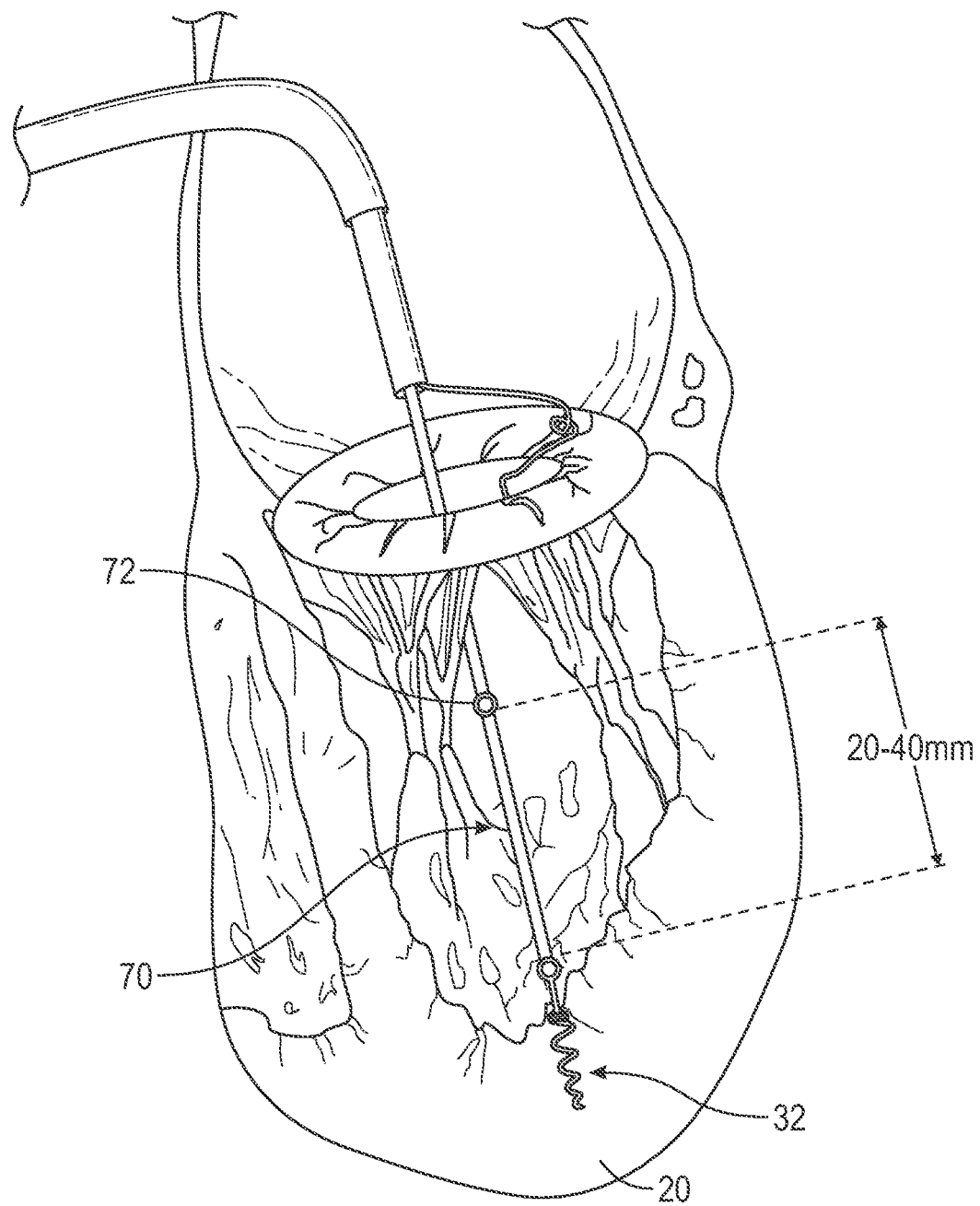
FIG. 5 illustrates the distal anchor attached and projected above the apex of the heart approximately the same height as the top of the papillary muscles.
Figure 6:
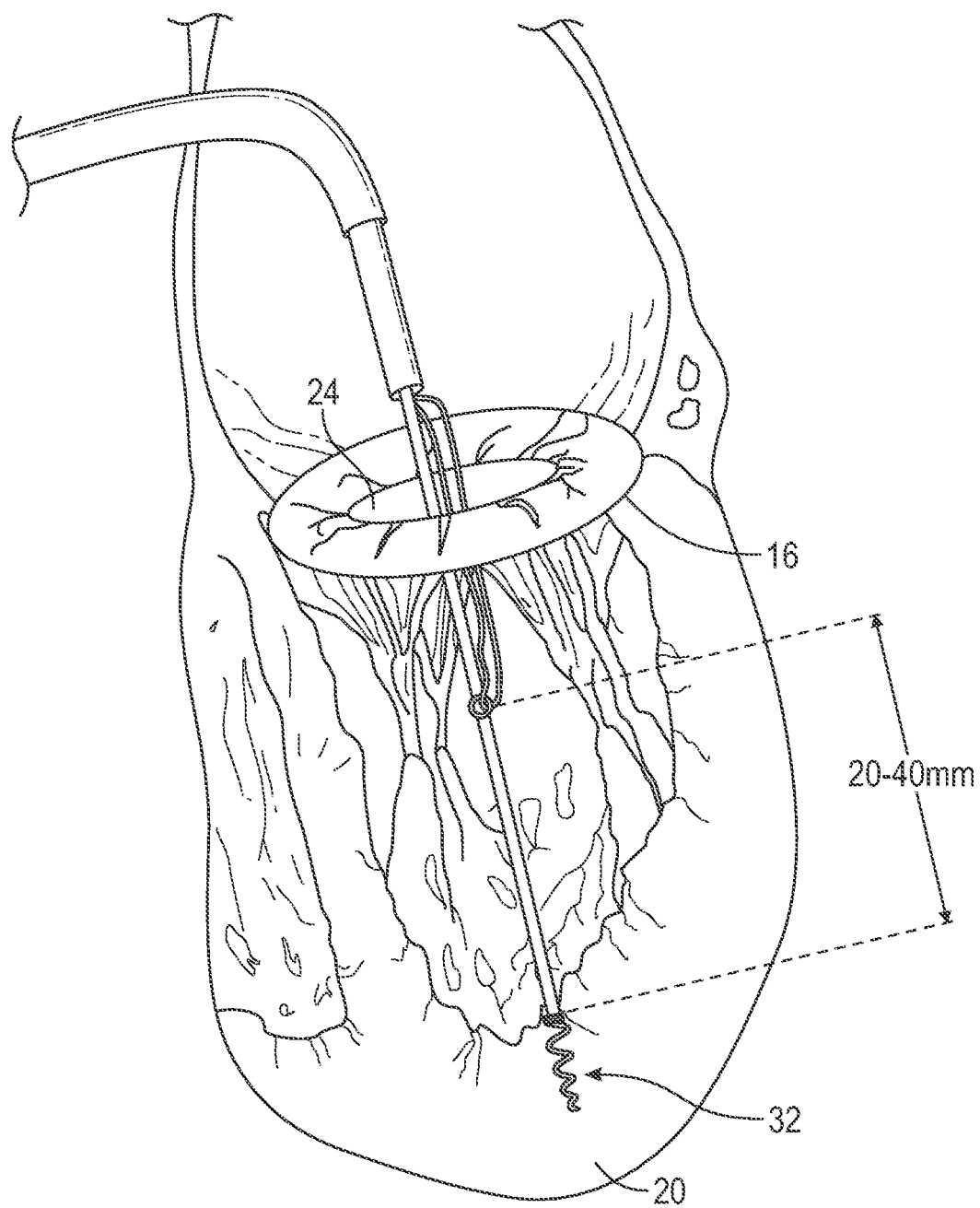
FIG. 6 illustrates the distal anchor attached and projected above the apex of the heart approximately the same height as the top of the papillary muscles and attached to the mitral annulus and or mitral leaflet.
Figure 7:
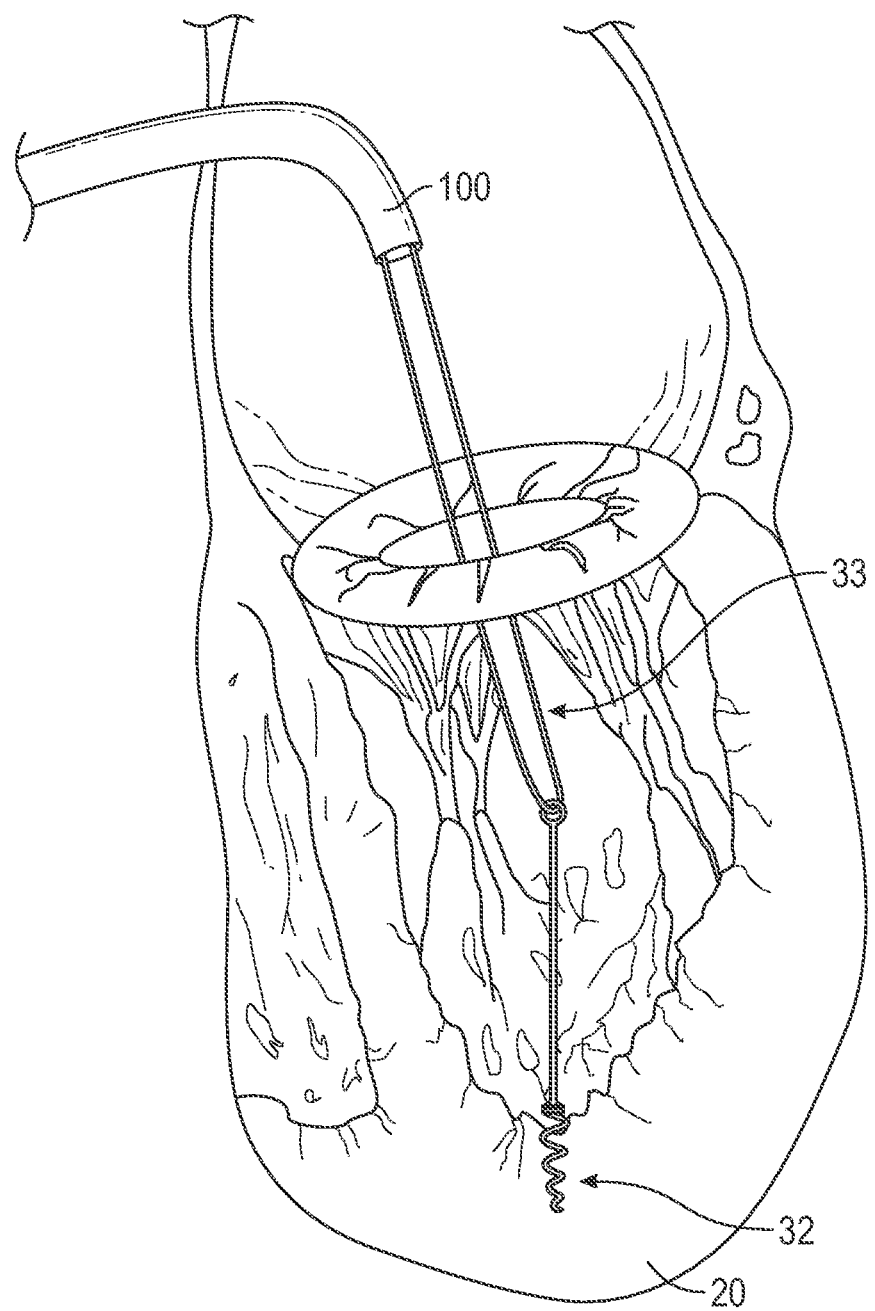
FIG. 7 illustrates the distal anchor attached and projected above the apex of the heart approximately the same height as the top of the papillary muscles and attached to a loop suture traversing through the catheter.

According to one embodiment (see FIGS. 1-7), the steps of the replacement chord delivery could include:
1. Trans-venous, trans-femoral entry of the delivery catheter 100
2. Catheter 100 advancement to the right atrium 10
3. Catheter 100 advancement trans-septal 12 into the left atrium 14
4. Catheter 100 advancement to the mitral annulus 16 for the strain relief anchor 18 positioning and delivery
5. Positioning of a grasping tool of the mitral leaflet
6. Strain relief anchor 18 attachment to the mitral annulus 16
7. Replacement Chord 22 advancement over the mitral valve 25 and between the existing chords 17
8. Chord 22 advancement to the apex 20 of the left ventricle and distal attachment into the apex 20
9. Tensioning of the chord 22 while monitoring the mitral valve leaflet motion Alternatively, in certain embodiments (see e.g., FIGS. 26-34), the delivery could be in a somewhat opposite order:
1. Trans-femoral entry of the delivery catheter 100
2. Catheter 100 advancement to the right atrium 10
3. Catheter 100 advancement trans-septal 12 into the left atrium 14
4. Advancement of the delivery catheter 100 through the mitral valve 24 to the apex 20 of the left ventricle
5. Delivery of the rotational anchor 30 into the apex 20
6. A withdrawal of the delivery catheter 100 to expose the lower apex anchor 30
7. Pulling the delivery catheter 100 proximal to expose the new chord suture line 22 or lines 22
8. Over each new chord 22 a mitral leaflet strain relief can be delivered through the mitral leaflet and on the ventricular side of the leaflet
9. An advancement of a suture lock 26 over the suture tail 28 to lock the position of the suture to the position of the strain relief anchor
10. A cutting of the suture tail at the mitral leaflet anchor
11. An advancement of a suture lock 26 over the suture tail from the catheter handle to the mitral leaflet anchor
12. An advancement of a suture lock 26 over the suture tail from the catheter handle to the distal apex anchor locking the tension as applied from the distal most suture tail outside the catheter handle
13. A cutting of the suture tail at the distal apex anchor An embodiment according to FIGS. 1-7 will now be described with additional detail. FIG. 1 illustrates the mitral valve annulus 16 with the suture 22 attached as delivered via the catheter 100. FIG. 2 illustrates the distal anchor 32 being delivered via the catheter 100 and attached to the suture 22 further connected to the mitral annulus 16. FIG. 3 illustrates the distal anchor 32 being rotated into the apex 20 of the heart with suture lines 22 attached for later attachment to the mitral leaflet 24 or the mitral annulus 16. FIG. 4 illustrates the distal anchor 32 rotated into the apex 20 of the heart with suture lines 22 attached to the mitral leaflet 24 or the mitral annulus 17. FIG. 5 illustrates the distal anchor 32 attached and projected above the apex 20 of the heart approximately the same height as the top of the papillary muscles. The anchor 32 can include a riser 70 connected to a connection point 72 having a length of about 20-40 mm in certain embodiments. FIG. 6 illustrates the distal anchor 32 attached and projected above the apex 20 of the heart approximately the same height as the top of the papillary muscles and attached to the mitral annulus 16 and or mitral leaflet 24. FIG. 7 illustrates the distal anchor 32 attached and projected above the apex 20 of the heart approximately the same height as the top of the papillary muscles and attached to a suture 33 in a form of a loop traversing through the catheter 100.

Figure 8:
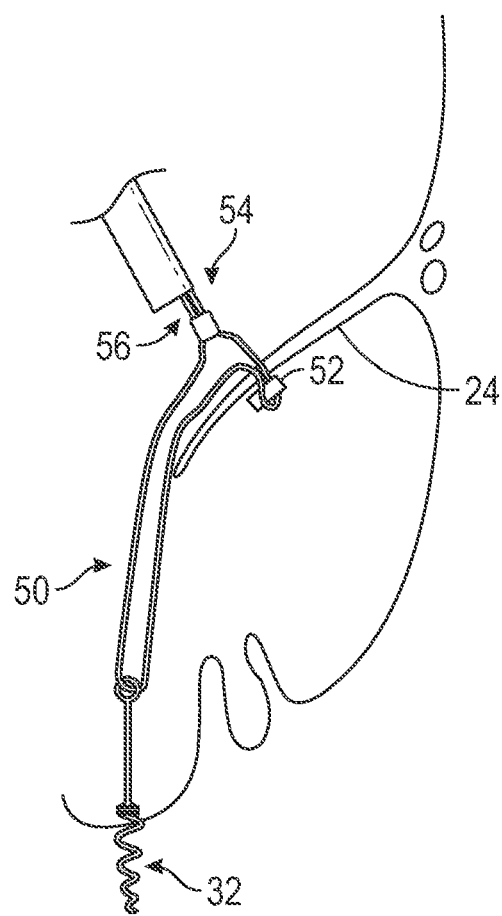
FIG. 8 illustrates a catheter delivered suture loop pierced through the mitral leaflet with a strain relief on the ventricular side of the mitral leaflet and a distal anchor in the bottom of the left ventricle with the final suture tension adjustment being held with a suture lock advanced over the suture tails.

FIG. 8 illustrates an embodiment in which a catheter delivered suture 50 in a form of a loop can be pierced through the mitral leaflet 24 with a strain relief 52 on the ventricular side of the mitral leaflet 24 and a distal anchor 32 in the bottom of the left ventricle with the final suture tension adjustment being held with a suture lock 54 advanced over the suture tails 56.

Figure 9:
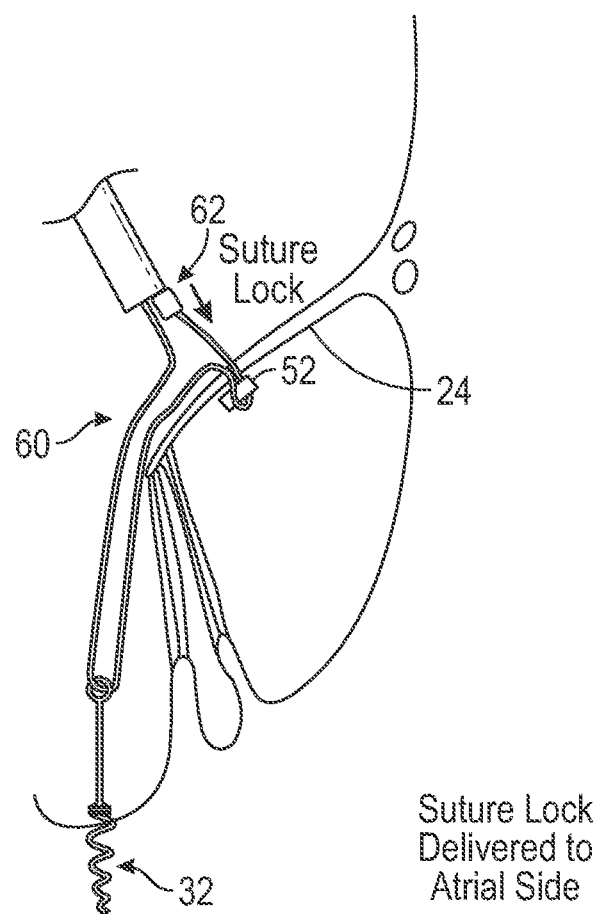
FIG. 9 illustrates a catheter delivered suture line pierced through the mitral leaflet with a strain relief on the ventricular side of the mitral leaflet and a suture lock being advanced to the atrial side of the mitral leaflet to secure the suture tail before cutting of the suture.

FIG. 9 illustrates an embodiment in which a catheter delivered suture line or loop 60 can be pierced through the mitral leaflet 24 with a strain relief 52 on the ventricular side of the mitral leaflet 24. In this embodiment, a suture lock 62 can be advanced to the atrial side of the mitral leaflet 24 to secure the suture tail before cutting of the suture 60

Figure 10:
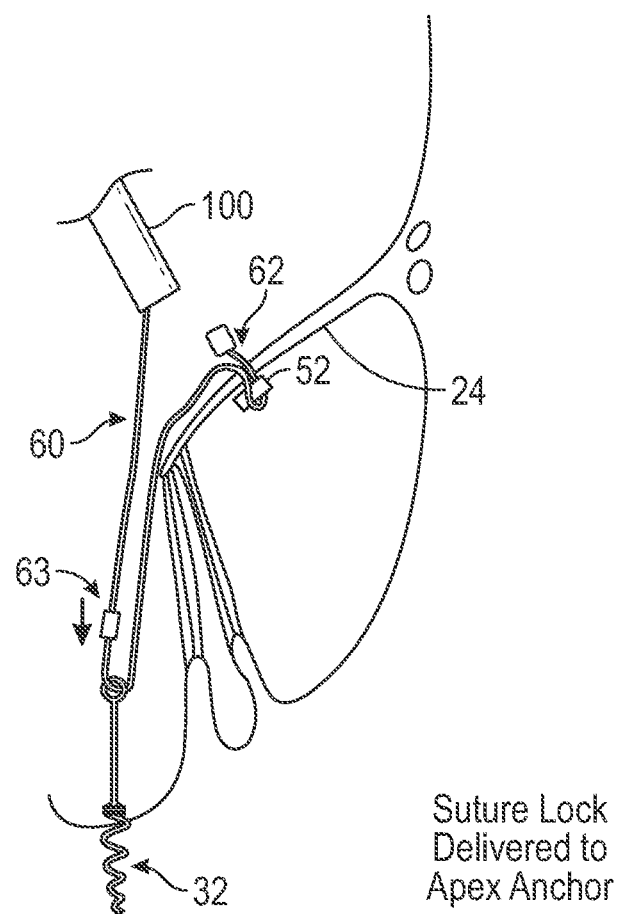
FIG. 10 illustrates a catheter delivered suture line pierced through the mitral leaflet with a strain relief on the ventricular side of the mitral leaflet and a suture lock advanced to the atrial side of the mitral leaflet to secure the suture tail. The other end of the suture tail extends from the catheter handle through the catheter traversing about the distal anchor located in the bottom of the left ventricle for tensioning of the suture. A second suture lock is advanced over the final suture tail once the suture tension is adjusted by the user.

FIG. 10 illustrates an embodiment in which a catheter delivered suture line 60 can be pierced through the mitral leaflet 25 with a strain relief 52 on the ventricular side of the mitral leaflet 25 and a suture lock 62 advanced to the atrial side of the mitral leaflet to secure the suture tail. The other end of the suture tail extends from the catheter handle through the catheter 100 traversing about the distal anchor 32 located in the bottom of the left ventricle for tensioning of the suture. A second suture lock 63 can be advanced over the final suture tail once the suture tension is adjusted by the user.

Figure 11:
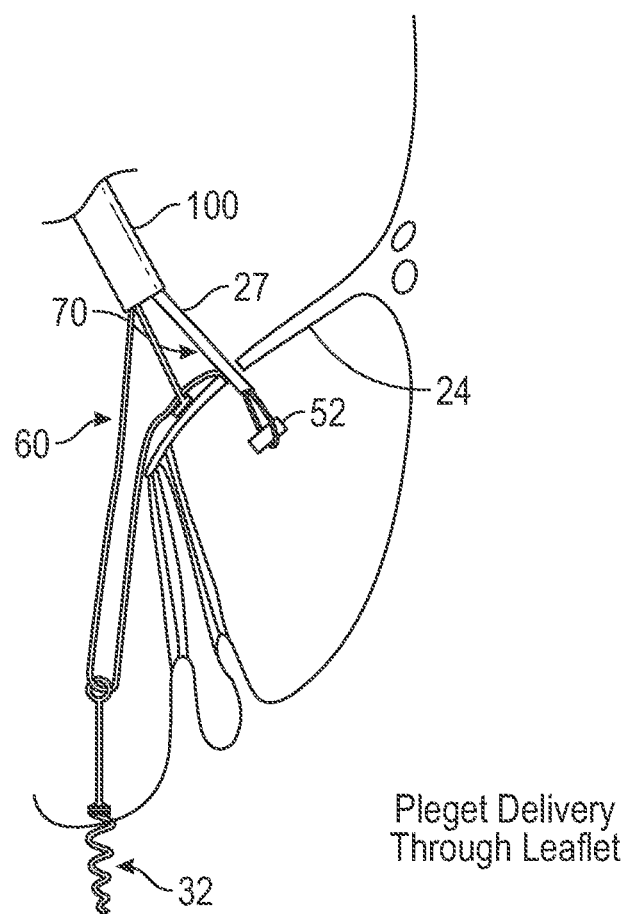
FIG. 11 illustrates a catheter delivered suture loop pierced through the mitral leaflet with a strain relief on the ventricular side of the mitral leaflet in a looped configuration about the strain relief and a distal anchor in the bottom of the left ventricle with the final suture tension adjustment being held with a suture lock advanced over the suture tails. Holding the leaflet steady and counteracting the piercing force of the strain relief is illustrated a cryo-catheter sticking to the mitral leaflet.

FIG. 11 illustrates an embodiment in which a catheter delivered suture loop 60 can be pierced with a piercing element 27 (e.g., a needle) through the mitral leaflet with a strain relief on the ventricular side of the mitral leaflet 24 in a looped configuration about the strain relief 52 and a distal anchor 32 in the bottom of the left ventricle with the final suture tension adjustment being held with a suture lock advanced over the suture tails. Holding the leaflet steady and counteracting the piercing force of the strain relief can be accomplished using a cryo-catheter 70 sticking to the mitral leaflet 24.

Figure 12:
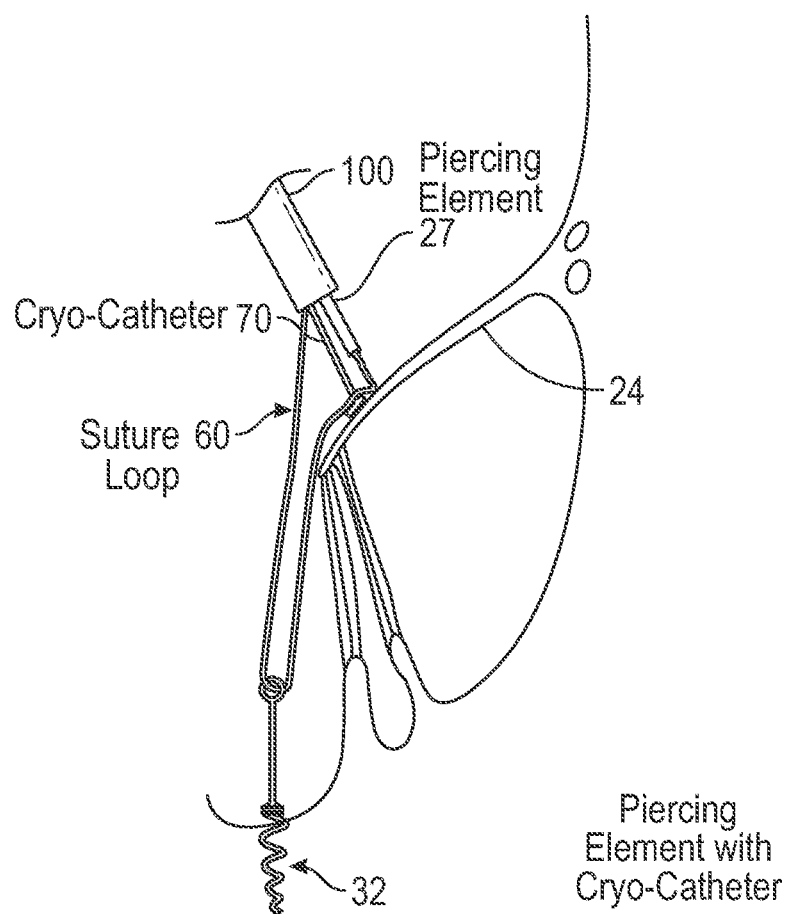
FIG. 12 illustrates a catheter delivered suture loop pierced through the mitral leaflet with a strain relief to be delivered on the ventricular side of the mitral leaflet in a looped configuration about the strain relief and a distal anchor in the bottom of the left ventricle with the final suture tension adjustment being held with a suture lock advanced over the suture tails. Holding the leaflet steady and counteracting the piercing force of the strain relief is illustrated a cryo-catheter sticking to the mitral leaflet.

FIG. 12 illustrates a catheter delivered suture loop 60 pierced through the mitral leaflet 24 with a strain relief to be delivered on the ventricular side of the mitral leaflet in a looped configuration about the strain relief and a distal anchor 32 in the bottom of the left ventricle with the final suture tension adjustment being held with a suture lock advanced over the suture tails. Holding the leaflet steady and counteracting the piercing force of the strain relief is illustrated a cryo-catheter 70 sticking to the mitral leaflet.

Figure 13:
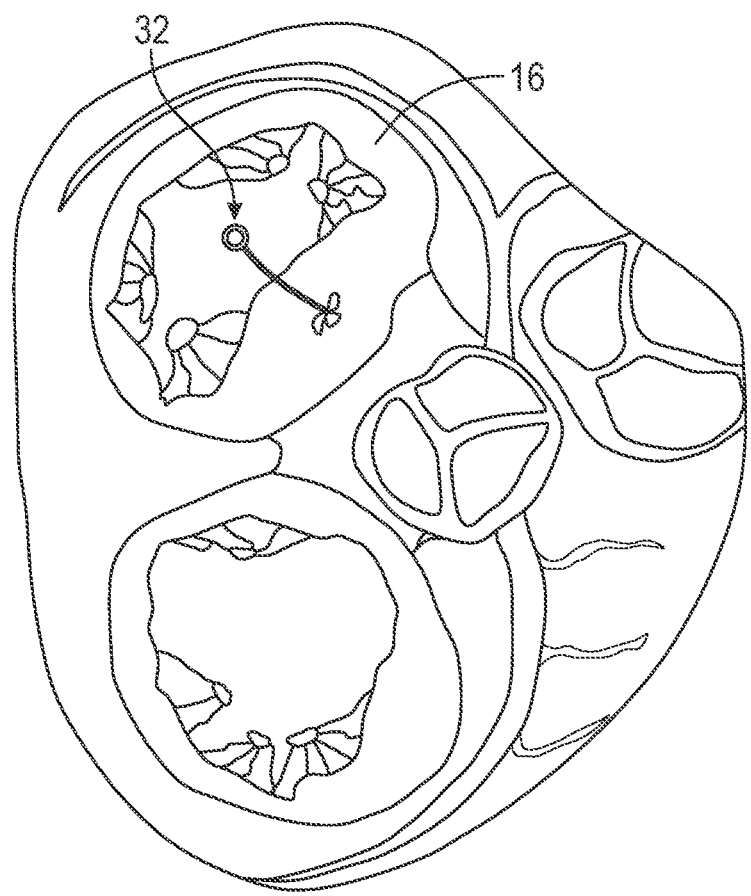
FIG. 13 illustrates a view from the atrial side showing where the mitral annulus is pierced and where the distal anchor is located with respect to the native papillary muscles.
Figure 14:
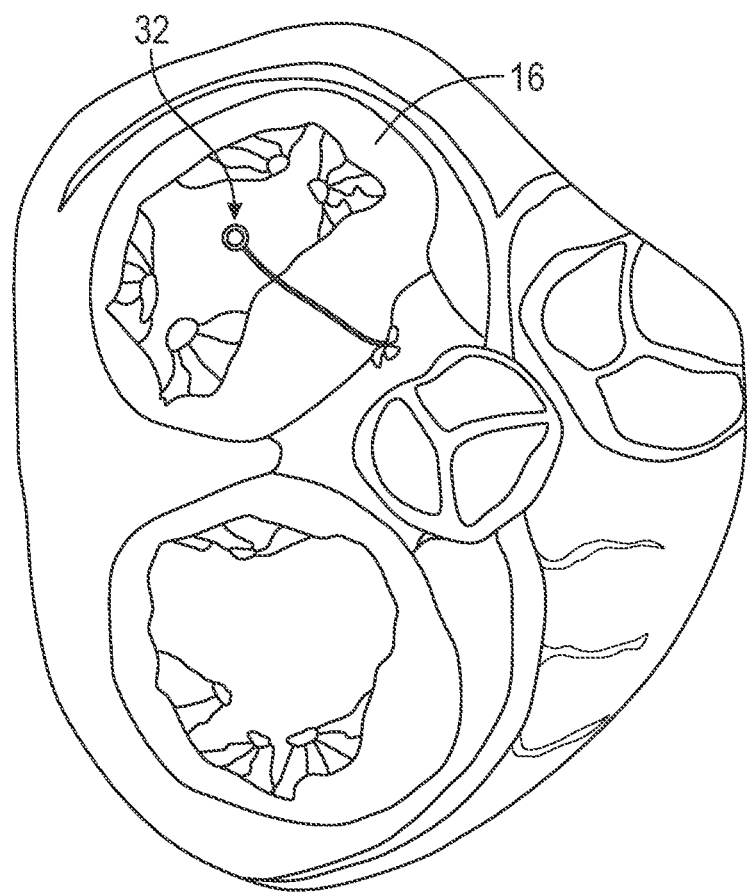
FIG. 14 illustrates a view from the atrial side showing where the mitral annulus is pierced and where the distal anchor is located with respect to the native papillary muscles.
Figure 15:
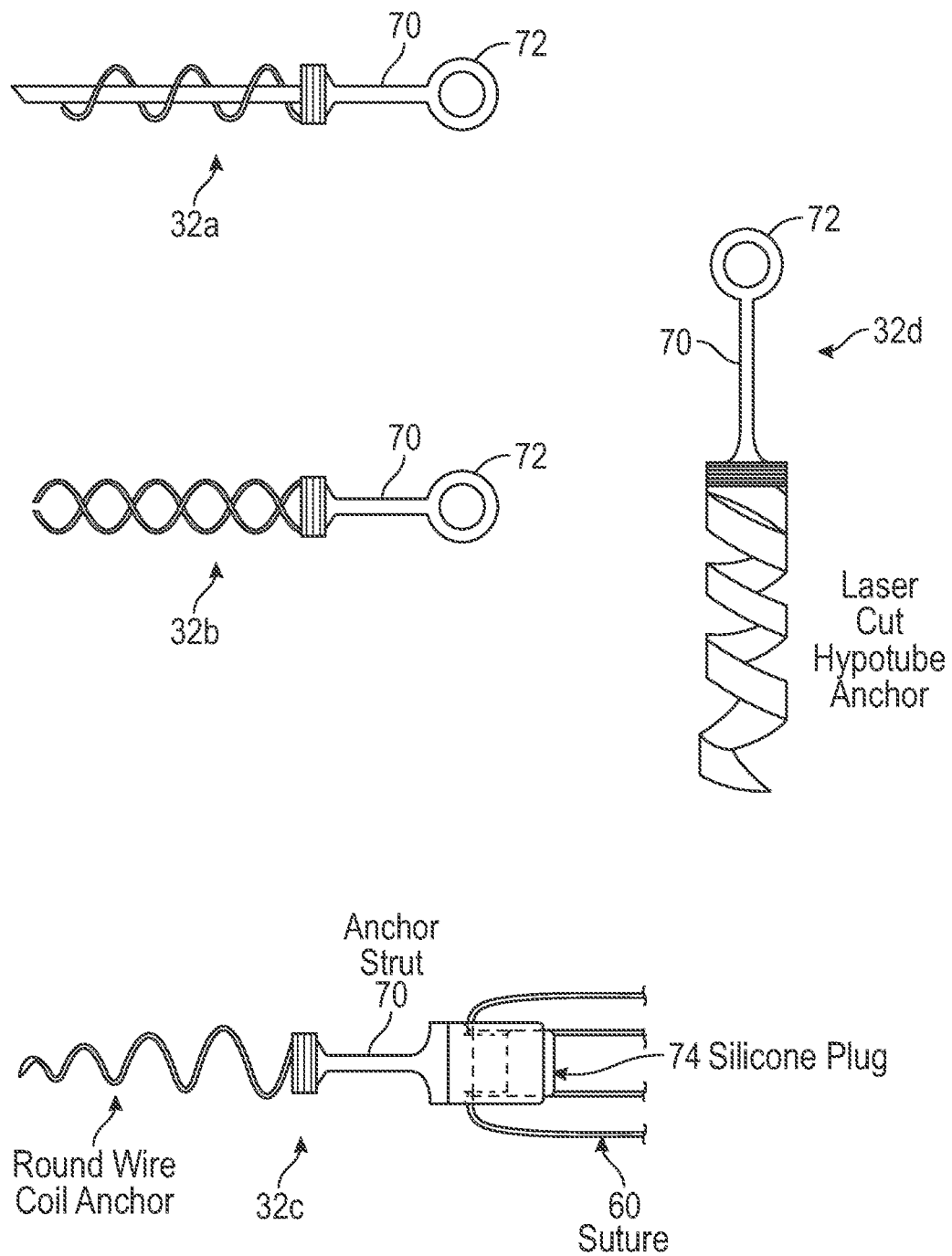
FIG. 15 illustrates a variety of anchors for attachment into the apex of the left ventricle including coiled round wire and laser cut hypo-tube with vertical risers adjusting the connection point closer to the height of the papillary muscles to better simulate the correct angle and match the new chordal connections.

FIGS. 13 and 14 illustrates a views from the atrial side showing where according to certain embodiments the mitral annulus 16 is pierced and where the distal anchor 32 is located with respect to the native papillary muscles FIG. 15 illustrates a variety of anchors embodiments 32*a*, 32*b*, 32*c*, 32*d*, for attachment into the apex of the left ventricle including coiled round wire 32*a*, 32*b*, 32*c* and laser cut hypo-tube 32*b* with vertical risers 70 adjusting the connection point 72 closer to the height of the papillary muscles to better simulate the correct angle and match the new chordal connections. The anchor 32*c* includes a riser 70 in th form of a strut and the connection point 72 that can receive the suture 60, which can be secured within the connection point 72 by a silicone plug 74.

Figure 16:
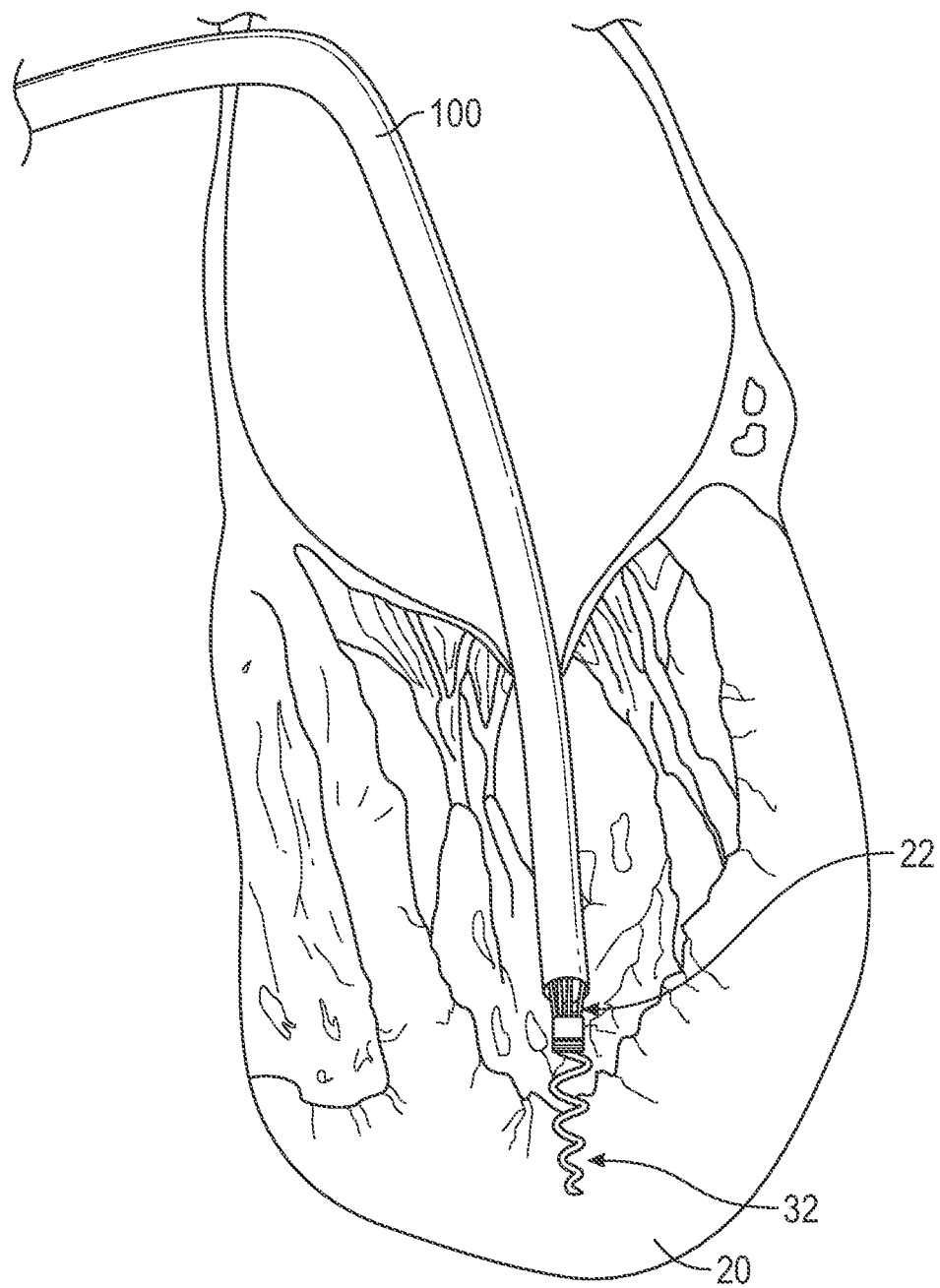
FIG. 16 illustrates a trans-septal catheter delivering an anchor in the apex of the left ventricle with a plurality of replacement chords attached and extending out the handle of the catheter.
Figure 17:
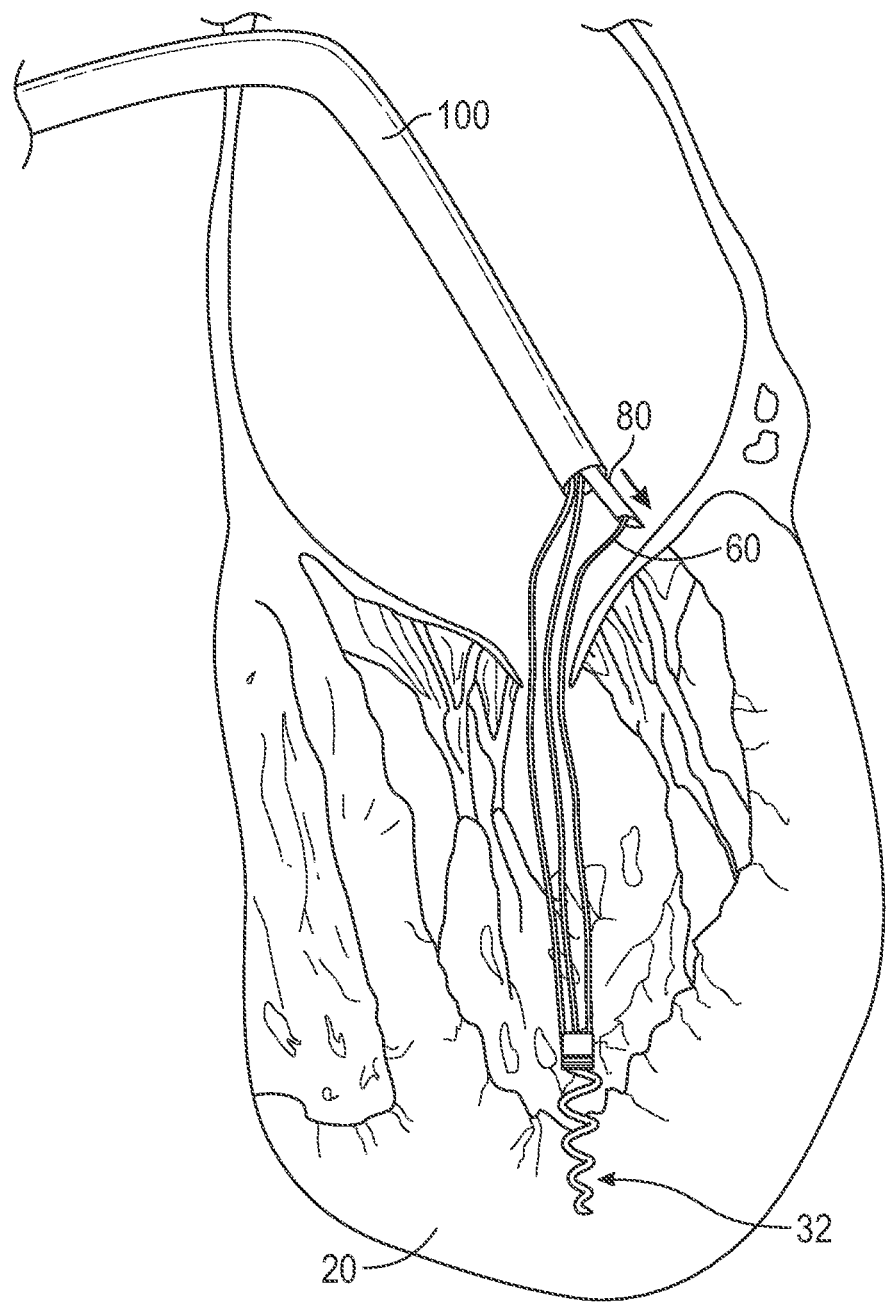
FIG. 17 illustrates a trans-septal catheter delivering a piercing tool through the mitral leaflet to deliver a strain relief anchor connected to a suture loop.
Figure 18:
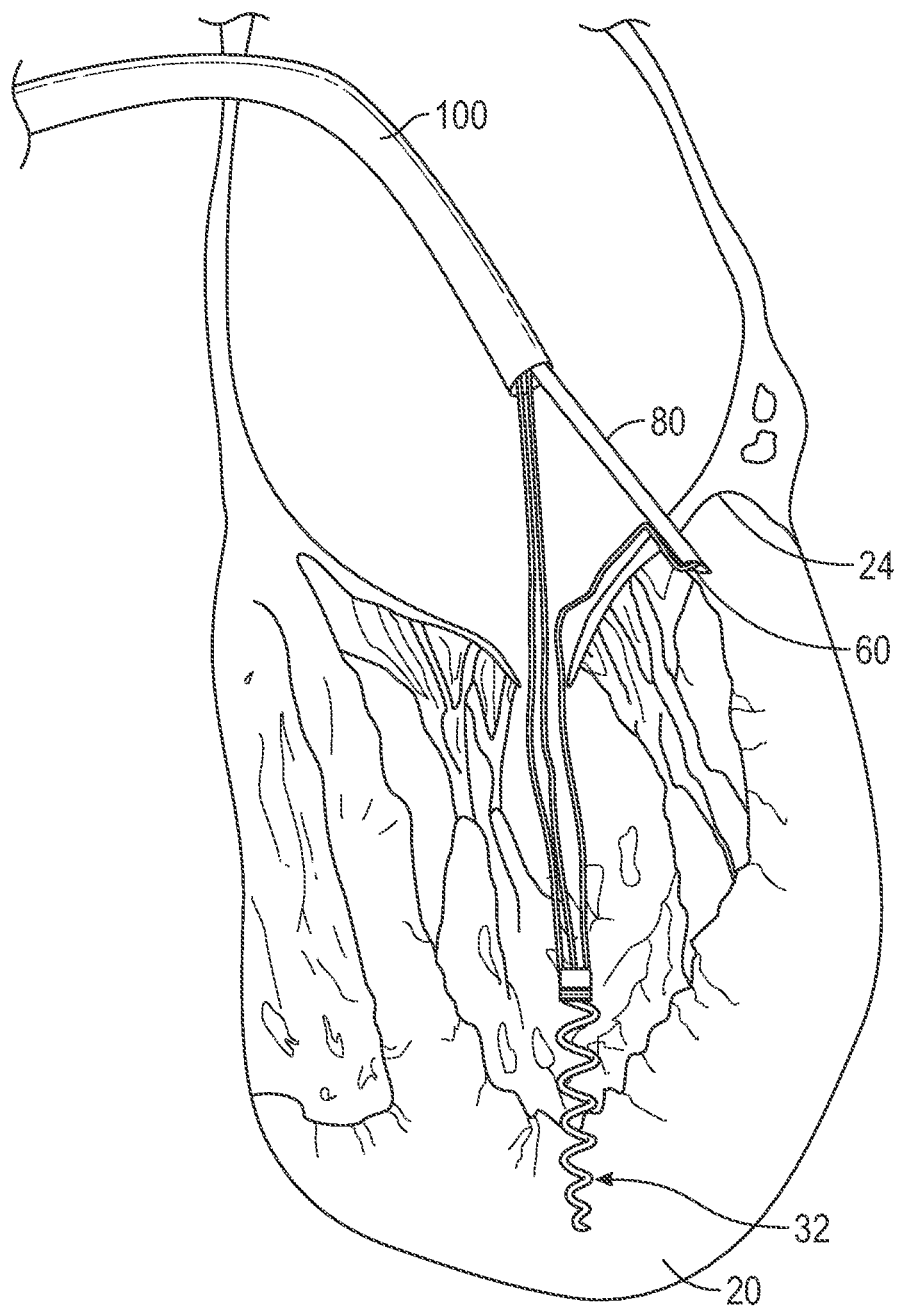
FIG. 18 illustrates a trans-septal catheter delivering a suture loop through the mitral leaflet piercing through the leaflet with the suture loop.
Figure 19:
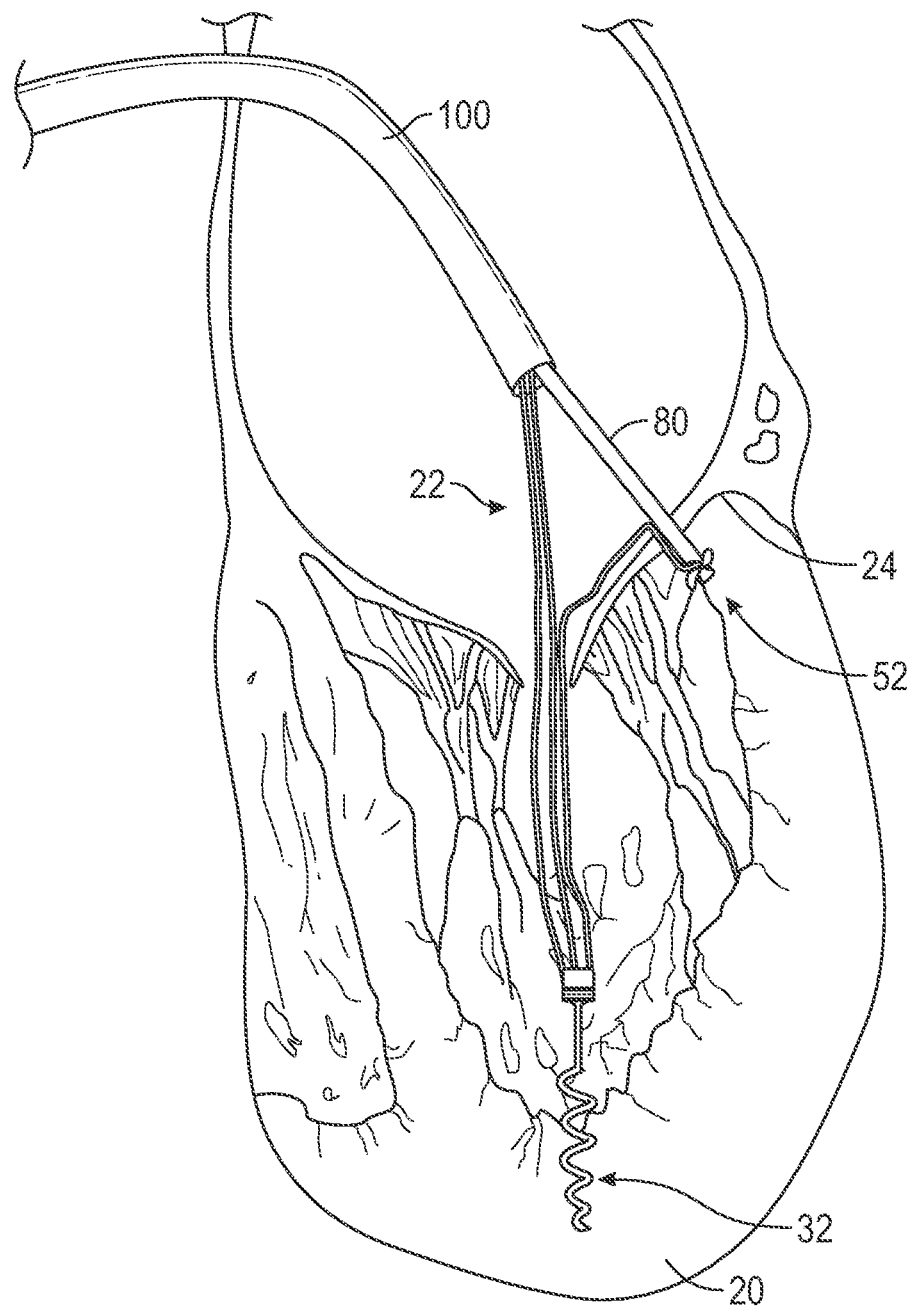
FIG. 19 illustrates a trans-septal catheter delivering the strain relief to the ventricle side of the mitral leaflet exposing it for delivery through or with the piercing tool
Figure 20:
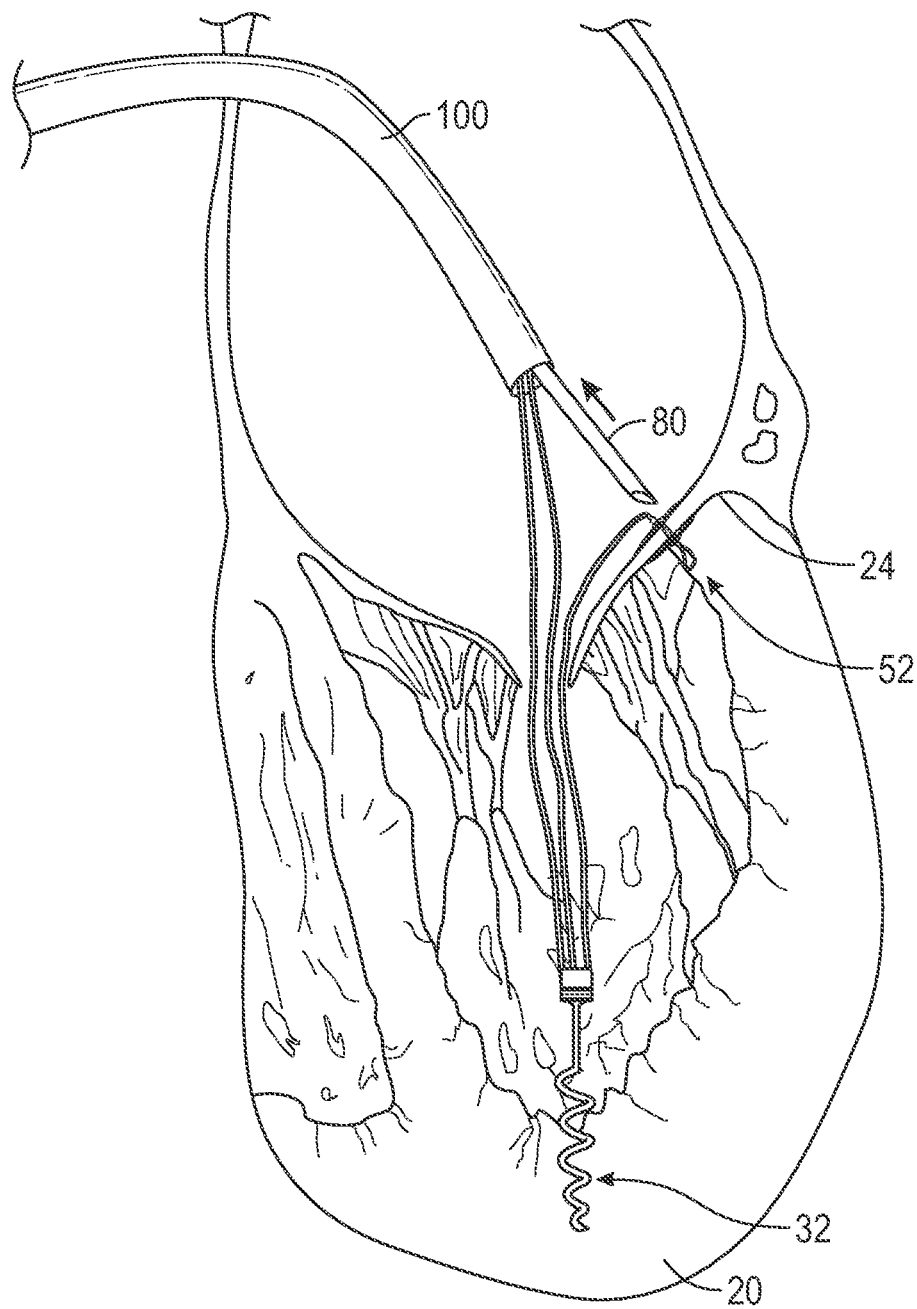
FIG. 20 illustrates a trans-septal catheter delivering the strain relief and the piercing tool being withdrawn for the mitral leaflet.
Figure 21:
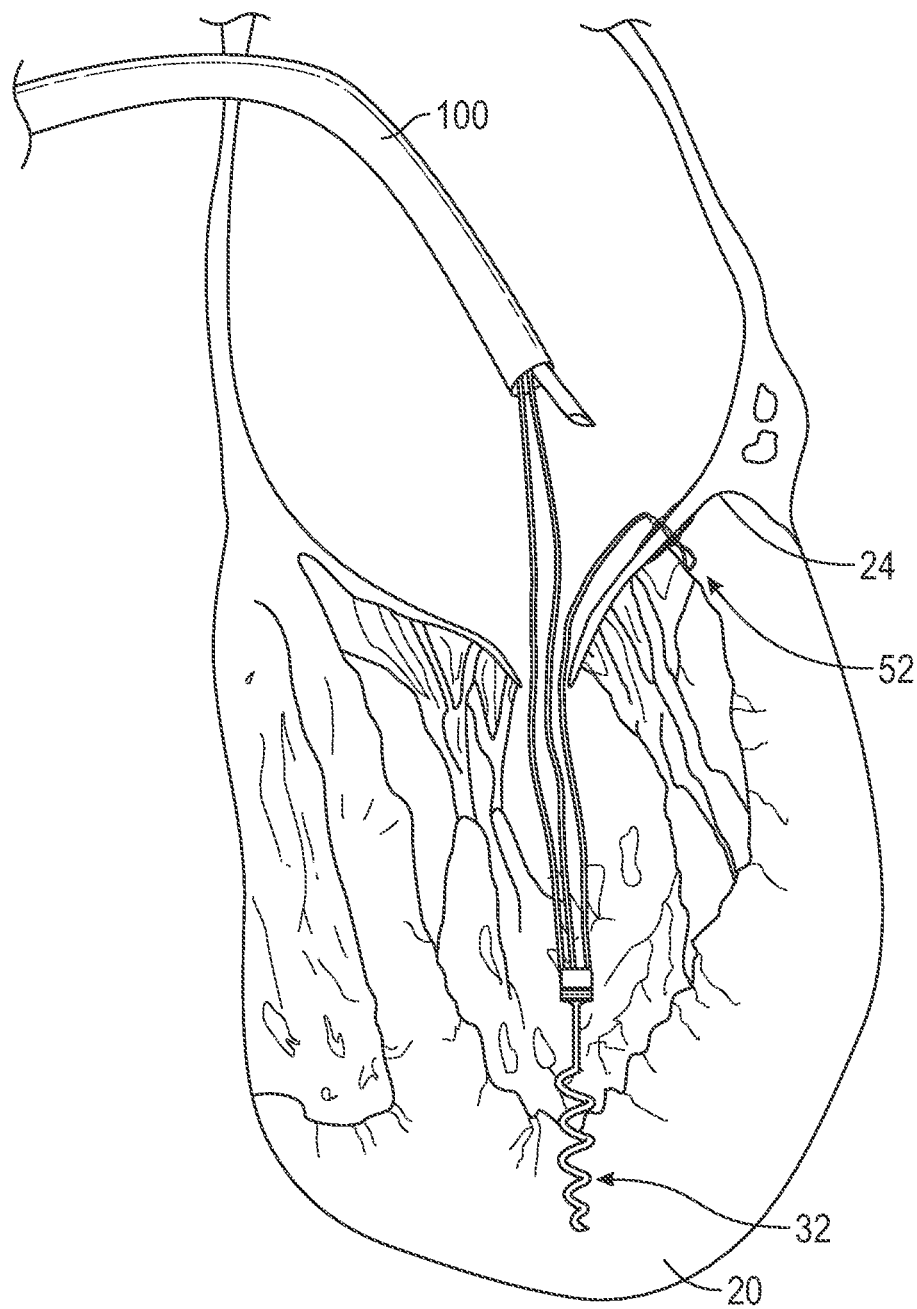
FIG. 21 illustrates a trans-septal catheter delivering the strain relief with the connection to the distal anchor and the suture loop extending back out the catheter handle.
Figure 22:
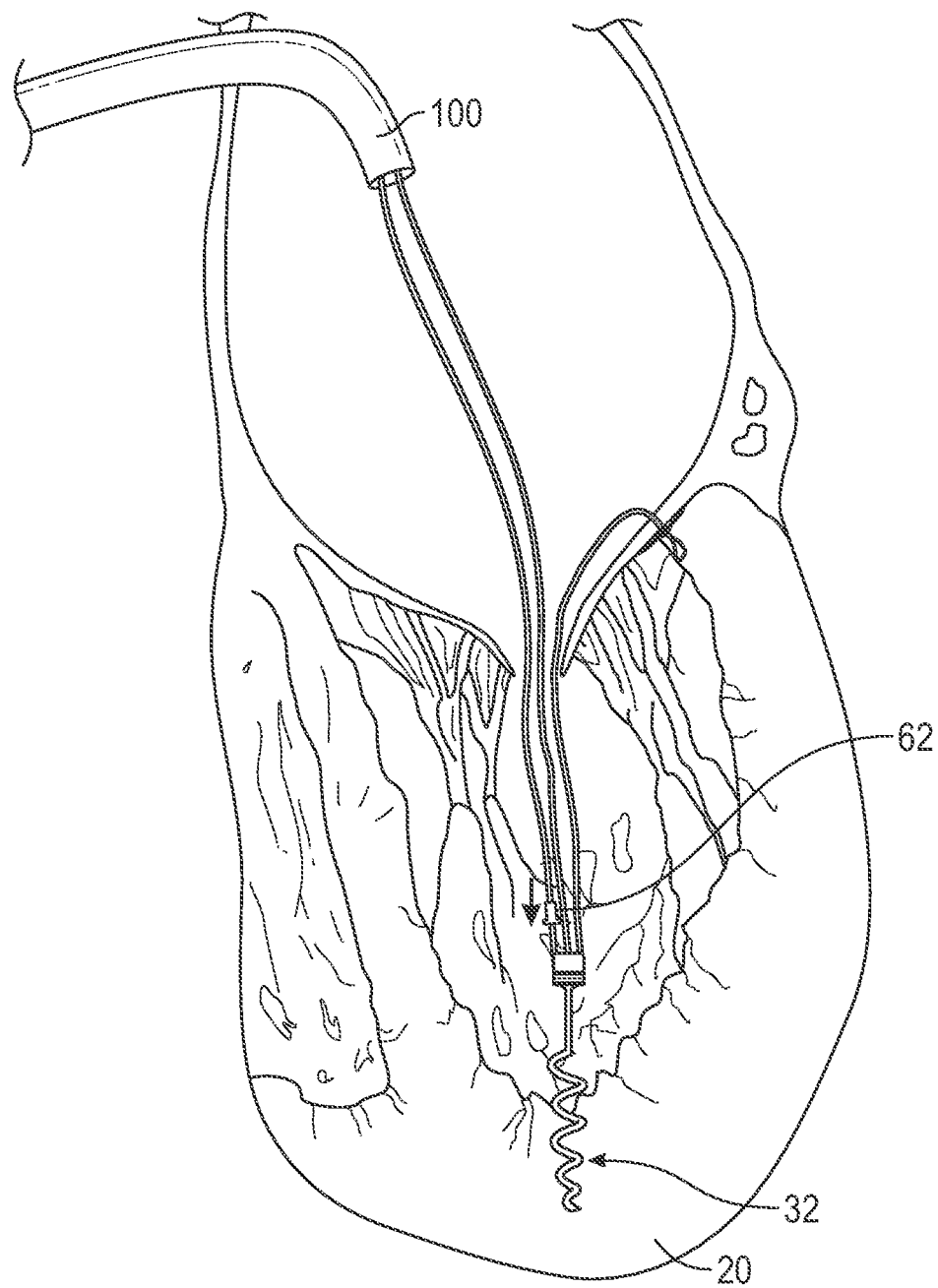
FIG. 22 illustrates a trans-septal catheter delivering a suture lock to the distal anchor being advanced over the suture tail while tension is applied from the proximal end of the suture back our the catheter handle to adjust the position and tension of the final implant suture connected now to the mitral leaflet and the distal apex anchor.

FIGS. 16-22 illustrate another method according to certain embodiments. FIG. 16 illustrates a trans-septal catheter delivering an anchor 32 in the apex 20 of the left ventricle with a plurality of replacement chords 22 attached and extending out the handle of the catheter 100. FIG. 17 illustrates the trans-septal catheter 100 o of FIG. 16 delivering a piercing tool 80 through the mitral leaflet 24 to deliver a strain relief anchor connected to a suture loop 60. FIG. 18 illustrates the trans-septal catheter 100 delivering a suture loop 60 through the mitral leaflet 24 piercing through the leaflet 24 with the suture loop 24. FIG. 19 illustrates the trans-septal catheter 100 delivering the strain relief to the ventricle side of the mitral leaflet 24 exposing it for delivery through or with the piercing tool 80. FIG. 20 illustrates the trans-septal catheter delivering the strain relief 52 and the piercing tool 80 being withdrawn from the mitral leaflet 24. FIG. 21 illustrates the trans-septal catheter 100 delivering the strain relief 52 with the connection to the distal anchor 32 and the suture loop 60 extending back out the catheter handle FIG. 22 illustrates the trans-septal catheter delivering a suture lock 62 to the distal anchor 32 being advanced over the suture tail while tension is applied from the proximal end of the suture back our the catheter handle to adjust the position and tension of the final implant suture connected now to the mitral leaflet and the distal apex anchor.

Figure 23:
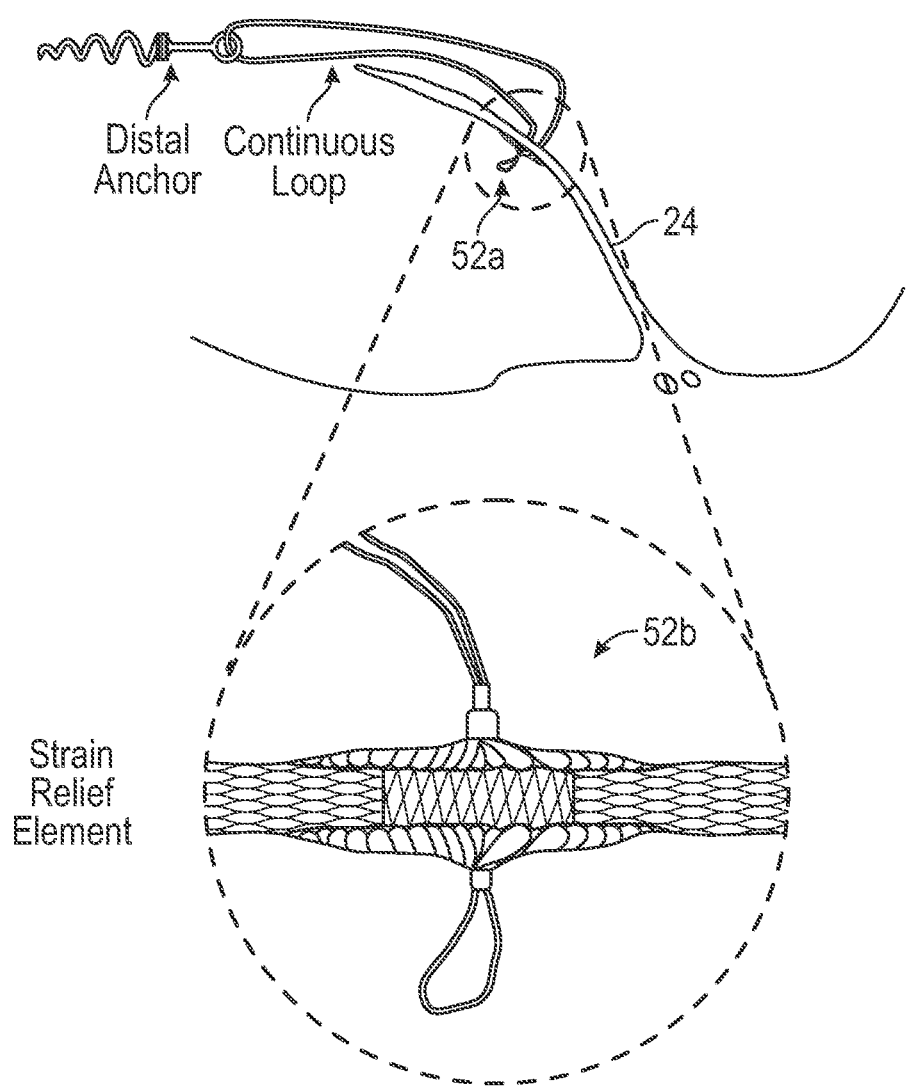
FIG. 23 illustrates a final suture loop anchoring the distal apex anchor to the mitral leaflet noting the mitral anchor can be single sided flange or a single side as shown in the unexploded view.
Figure 24:
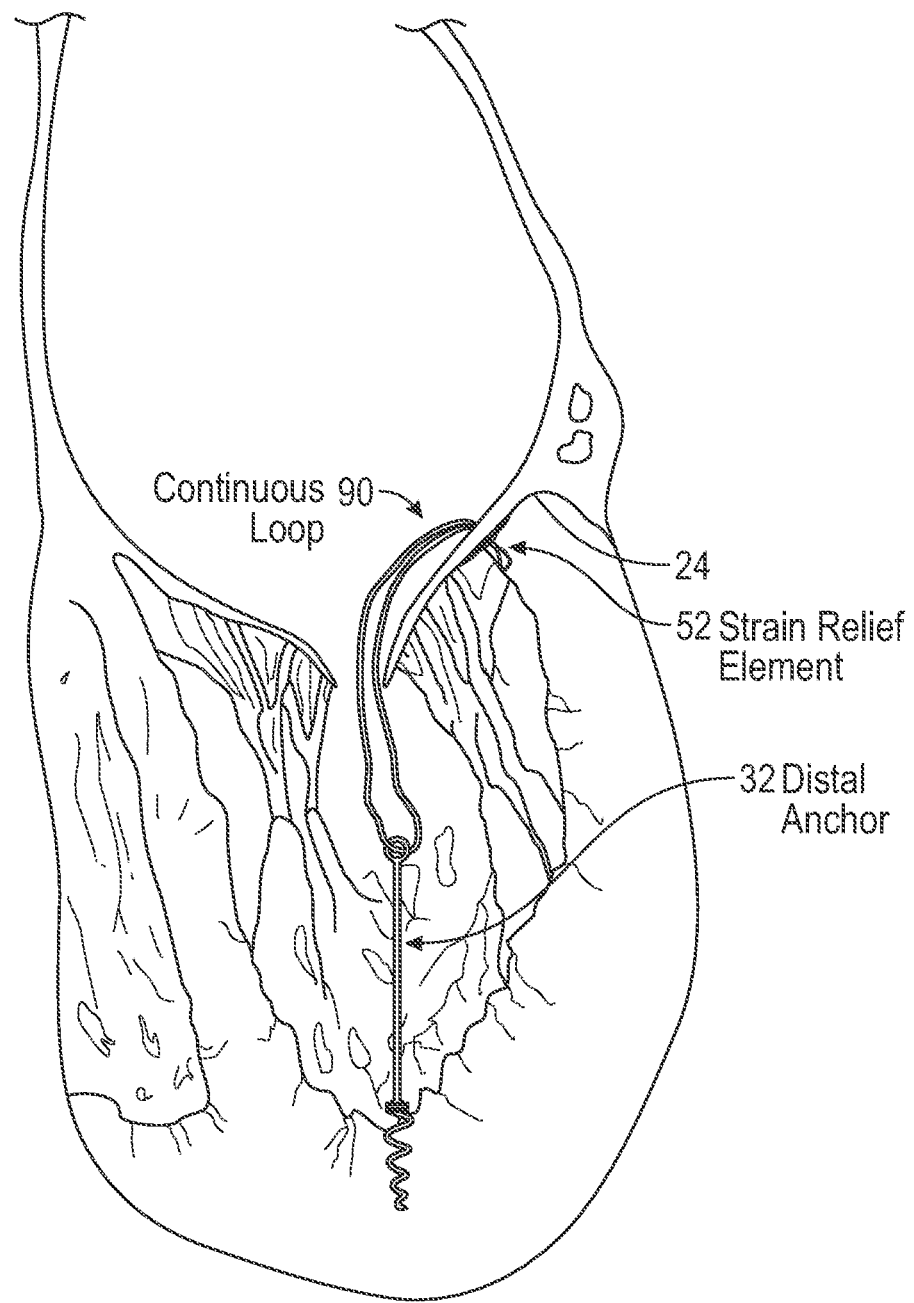
FIG. 24 illustrates a continuous loop anchor delivered in its final position with a distal apex anchor and a strain relief element on the mitral leaflet.

FIG. 23 illustrates an embodiment in which a final suture loop anchoring embodiment in which the distal apex anchor 32 to the mitral leaflet 24 noting the mitral anchor or strain relieve element 52 can be double sided flange 52*b* or a single side flange 52*a* as shown in the unexploded view FIG. 24 illustrates an embodiment in which a continuous loop anchor 90 delivered in its final position with a distal apex anchor 32 and a strain relief element 52 on the mitral leaflet 24.

Figure 25:
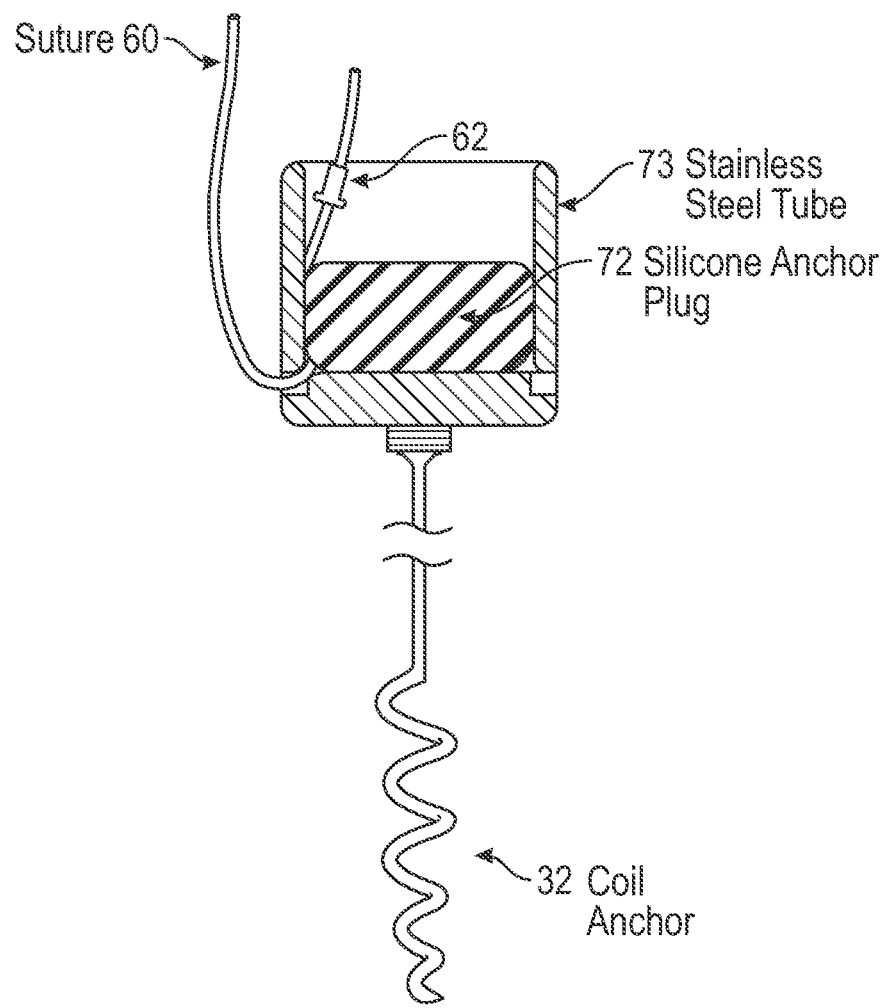
FIG. 25 illustrates an example of a distal apex anchor constructed of a stainless tube and a silicone anchor plug //to limit the suture movement before delivery of the suture lock for final positioning. The materials can be varied and changed to accommodate size and material enhancements.
Figure 26:
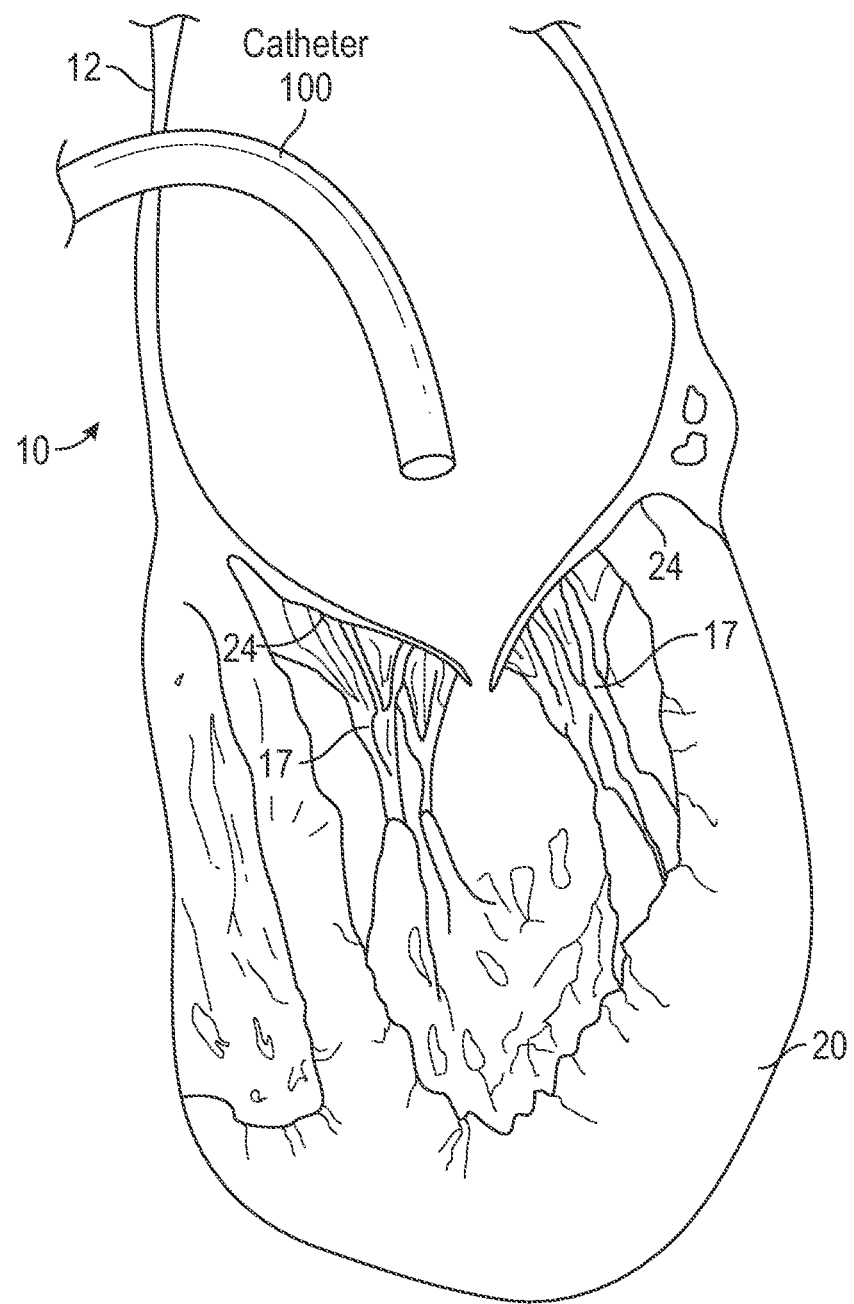
FIG. 26 illustrates a catheter penetrating the septum from the right atrial and the left atrium.
Figure 27:
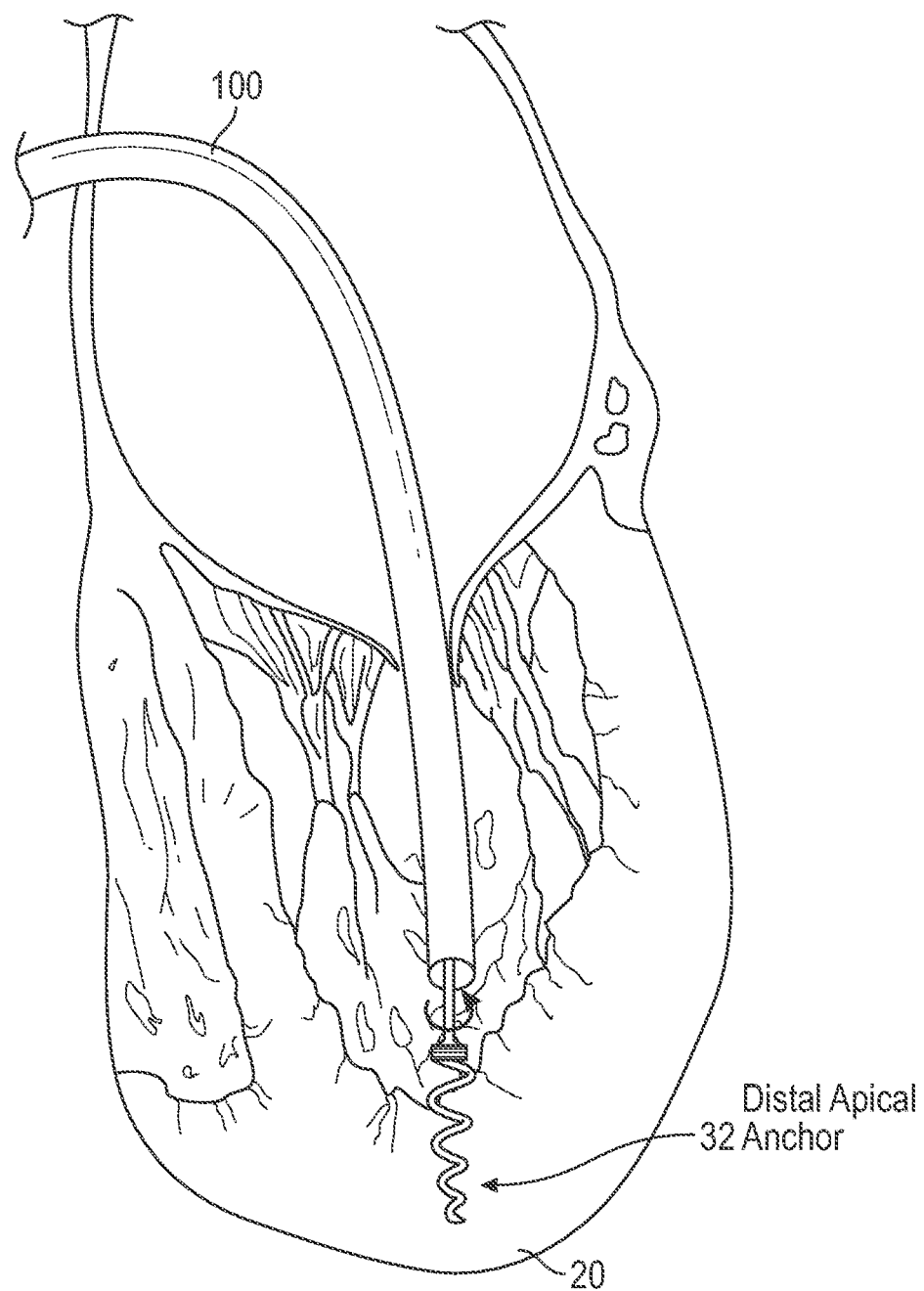
FIG. 27 illustrates an anchor being rotated into the left ventricle.
Figure 28:
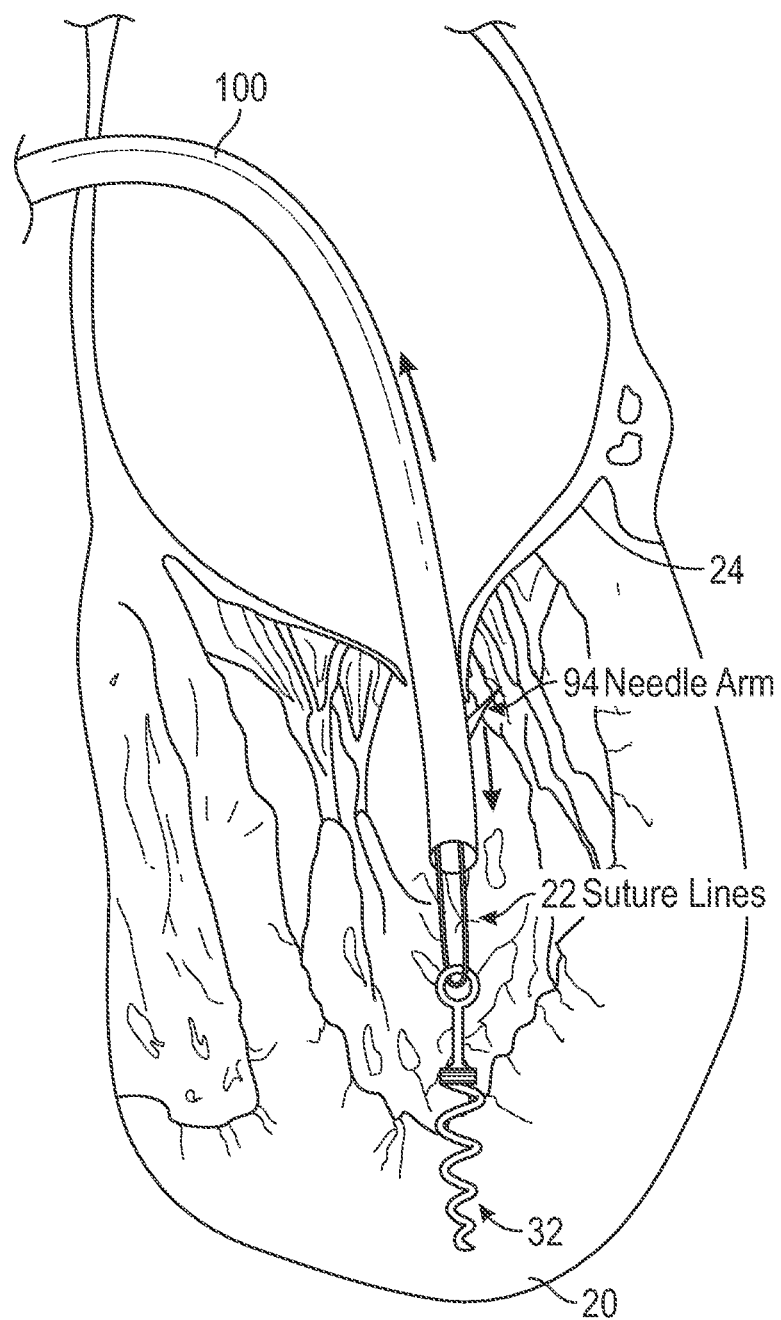
FIG. 28 illustrates the distal apical anchor in place with the suture lines attached and extending back through the catheter and an extension arm exposed to capture the mitral leaflet with a needle to be fired when properly positioned on the leaflet.
Figure 29:
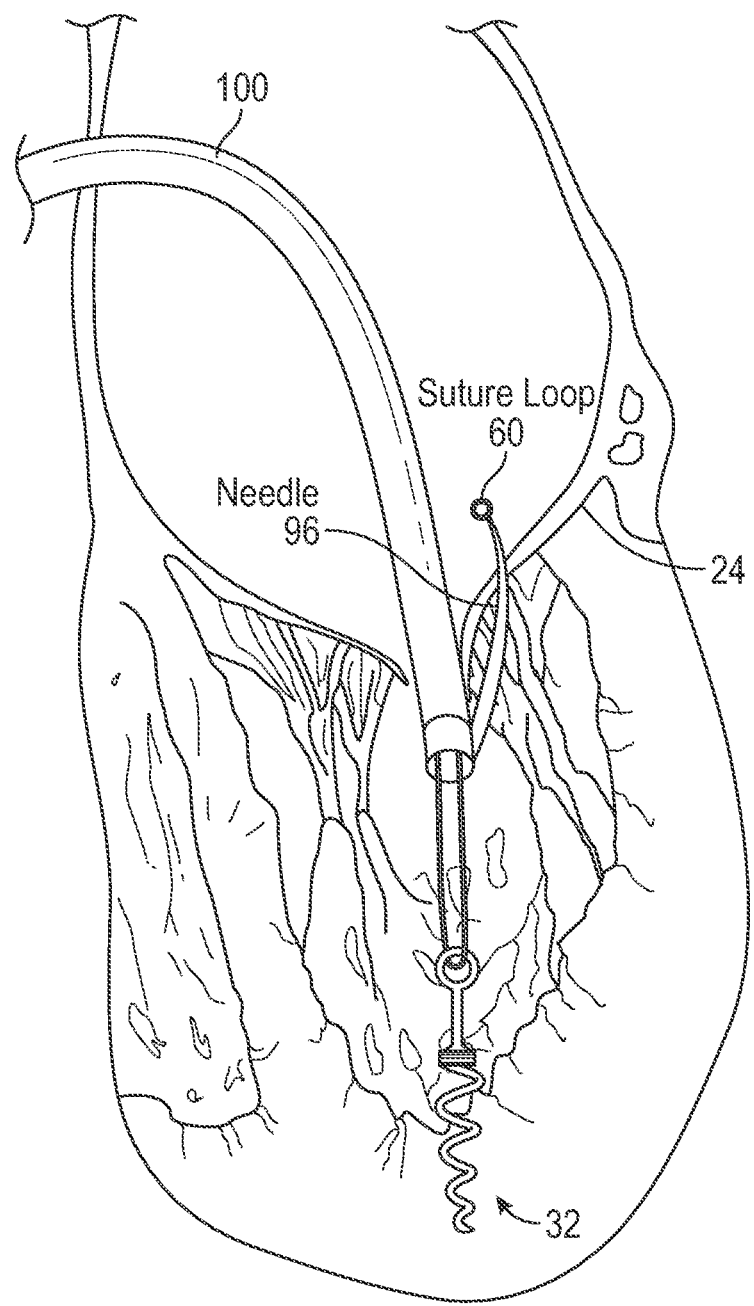
FIG. 29 illustrates the extension arm in contact with the mitral leaflet and the needle connected to a suture loop penetrating the leaflet to expose a suture loop on the atrial side of the mitral leaflet.
Figure 30:
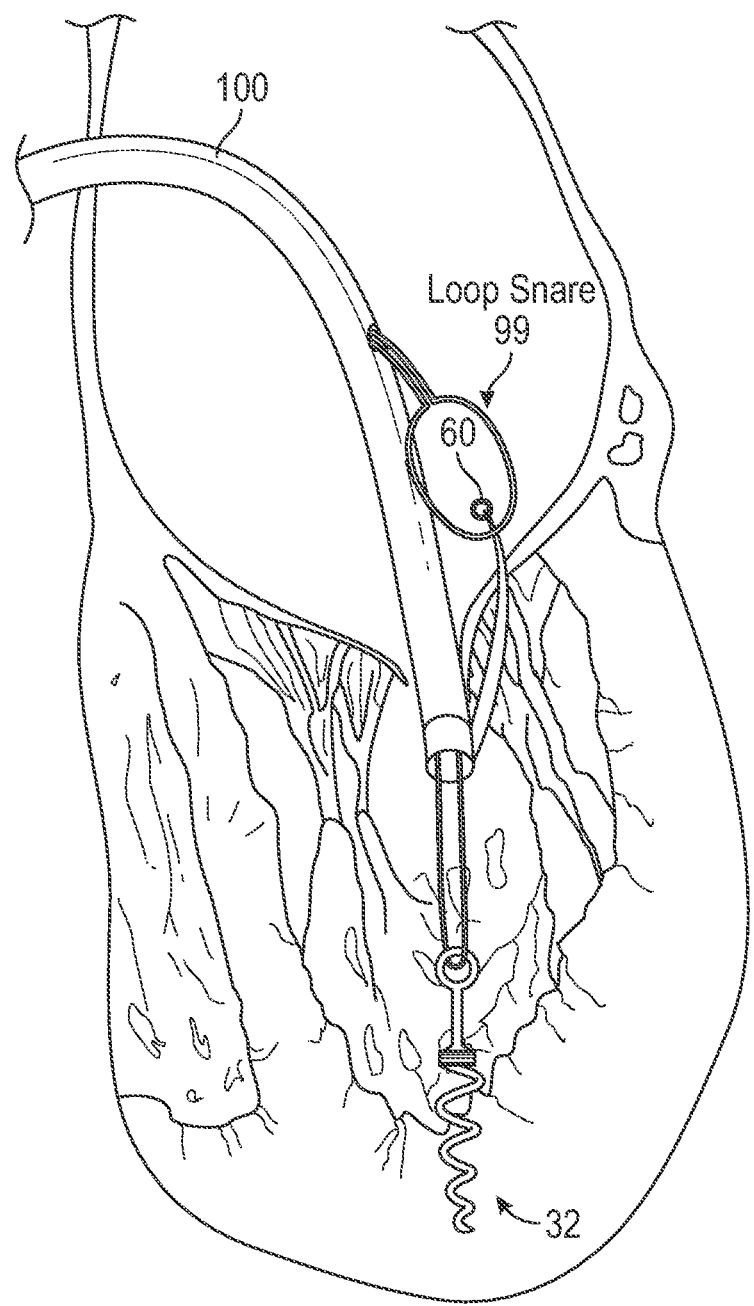
FIG. 30 illustrates the suture loop exposed on the atrial side of the leaflet penetrating through the mitral leaflet to accept a loop-snare for capture of the suture loop and retrieval back through the catheter.
Figure 31:
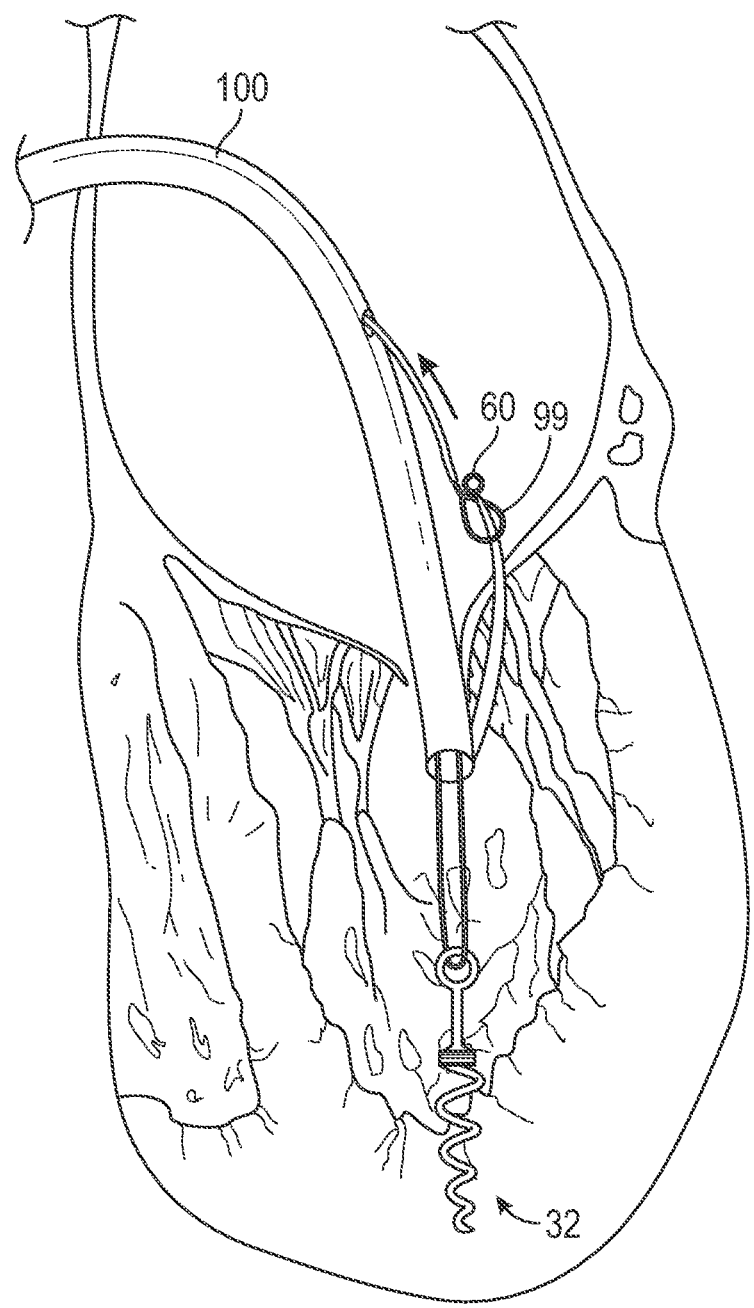
FIG. 31 illustrates the suture loop closed around the suture loop and the suture being withdrawn proximally through the catheter.
Figure 32:
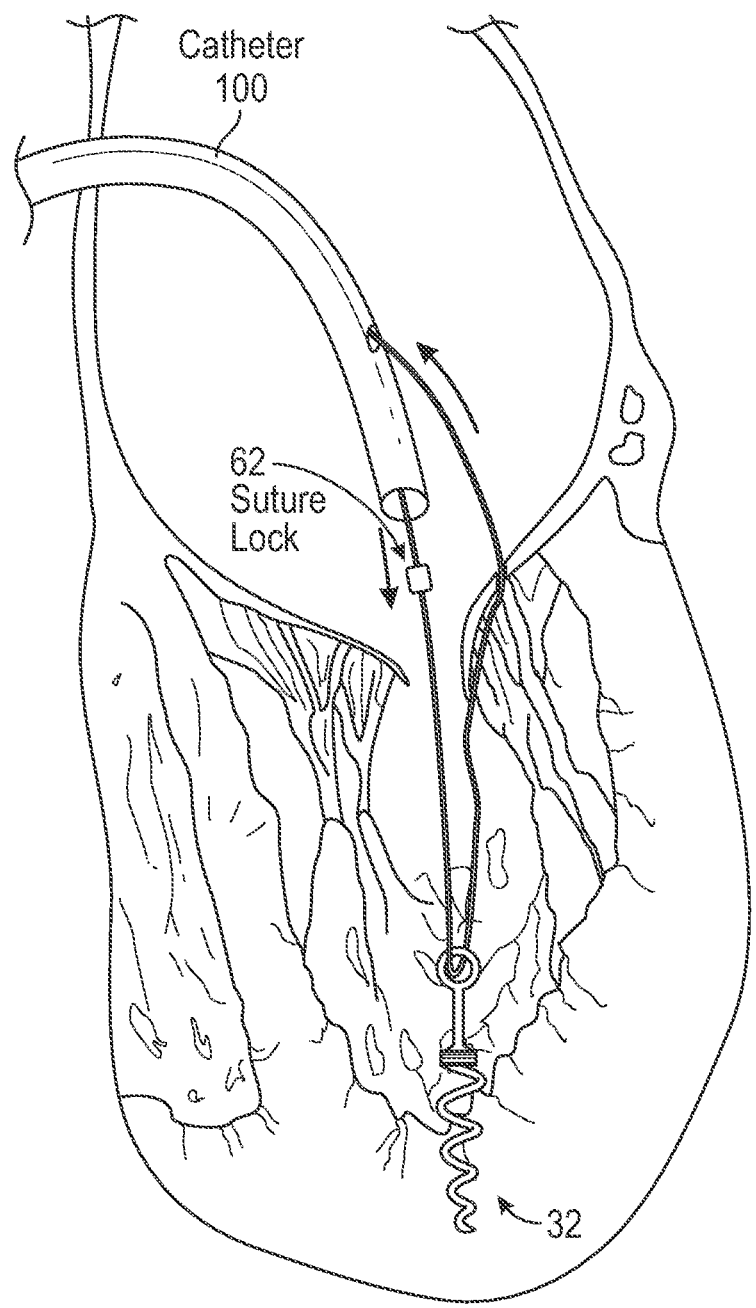
FIG. 32 illustrates the catheter to deliver a suture lock to the backside of the mitral leaflet as the suture is looped around the pathway including the distal apical anchor
Figure 33:
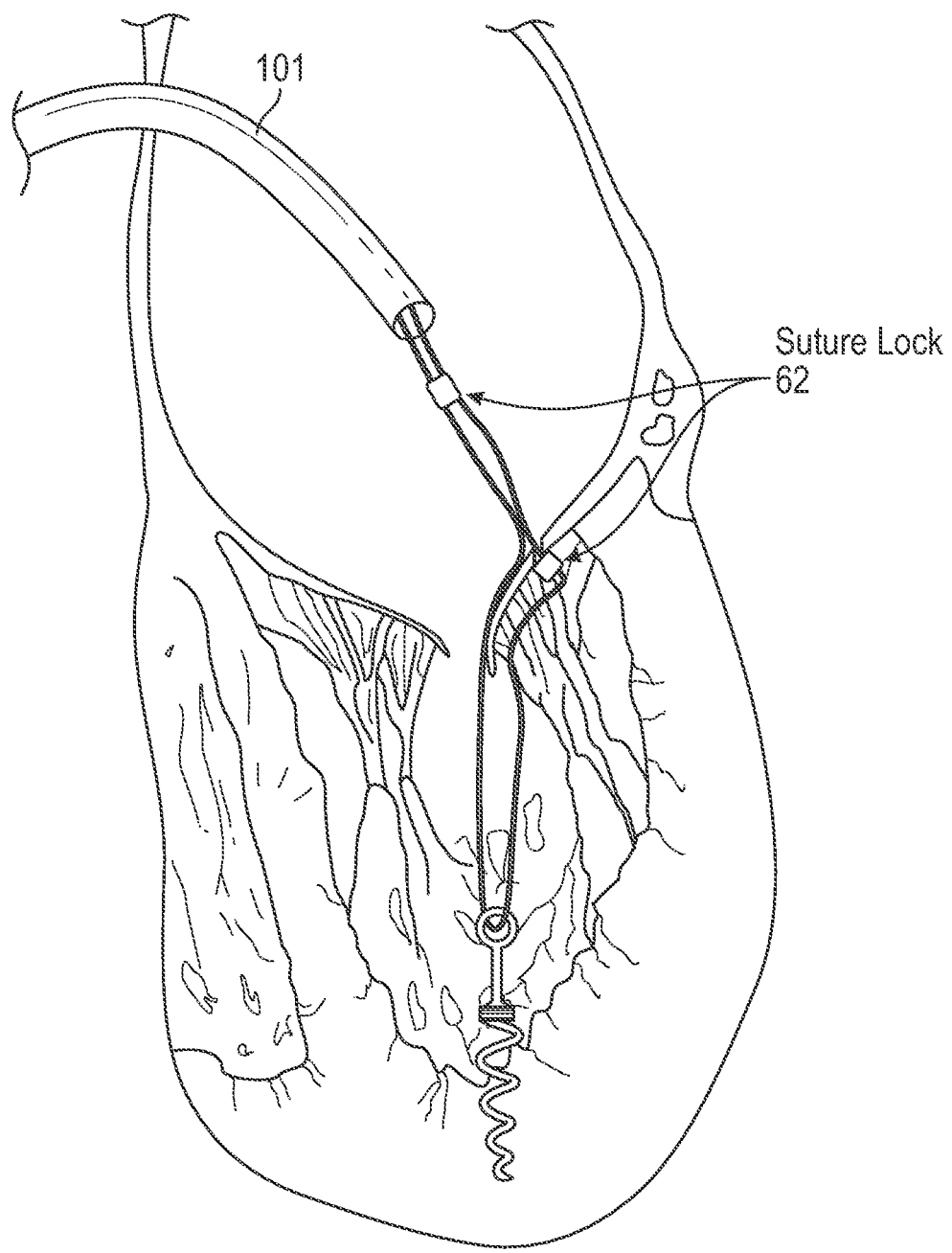
FIG. 33 illustrates a second catheter to contain the suture ends to deliver a suture lock over both leaflets locking the suture together after proper tensioning of the two ends.
Figure 34:
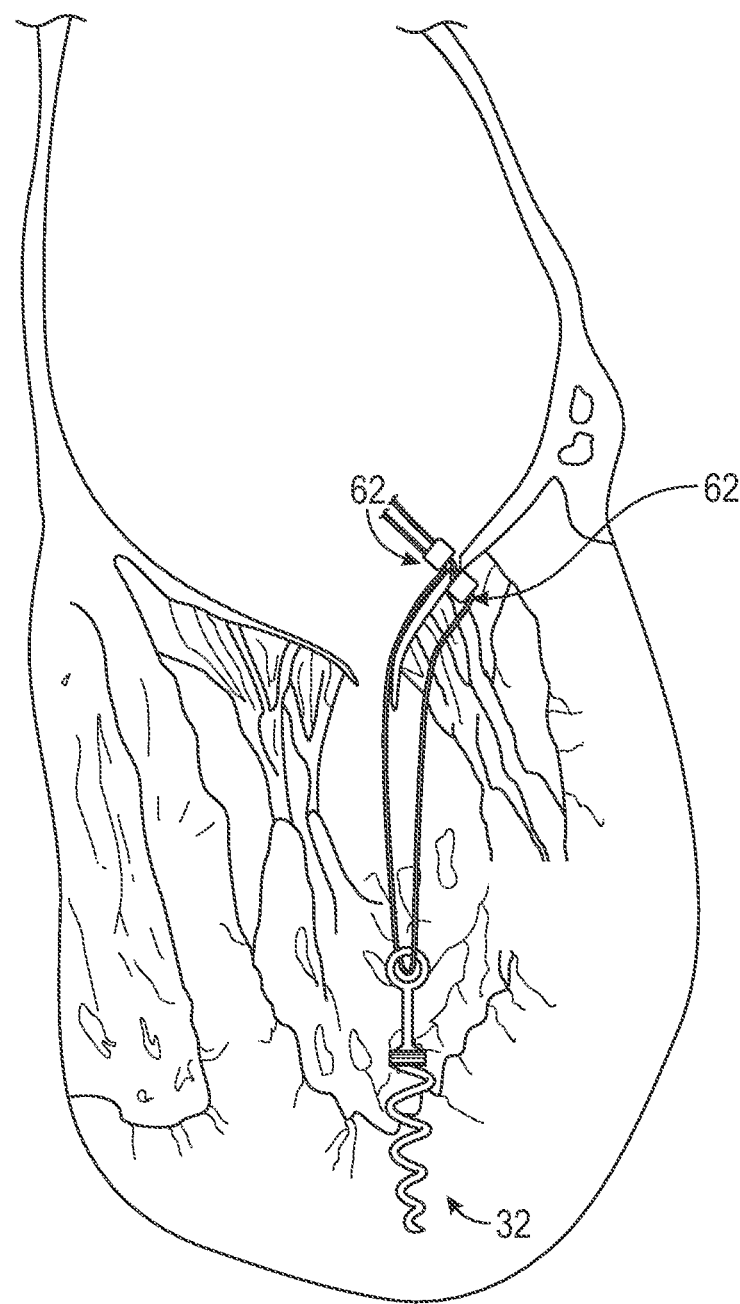
FIG. 34 illustrates the final position of the suture locks in position above and below the mitral leaflet and the suture ends cut to leave a final implant of a distal apical anchor connected to the mitral leaflet.

FIG. 25 illustrates an example of a distal apex anchor 32 constructed of a stainless tube 73 and a silicone anchor plug 72 //to limit the suture movement before delivery of the suture lock 62 for final positioning. The materials can be varied and changed to accommodate size and material enhancements FIGS. 26-34 illustrate an embodiment in which order of the placement distal apex anchor 32 can be modified. As shown, FIG. 26 shows a catheter 100 penetrating the septum 12 from the right atrial and the left atrium 14. FIG. 27 illustrates an anchor 32 being rotated into the left ventricle. FIG. 28 illustrates the distal apical anchor 32 in place with the suture lines 22 attached and extending back through the catheter 100 and an extension arm 94 exposed to capture the mitral leaflet 24 with a needle to be fired when properly positioned on the leaflet 24. FIG. 29 illustrates the extension arm 94 in contact with the mitral leaflet 24 and the needle 96 connected to a suture loop 60 penetrating the leaflet 24 to expose a suture loop 60 on the atrial side of the mitral leaflet 24. FIG. 30 illustrates the suture loop 60 exposed on the atrial side of the leaflet penetrating through the mitral leaflet to accept a loop-snare 99 for capture of the suture loop 60 and retrieval back through the catheter 100. FIG. 31 illustrates the suture loop snare 99 closed around the suture loop 60 and the suture being withdrawn proximally through the catheter 100. FIG. 32 illustrates the catheter 100 delivering a suture lock 62 to the backside of the mitral leaflet as the suture is looped around the pathway including the distal apical anchor 32. FIG. 33 illustrates a second catheter 101 to contain the suture ends to deliver a suture lock over both leaflets locking the suture together after proper tensioning of the two ends. FIG. 34 illustrates the final position of the suture locks 62 in position above and below the mitral leaflet 35 and the suture ends cut to leave a final implant of a distal apical anchor connected to the mitral leaflet 24.

Chordal end termination and suture locking configurations and devices can include a one or more of knots, pledgets or other termination techniques to reduce the focal stress at the attachment points. Piercing through annular tissue and leaflets can be achieved via sharpened needle insertion and driven via steerable catheter and core shaft to push, locate and drive the needle through the mitral leaflet as guided under fluoroscopy or echo guidance. Leaflet location and isolation can be achieved by a mechanical technique of grasping or pinching the leaflet or by suction or freeze-grabbing with a cryo-catheter. These techniques would include a cryo-catheter used in ablation procedures to freeze the focal tissue as described, for example, with reference to FIG. 12. These cryoablation-catheters used for atrial fibrillation often attach themselves to the mitral leaflets accidentally and need to be deactivated to release the attached leaflets. This same cryo attachment could be used to locate and isolate the leaflet in question for a reinstallation of the repair. The cryo catheter uses a gaseous exchange (NO or Argon) to drop the temperature of the tip of the catheter to as low as minus 75 degrees Celsius.

The lower apical anchor construction could consist of a coiled distal section to rotate into the apex of the left ventricle with a round or flat wire construction or a laser cut tube emulating a cork screw similar to a wine cork as described for example in FIG. 6 and FIG. 15. A variable pitch in the screw will allow for a more secure attachment into the surrounding tissue. Another device for tissue securement could include a swaging or ovalization of the screw anchor to achieve the same securement. The attachment to the anchor riser could be pinned, welded, or joined though other mechanical devices. Alternatively it could be constructed of the same material and laser cut from the same tube of stainless steel, Nitinol or other implantable material. At the proximal most end could be a loop or tube to receive the replacement chord such as illustrated in the connection 72 of FIG. 15 or a plurality replacement chords could be preloaded ready for delivery and extending out the handle of the catheter.

In another embodiment the distal anchor could be delivered to the apex of the left ventricle with a plurality of replacement chords looped to the anchor and the extending back to most proximal handle section of the catheter. This would allow for a delivery of multiple anchors to a single point of origin extending vertically from the apex of the left ventricle and the free ends of the replacement chord would be extended back out of the delivery catheter for access advancement of other tools for locking and cutting. Over these free ends a delivery piercing element or tube can be advanced to the mitral leaflet to pierce through and deliver a pledget or restraining element through and to the back side (ventricular side) of the leaflet. This could secure a loop and restraining element to hold the loop from being pulled through the leaflet and acting as a strain relief element. Over the same free end of the replacement chord can be delivered a locking element to hold the position of the chord and pledget securely to the leaflet position. Once delivered this free end can be cut. Finding and holding the leaflet can be achieved by the cryo-catheter to hold the leaflet from the atrial side or a gripping tool to grasp the leaflet from the free edge could also be used. Once the first piercing and pledget is delivered the other free end now can be tensioned around the distal apex anchor and a second locking element can be delivered to hold position relative to the end of the apex anchor. The chord or suture anchor can be secured by an interference fit to the distal apex anchor and or to the other chord line running up to the mitral leaflet. Its important to note the drawings illustrate the delivery and installation of the mitral leaflet anchor to the posterior leaflet but anchors and replacement chords could also be delivered to the anterior leaflet or any position on the mitral leaflet including the free margin, coaptation zone, or annulus.

Another method would be to place the distal rotational anchor in the left ventricle that is connected to a continuous loop of suture similar to a rubber band. One end would be secured to the distal anchor and the other end would pierce the mitral valve leaflet and connected to a strain relief element to distribute the force on the ventricular side of the mitral leaflet from pulling the replacement chord through or tearing the leaflet. The strain relief element could be a laser cut tube that expands from a small configuration to a larger configuration once passed through the leaflet either through a compressive axial force or be constructed of a memory metal like Nitinol where it is pre-set to a shape where the delivery diameter is small and the delivered diameter expands to a larger state. The delivered diameter could be about 0.5 millimeters expanding into about 2-3 millimeters in diameter and have a length of about 2 to 5 millimeters at delivery shortening to about 1-2 millimeters. It could also be constructed of memory metal and set to a round shape similar to an Amplatz device or a simple or complex suture knot located on the ventricular side of the leaflet. Another configuration could be a wound looped Nitinol wire that would look like a daisy with Nitinol wire peddles. This device could also be used to adjust the final length of the loop chord by winding or coiling the loop end passed through the leaflet. This winding mechanism could also be located at the distal coil anchor located in the left ventricle. The adjustment could be actuated during delivery to adjust the chord length and or post procedure where the adjustment is accessed and either shortened or lengthened. A rotational ratcheted drive coupled to a drive shaft or wire could be rotated external to the body by coupling and decoupling when adjustment is needed. The drive shaft could be a round wire constructed of stainless or Nitinol where a hex coupling interface between the drive shaft and winding mechanism could be used to engage and disengage the two elements. The two could be delivered mated to one another for actuation and could later couple by using a loop snare to grasp the winding mechanism and couple the drive shaft engaging the hex drive device. The winding mechanism could utilize a simple rotational spool with a cog-style stop for anti-rotation or a friction resistance to hold the tensioned position. Alternatively, designing the distal coil anchor to accept an inner matching pitch adjustment screw, which would be coupled to the chord and allow for the outer body of the distal anchor to be driven into the apical tissue and secondarily a rotation of the inner matching pitch screw would allow for a tensioning of the chord by shortening the relative distance between the two screw elements. The simplest configuration would be a coil inside another coil where they both have right or left-hand threading and would couple with one another to provide a rotational motion into a translational or axial motion. Locking the two coils together post adjustment would provide for a positive location of the chord length between the leaflet and the distal anchor system.

Patient Selection

In an embodiment, the method of treating a patient begins with selecting an appropriate patient. Preferably the patient includes at least one three or five of the following characteristics from a first group:

Diagnosed with primary or degenerative mitral regurgitation.

Diagnosed with secondary or functional Mitral Regurgitation.

Diagnosed with Mixomotous Mitral Regurgitation.

Diagnosed with a flail leaflet, ruptured chordae, or leaflet prolapse.

Mitral regurgitation grade 1 or more; 2 or more; 3 or more or; 4 or more.

Annular diameter from A2 leaflet to P2 leaflet at least 5, 10, 15, 20, 30, 50 mm less than sum of length of P2+A2 leaflet. Or similar mathematical relationships that ensure adequate redundant coaptation after repair, so as to create a durable repair.

Annular diameter from A2 to P2 leaflet 10 to 50 mm, or preferably 24 to 36 mm, most preferably 26 to 33 mm Access vessel diameter at least 2-10 mm diameter Preferably the patient has at least 1, 3, 5 of the following characteristics from a second group:

Evaluated by a heart team including at least one and preferably two cardiac surgeons and determined not to be an appropriate candidate for conventional open surgical repair.

STS predicted operative mortality (STS Score) of 2-20 or greater

Patient was offered and refused open surgical repair

Age between 18 and 90, or preferably between 35 and 85 more preferably between 40 and 85.

Patient will not accept blood transfusion.

Prior open chest surgery

Ejection fraction of at least 10-60 percent

For some embodiments of the device it is preferably the patient is substantially free from the following conditions Moderate or severe COPD Hypercoagulative disorder Systemic degenerative collagen disease ie Marfans syndrome Prior septal infarction affecting the anchor area.

Ventricular septal defect.

Known allergy to contrast media

Prior mitral valve replacement

In one embodiment the patient selected meets at least 1, 2 or 3 criteria from group and at least 1, 2 or 3 from the second group. In one embodiment the patient selected meets at least 1, 2 or 3 criteria from group and at least 1, 2 or 3 from the second group and does not meet at least 1, 2 or 3 from the third group.

Patients can be screened using echocardiographic imaging and or CT imaging. MRI imaging is also possible. Preferably a contrast gated cardiac CT with at least 32, 64, 128 slices is obtained prior to the procedure and used for patient selection and or case planning. Using imaging software the annular diameter is measured from the hinge point of A2 to hinge point of P2 leaflet, and the free length of the leaflet is measured. These measurements are compared to ensure that after the procedure is completed sufficient redundant coaptation will be present to produce a durable repair. In one embodiment the annular dimension is reduced using another device or method such as a trans-catheter annuloplasty device, to create a small enough annular diameter.

Imaging

The present disclosure has the potential to allow excellent real time assessment and adjustment of suture placement and tension during the procedure. Some embodiments of the imaging method offer significant advantages in visualization even compared to what is available during open cardiac surgery.

Optimize Tension

During Open surgical mitral valve repair, the heart is stopped, flaccid and deflated, the surgeon has to estimate the movement of the dynamic structure based on his experience. The surgeon's initial assessment step involves filling the ventricle with saline to push the mitral leaflets closed and visually asses areas of leakage, prolapse or inadequate coaptation.

This assessment is limited because it is not performed on a beating heart, but the sutures are tied off and secured based on this assessment, then the atrium is closed the heart is reanimated, and the final echo assessment on the beating heart is performed. If an issue is identified, the surgeon needs to stop the heart again, reopen the atrium and modify the previously completed repair. Because the sutures are knotted and trimmed they cannot simply be re-tensioned and so are typically replaced or additional artificial chords added. In some embodiments of the present disclosure real time echocardiographic assessment is possible as the suture tensions are being adjusted individually.

In one embodiment the method for implanting the artificial chords includes the following steps; first securing one end of a plurality of artificial chord to a leaflet of the mitral valve or annulus of the surrounding tissue and the other end to an anchor point mechanically connected to the left ventricle; Second adjusting the tension of the artificial chords while viewing an echocardiographic image of the mitral valve.

In some embodiments of the method described above the echocardiographic image includes color Doppler assessment of velocity and or flow. In some embodiment the echocardiographic image includes real time 3d or 4D echo. In some embodiments the color flow Doppler and 3D images are fused or combined. In some embodiments the Echo probe is placed through the patient's esophagus in some embodiments the echo probe is a surface probe on the patient's chest, and in some embodiments the echo probe is within the patient's vascular system.

In some embodiments at least 1, 2, 3, 4, 5 of the functions below are confirmed under echocardiography as the artificial chords are being tensioned, in another embodiment after the artificial chords are tensioned but before the chords are permanently disconnected from the delivery system, where this may allow simplified re-tensioning if necessary.

Free from Systolic anterior leaflet motion causing obstruction or restriction of Left Ventricular Outflow Tract Mitral valve gradient Appearance of regurgitant jets, Velocity of regurgitant jest Length of regurgitant jets MR grade A minimum leaflet coaptation distance of at least 3, 5, 9, 12, 15 mm is achieved throughout the line of coaptation Degree of leaflet prolapse, measurement of the height that a portion of the mitral leaflet moves above the plane of the mitral valve Areas of "smoke" or stasis within the atrium ventricle or atrial appendage Shunting between left and right ventricles especially at ancho locations or other turns septal sections Additionally during the assessment period after initial tensioning of the sutures and before disconnecting the sutures from the delivery system, or before trimming off excess suture, while suture tension is easily read adjustable, at least 1, 2, 3, 4, 5 of the following are assessed.

Blood pressure

Cardiac output

ACT Actual clotting time

EKG electrocardiogram

Cardiac enzymes ckmb and troponin

Patency of coronary arteries

Fluoroscopic evaluation of ventricular shunt potentially from anchor or trans ventricular access.

Floroscopic appearance of ventricular anchor

Flouroscopic position of delivery system

Atrial pressure or wedge pressure

Oxygen content of patient's blood

After the assessment step is completed based on the information obtained from the measurements the physician or team decides to make the results permanent or to readjust the tension, add additional repair components or abort the procedure. In some embodiments the physician also has the option to remove the entire implant, in other embodiments the physician has the option to remove the artificial chord portion of the implant but the ventricular anchor remains implanted. In some embodiment the assessment step is further augmented by including a stress echo component where drugs such as pressures are given to the patient to adjust the heart rate, cardiac output and ventricular pressure to further assess how the repair functions in different hemodynamic conditions.

Monitoring

During the procedure the patient is preferably under conscious sedation. This makes Trans Esophageal Echocardiography more challenging, but minimizes anesthesia risk and allows patients to go home more quickly. With general anesthesia or conscious sedation during the procedure standard cath lab monitoring procedures should be performed including arterial pressure, EkG ACT blood gasses etc. Additionally wedge pressure or Left atrial pressure may be useful for this procedure. For this procedure careful monitoring of arterial pressure provides an early indicator of damage to the mitral valve apparatus, entanglement of the device in Chordae, or damage to the septal wall. Measuring left atrial pressure may provide a simple quantifiable measure of improvement in mitral function without the challenges associated with getting the appropriate echocardiographic view.

Access

A blood vessel is accessed through conventional methods standard in interventional cardiology, preferably the vessel is a vein. In one embodiment the vessel is the femoral vein, in another embodiment the vessel is the radial brachial or subclavian vein. Access may be by cut-down or percutaneous needle stick. In some embodiments the vessel is prepared for closure by pre-insertion of a vascular closure device such as Percolse or Prostar (Abbot Vascular)

A guidewire is advanced, optionally using a guide catheter, through a valve into the right ventricle. The device of the present disclosure can be advanced over the guidewire to a position near the apex of the ventricle.

A sharp curve is created at the tip of the device. The curve is oriented so that the exit lumen points towards the septal wall of the heart. The radius of curvature of the fully curved system is preferably less than 3-30 mm, and the curvature is preferably positioned less than 5-50 mm from the tip of the system.

In one embodiment this curve is created using a steerable catheter. The preferred embodiment of a steerable catheter incorporates a pull wire that when pulled creates the inner radius of the catheter. Some embodiments also include a coil a braid and or an axial reinforcement.

In another embodiment the curve is created using coaxial sheaths with different shapes. For example an outer sheath substantially straight or with a large radius of curvature near its tip combined with an inner sheath with a small radius of curvature at its distal tip. By advancing the inner sheath out of the outer sheath the tip of the catheter creates the desired curve. By advancing the more curved sheath further a greater curved angle is obtained.

In some embodiment the sheaths have different relative stiffness' s at different points in their length. In the preferred embodiment the outer sheath is curved to access the apex of the ventricle and stabilize through the vena cava, the shape that enables this is 7 to 50 cm back from the distal tip of the sheath. The inner sheath is substantially more flexible (less than 30, 50, 70, 90% the bending stiffness by ASTM three point bend test) than the outer sheath in the range 7 to 55 cm from its distal tip, this enables the inner sheath to move relative to the outer sheath without substantially changing the orientation of the outer sheath in the heart and vena cava. The distal portion of the inner sheath is preferably stiffer than the previously described section, and stiff enough that as it is extended out of the outer sheath it assumes its approximate shape despite contact with the structures of the heart.

The device is oriented so that the exit of the catheter is near the Right ventricular apex, pointing into the septal wall and preferably upwards towards the mitral valve. The position of the sheath is confirmed by imaging. A four chamber echocardiagraphic view is used in some embodiments, a short axis mitral view is used in other embodiments. Fluoroscopic imaging is used in some embodiments. Depending on the location of the area in need of repair the desired puncture site can be selected and the appropriate angle based on the planned orientation of the replacement chords.

In some embodiments a puncture higher up closer to the papillary muscle insertions and away from the ventricular apex is preferred, this location provides the benefit that as the heart remodels and the ventricular volume is reduces to more normal physiological levels the tension in the chords will change less than with a near apical attachment.

A needle and or dilator is advanced through the sheath or sheaths and through the septal wall of the heart. In the preferred embodiment a needle and dilator are used together. Both the needle and dilator are pre-shaped with curvature near their distal tip to ensure the needle stays within the left ventricle and avoids the mitral valve apparatus. Presence of the needle in he left ventricle may be confirmed with echocardiography, fluoroscopy and or by the presence of red (oxygenated) pulsatile blood at the proximal end of the needle.

After ventricular access is gained a guidewire is advanced across the septum. In some embodiments the guidewire is further advanced across the mitral valve into the atrium, and in some embodiments further into a pulmonary vein. The wire is confirmed not to be tangled in the mitral apparatus using echocardiography and wire manipulation. In some embodiments a device such as a balloon or sheath is advanced over the wire to confirm the wire does not pass through the chordal structure.

Ventricular Anchor

The present disclosure include several embodiments of ventricular anchors.

In one embodiment the ventricular anchor is similar to an Amplatz septal occluder (ST Jude Medical) consisting of a braided section that expands on both sides of the septal wall.

In another embodiment the anchor is a barbed stent-like structure intended to be deployed within the ventricular wall. The stent structure may be self-expanding or mechanically ie balloon expandable and may include barbed anchors similar to those found on stent grafts such as Endurant (Medtronic)

In another embodiment the anchor is a flanged covered stent where the Right ventricular side opens into a substantially flat configuration oriented in a plane substantially perpendicular to the axis of the stent.

In another embodiment the Flange is constructed from a ring around the circumference of the flange and the flange itself a layer of fabric. The flange can be collapsed into an elliptical shape and delivered through the lumen. The ring may be constructed from nitinol titanium stainless steel or a cobalt chrome alloy. A fabric lumen extends through the center of the flange and into the trans-septal puncture. After chord implantation tension to snug the flange against the septal wall is provided through the chords in some embodiments. During the procedure a portion of the delivery system can be used to push the flange against the septal wall. In other embodiments the fabric sleeve incorporates and anchor such as a stent or a barb to stabilize it within the septal wall.

The ventricular anchor is deployed over a guidewire. After the anchor is deployed the chord delivery anchors and their delivery system can be delivered through the ventricular anchor and over the guidewire.

Positioning

Identifying the correct place to place the new chords is performed substantially using echocardiography. The area of a regurgitant jet or a leaflet prolapse or flail can be identified using 2d or 3d echo and or color flow Doppler. Preferably a combination of these imaging modalities is used.

The device to deliver the chords is advanced across the septal puncture. In some embodiments the same steerable or shapeable system used to create the septal puncture is advanced across the puncture. In other embodiments it is a separate device that can pass through the other sheaths.

The position of the distal tip of the device can be oriented relative to the mitral structure as follows. Biased more anterior by increasing the curvature of the system where it passes into the Left ventricle through the septum. Biased more posterior by decreasing the curvature of the system where it passes into the Left ventricle through the septum. Biased from commissure to commissure by rotating the curved portion that passes through the sheath. Biased atrially by extending or ventricularly by retracting the distal portion of the device.

Primary

To replace primary chords, the chords located near the free edge of the leaflet, several methods of engaging the mitral leaflet are possible. The bulky knot system used by Harpoon Medical is is used in one embodiment. The looped suture used by Neochord Inc is used in another embodiment. Both these methods appear to work well in early clinical experience. The preferred embodiments intend to replicate the clinically proven suture tissue interfaces that have been developed in the open surgical experience.

Another embodiment may use a bifurcated catheter. One side of the catheter engages under the leaflet this side can be pushed on to help identify the area of the leaflet where the suture will pass. The other side passes into the atrium. A needle or pair of needles puncture the leaflet from the first side of the catheter and a snare captures the needles or the suture from the needles from the second side of the catheter. In some embodiments a loop end of the suture is passed over the snare such that when the needle end of the suture is pulled back through it forms a girth hitch. In other embodiments the loop end of the suture is twisted and doubled over twice forming a knot known a prusik or double girth hitch.

Secondary

To replace secondary chords, those that are located farther back from the free edge of the leaflet, some of the devices and methods described to replace primary chords need adaptation. The bulky knot anchoring method is appropriate for replacing secondary chords without modification.

The bifurcated catheter method is appropriate for replacing secondary chords with a minor adaptation to allow the snare side to puncture the leaflet.

Resect Like

During mitral valve repair surgeons often resect some of the leaflet tissue. A similar effect can be created using the bifurcated catheter system described above. By placing suture through a section of leaflet and gathering the tissue together as the suture is tightened a similar effect can be achieved. The suture can be noted close to the leaflet to only resect, or extended and used as a new chord as well.

Partially Annuloplasty

In some cases it may be desirable to use the dual puncture method into the annulus close to the hinge point of the leaflet to create a result similar to a surgical suture annuloplasty. In some embodiments a series of suture loops are created encircling the entire annulus. In some embodiments suture loops are created only in a safe area away from the aortic valve, coronary arteries and conduction pathways. In some embodiments the suture loops are created in the areas where the heart is most likely to dilate, ie in an area of prior infarct, or in an area near the mitral commissures.

Assessment

After one or more repair sutures are placed into the mitral structure, the result may be assessed. Tension is applied selectively on each artificial chord until the desired leaflet motion is achieved. Preferably a target coaptation height is achieved by echocardiography. In some embodiments, as too much and too little tension are balanced the sutures are slightly over tensioned to allow some remodeling to occur.

Knotting

In one embodiment the sutures are knotted on the right ventricular side of the anchor using a crimpable knot large enough to prevent the crimped knot from passing through an opening in the anchor.

In another embodiment the artificial cords are crimped directly to a suture-sewn or tied to the anchor.

Suture Adjustment n some embodiments the artificial chord tension can be adjusted in a similar procedure. In the preferred embodiment this can be achieved entirely from the right ventricle without re-crossing the septum. In one embodiment the crimpable knots are snared, pulled away from their base and twisted. The twisting motion of the suture of pair of sutures forming the artificial chord effectively shortens it. In another embodiment the crimp knot is snared, pulled and additional crimp knot placed over it.

Multiple Systems

In some embodiments it is possible to attach up to 1 to 10 artificial chords to a single septal anchor. In some embodiments more than one ventricular anchor is used, either to optimize the direction of pull of the chords, or to minimize the load on the septal anchor Alternative Methods For some patient anatomies it may be necessary or desirable to anchor the chords to a different area of the LV rather than the septal wall. In one embodiment the anchoring location is at the papillary muscle. Preferably the suture attachment to the papillary muscle or ventricular wall is made by creating a figure of eight suture, as is commonly done by surgeons during open chordal replacement. This type of anchor can be placed by a trans-catheter method through the trans-septal ventricular puncture described above, or can be placed through a more conventional atrial trans-septal puncture. One embodiment of the system as adapted to suture to papillary muscles is a simple change to the bifurcated leaflet suturing system where the needle and snare ends are curved inward towards each other so that when actuated they can place a suture through a papilay muscle. In another embodiment the ventricular anchor is a cork screw shaped anchor similar to an Aptos Endovascular staple (Medtronic Inc) or any of the configurations used to secure pacemaker leads.

Bailout

In some embodiments the ventricular anchor is retrievable. One example is a recapturable self-expanding stent, or an Amplatz like device.

In some embodiments artificial chords are retrievable through a hemodynamic assessment period. In one embodiment this is achieved by pulling both ends of the suture for assessment, prior to engaging the girth hitch for permanent implantation Concomitant Repair Rings Alfieri In some embodiments the procedure is performed in conjunction with another mitral valve repair procedure. This simulates the multiple techniques typically used by surgeons. There are several devices in clinical use that simulate annuloplasty rings such as cardiac dimension coronary sinus based approach, Mitralign and Valtech suture based approaches etc. Additionally Mitraclip (Abbott) simulates an Alfieri stitch, a seldom used surgical technique that creates two orifices.

Device

The preferred embodiment of the device includes and outer sheath that is curved to engage the shape of the vena cava and right ventricle. The proximal end of the outer sheath is connected to the handle of the delivery system. Within the outer sheath is a conventional dilator for gaining vascular access. Once the right ventricle has been accessed the dilator is changed out for a special trans ventricular dilator, with a relatively flexible proximal portion and a stiffer sharply curved distal portion with a short tapered radio opaque tip. The handle has a provision to lock to the dilator preventing both axial and rotational movement. The ID of the dilator allows clearance for a long flexible, preferably hollow needle. In some embodiments the needle is curved. The needle is configured to allow the needle tip to be advanced through the distal tip of the dilator and precisely place the trans-ventricular puncture. In some embodiments the needle is sized to accommodate a 0.009, 0.014, 0.018, or 0.035 inch diameter guidewire. In other embodiments the dilator is advanced through the puncture over the needle and the needle withdrawn. In some embodiments the needle is integral to the dilator and can be retracted within the dilator or extended a limited length past the tip of the dilator, in some embodiments the length is 2 to 20 mm in other embodiments 4 to 40 mm.

Figure 35A:
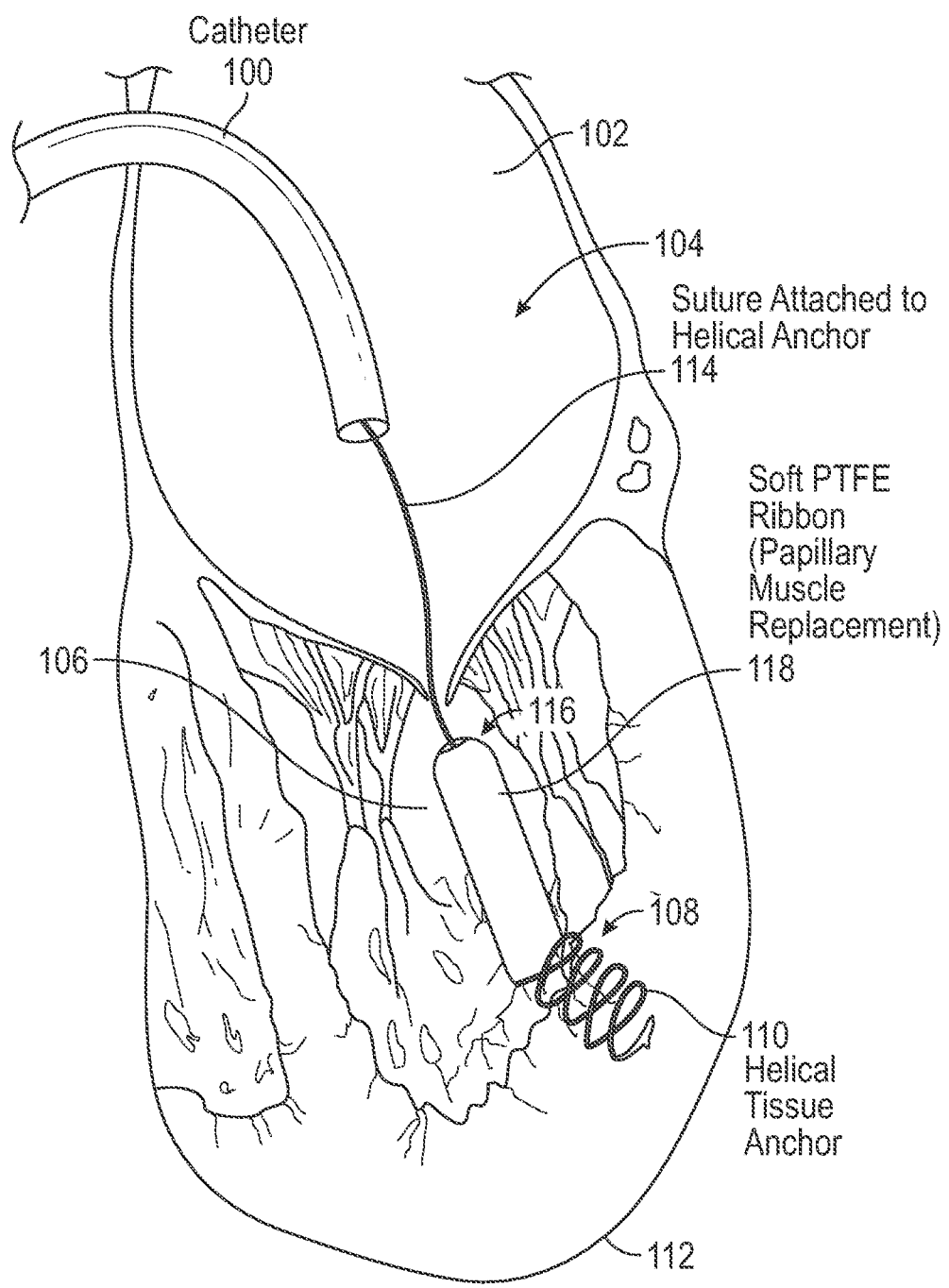
FIG. 35A illustrates attachment of a neo papillary muscle within the left ventricle.

One exemplary application of the foregoing is discussed below, in connection with FIGS. 35 A through 35 O. Referring to FIG. 35A, the distal end of catheter 100 has entered the left atrium 102 via conventional techniques. Catheter 100 is advanced through the mitral valve 104 to the vicinity of the apex 112 of left ventricle 106. A tissue anchor 108 such as a helical tissue anchor 110 is rotated into the muscular wall by an anchor driver (not shown) advanced distally through catheter 100. Thereafter, the catheter 100 and/or anchor driver is proximally retracted to leave the anchor 110 secured to the wall, and attached to an anchor suture 114 which extends proximally throughout the length of the catheter 100. A distal portion of the anchor suture 114 may carry a neo papillary muscle 116 which may comprise a soft ribbon or body 118, optionally approximating the size of a mitral papillary muscle.

Preferably the anchor 108 is attached at a point that is offset from the thin tissue of the apex 112, and is instead implanted in the generally thicker adjacent wall of the ventricle. Positioning the anchor is preferably also such that the longitudinal axis of the implanted neo chord construct is aligned approximately parallel to or concentric with the original path of the native chord.

Figure 35B:
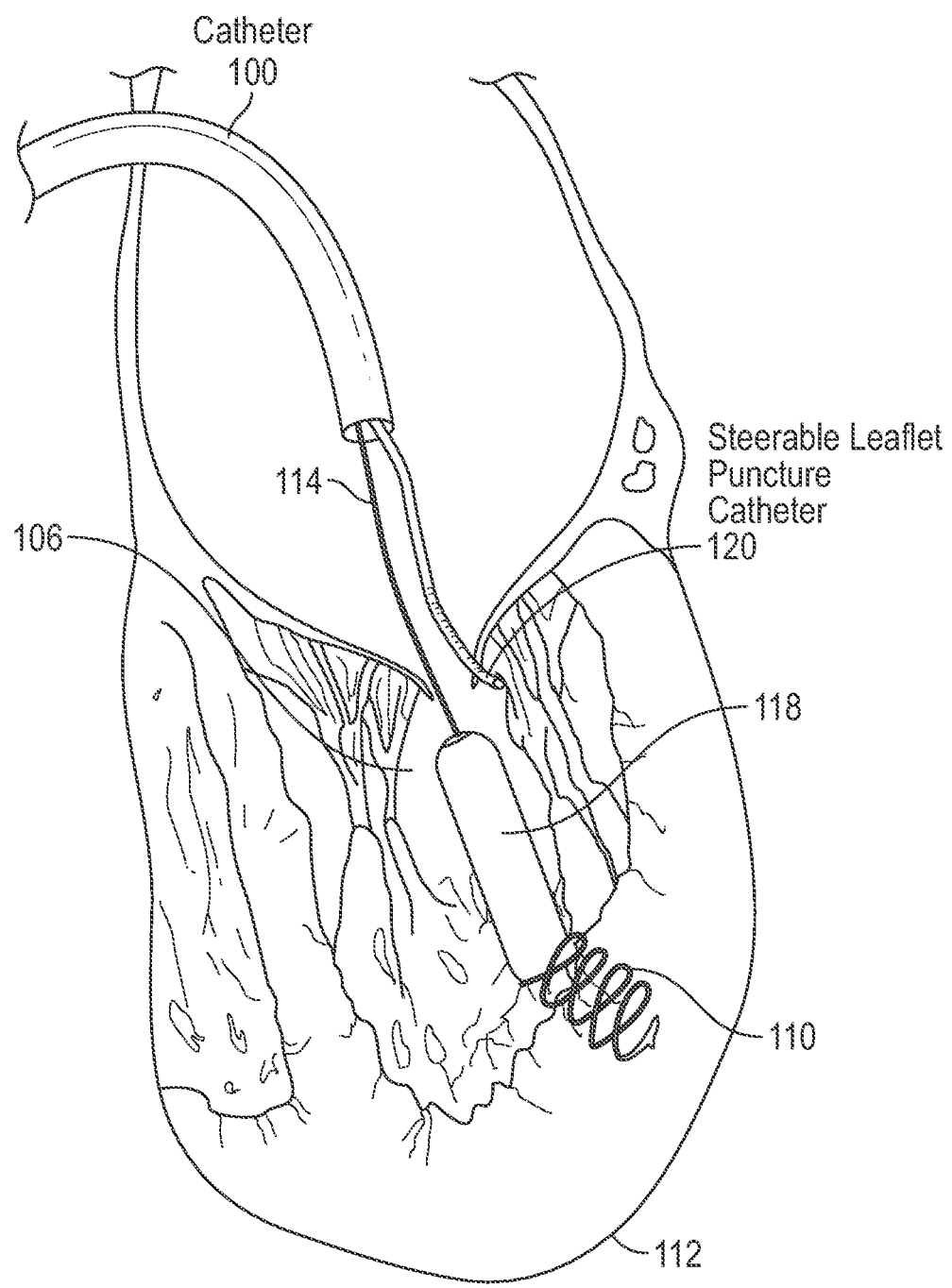
FIG. 35B illustrates a steerable leaflet puncture catheter advancing through the mitral valve.

Referring to FIG. 35B, a steerable leaflet capture catheter 120 is advanced distally beyond the catheter 100, through the mitral valve 104 and into the left ventricle 106.

A distal portion of leaflet capture catheter 120 is provided with a deflection zone 122. Deflection zone 122 may comprise any of a variety of deflection mechanisms. For example, a plurality of transverse slots 124 may be spaced apart along a first side of the catheter 120. A second, opposing side 126 of the catheter comprises an axially incompressible spine. Proximal retraction of one or more pull wires (not shown) causes axial collapse of the slots 124, thereby deflecting the catheter as shown, for example, in FIG. 35C.

Preferably, the deflection zone 122 may be deflected throughout an angle of at least about 160° and preferably at least about 180° or about 190° or more in a simple or compound curve, and have a best fit radius of curvature of less than about 2 cm, and, preferably, less than about 1 cm. In one implementation the shortest linear distance D between the distal tip 128 and the catheter shaft is within the range of from about 0.5 cm and about 1.5 cm and optimally approximately 1 cm, to position the leaflet anchor a desired setback from the leaflet coaptive edge.

Figure 35C:
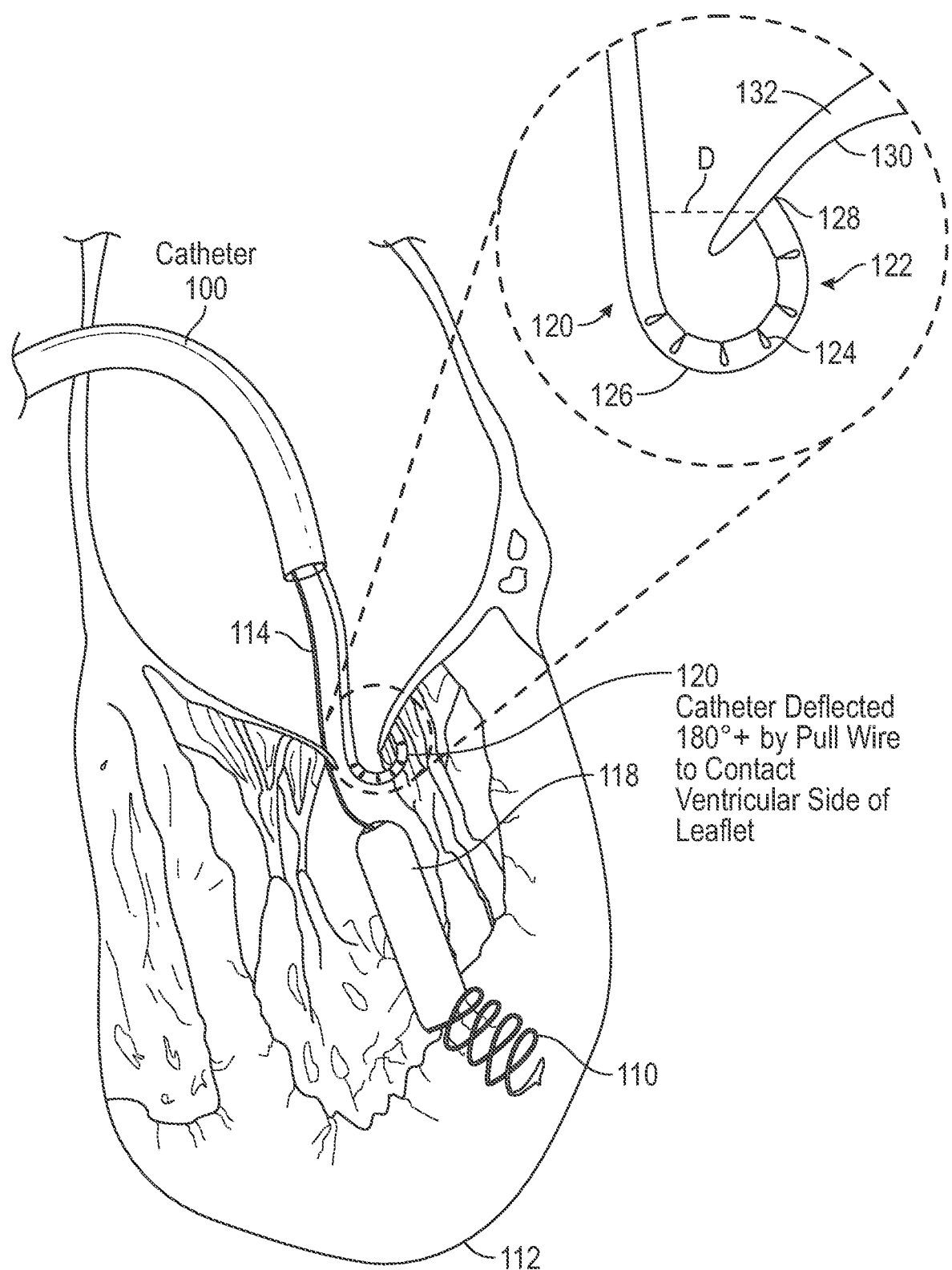
FIG. 35C illustrates the steerable leaflet puncture catheter deflected through an angle of at least about 180°.

The steerable leaflet capture catheter 120 is advanced through the mitral valve 104 and deflected as illustrated in FIG. 35C to position distal tip 128 in contact with a ventricular side 130 of a flail leaflet 132.

Figures 35D, 35E:
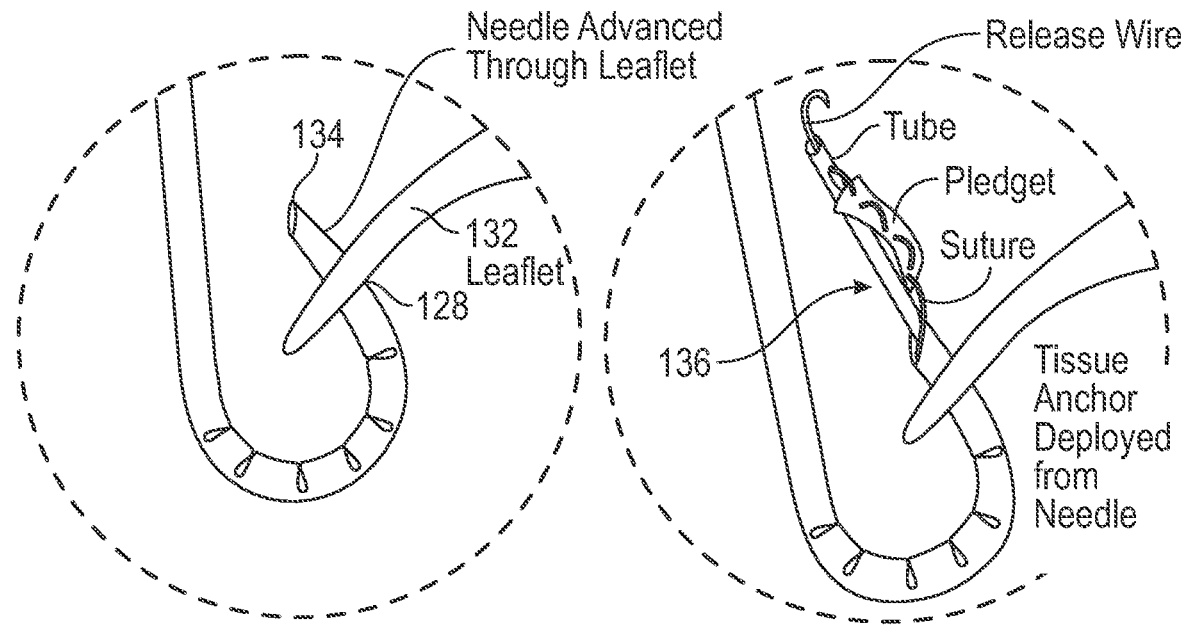
FIGS. 35D through 35G illustrate puncturing the leaflet and deployment of a collapsible pledget type leaflet anchor.

As illustrated in FIG. 35D, a control on a proximal manifold may be manipulated to advance a needle 134 out of the distal end 128 and through the flail leaflet 132. Puncture of leaflet 132 by needle 134 may be accomplished during diastole, when the leaflet 132 is biased in the direction of the left ventricle 106.

Figures 35F, 35G:
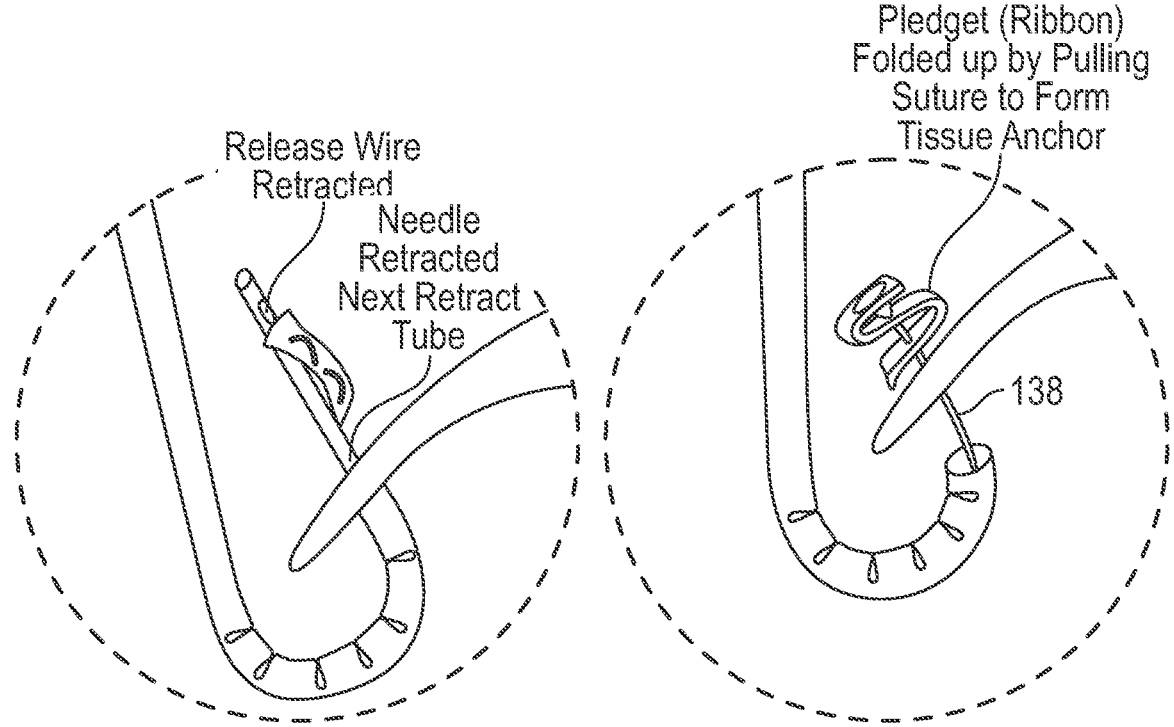

The catheter 120 and/or needle 134 may be utilized to deploy any of a variety of tissue anchors to secure a suture to leaflet 132. In the Illustrated embodiment, a pledget 136 carried by a leaflet anchor suture 138 is deployed from the needle 134 on the atrium side of the leaflet 132. The pledget is in the form of an elongate ribbon, having a proximal end and a distal end. The distal end is secured with respect to the leaflet anchor suture 138. The leaflet anchor suture 138 may be threaded through one or two or four or more apertures in the elongated ribbon. As seen in FIGS. 35E through 35G, proximal retraction on the leaflet anchor suture 138 causes the ribbon to fold and collapse axially, thereby forming a mass of sufficient transverse area that proximal tension on the leaflet suture is insufficient to pull the resulting pledget through the leaflet.

Figure 35H:
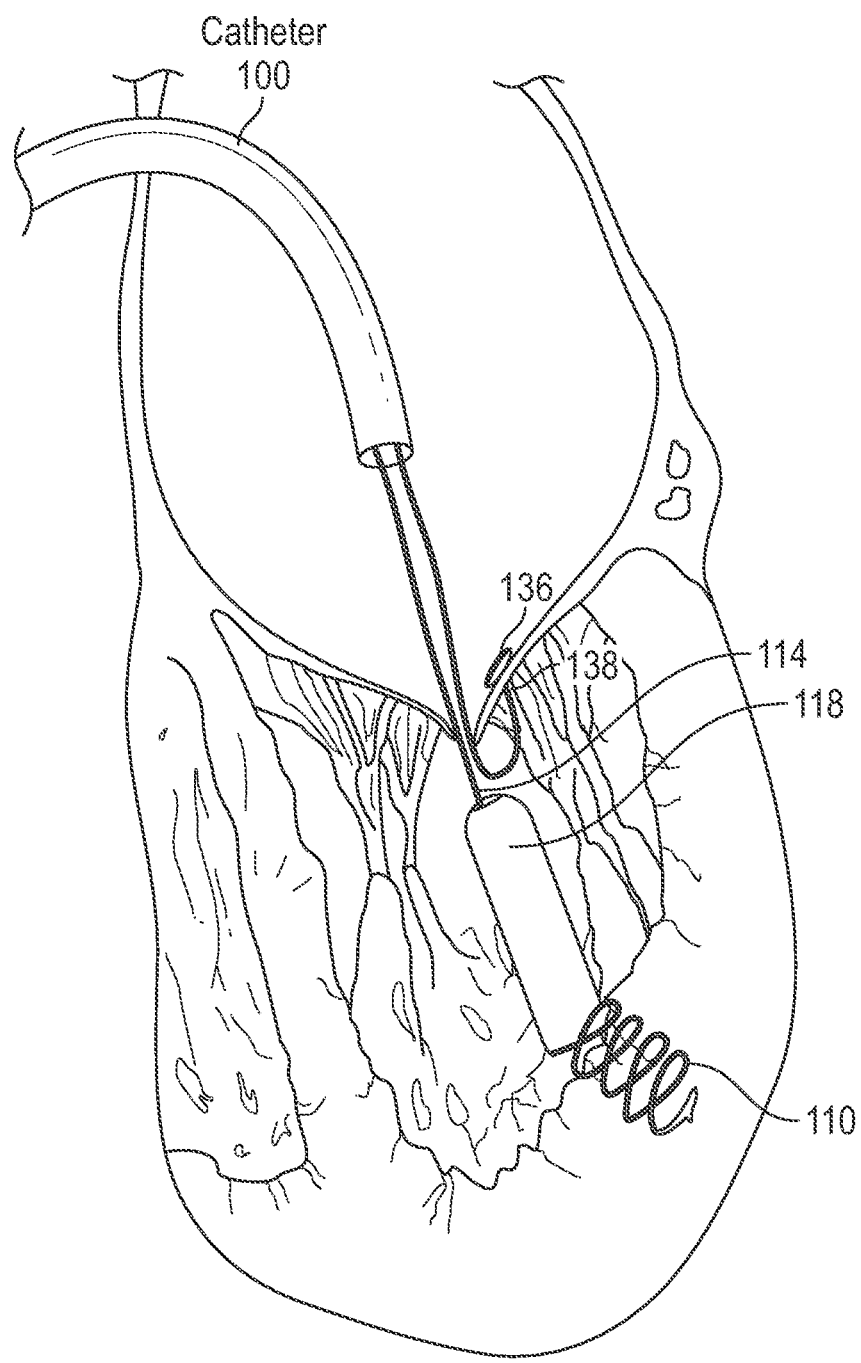
FIG. 35H illustrates a ventricle suture and a leaflet suture extending proximally through the deployment catheter.

The leaflet capture catheter 120 is thereafter proximally retracted, leaving the construct as illustrated in FIG. 35H.

Any of a variety of leaflet anchors may be utilized, generally sharing the characteristic of being laterally enlargeable from a low crossing profile for crossing the leaflet, to a larger transverse profile for resisting retraction back through the leaflet. Lateral enlargement may be accomplished by tilting a T anchor or by active deformation by a control wire or elastic deformation following release from a constraint.

Figures 1, 35I:
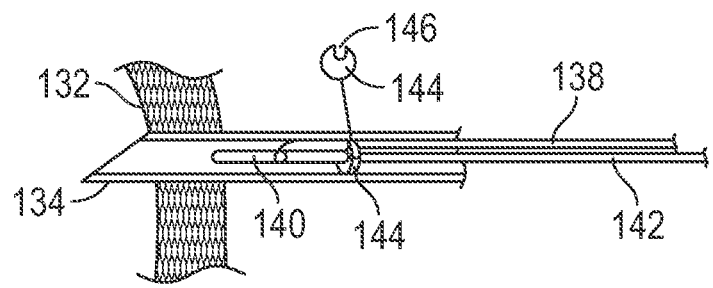
Figures 2, 35I:
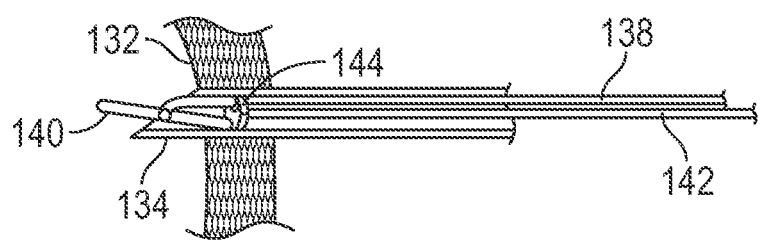
Figures 3, 35I:
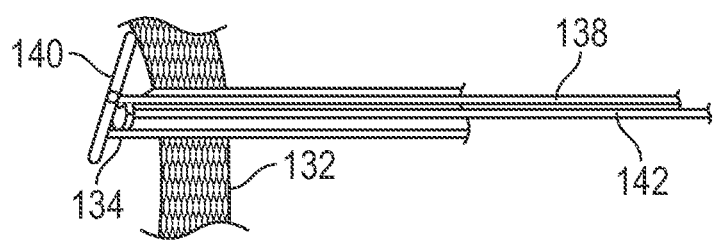
Figures 4, 35I:
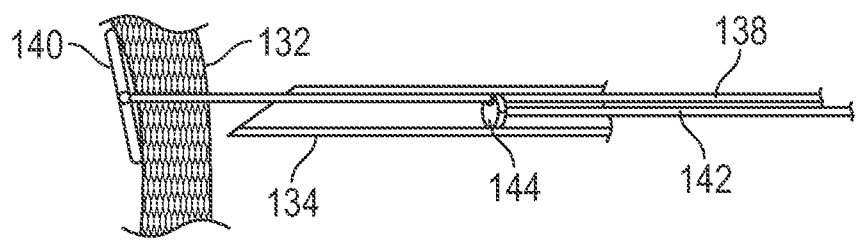

FIGS. 35I-1 through 35I-4 illustrate deployment of a T tag type anchor through the flail leaflet 132. An anchor element such as a single T tag bar 140 secured to suture 138 may be distally advanced through the needle 134 by a push wire 142. Push wire 142 may be provided with a distal pushing platform 144, which may be provided with a cut out 146 for accommodating suture 138. As the bar 140 exits the needle 134, it will rotate about the suture attachment point and seat against the atrium side of the leaflet 132 upon proximal traction on leaflet suture 138. The bar 140 may comprise a single element as illustrated, or an "X" or multi strut construct, depending upon desired performance characteristics.

Figures 1, 35J:
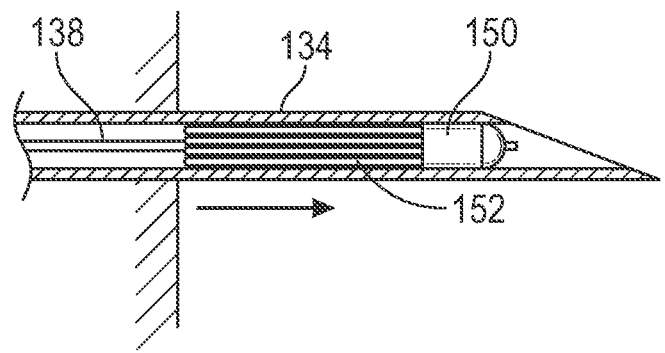
Figures 2, 35J:
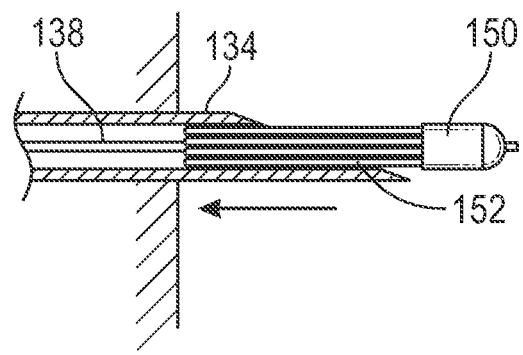
Figures 3, 35J:
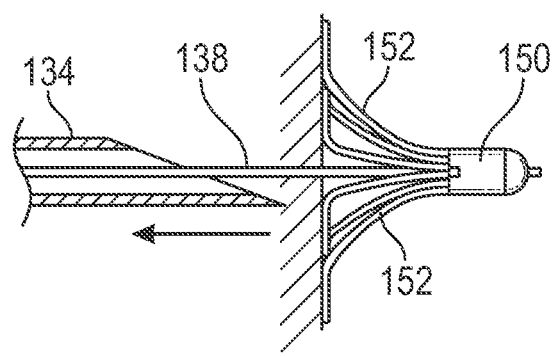

An alternative leaflet anchor is illustrated in the sequence of FIGS. 35J-1 through 35J-3. The tissue anchor comprises a hub 150 secured to the suture 138. Hub 150 carries a plurality of spokes 152 which are enlargeable transversely from a low profile linear configuration when constrained within needle 134, to an expanded configuration illustrated in FIG. 35J-3 for resisting proximal retraction through the leaflet 132. At least two, and preferably four or six or more spokes or struts 152 may be provided, extending radially outwardly from the hub 150 in the deployed configuration, for providing a footprint against the leaflet. The struts may be inclined radially outwardly in the proximal direction to provide a force damper allowing hub 150 to be transiently drawn closer to leaflet 132 in response to tension spikes such as when the leaflet 132 reaches the limit of travel during systole imposed by the implanted neo chord. The spokes 152 and hub 150 may be laser cut from a NiTi tube and adhesively bonded, crimped, or otherwise attached to the leaflet suture 138.

Figure 35K:
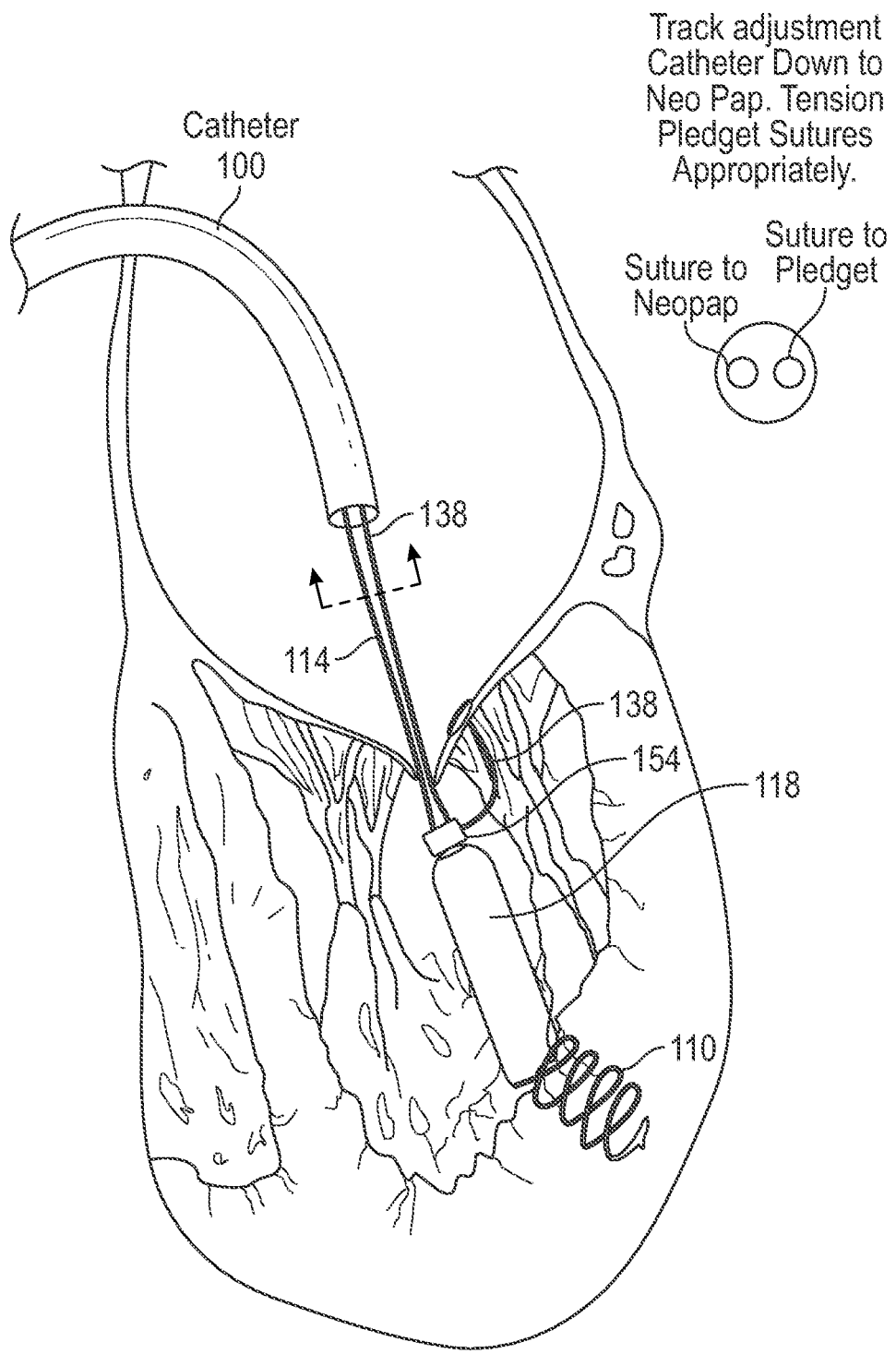
FIG. 35K schematically illustrates a fulcrum positioned at about the proximal end of the neo papillary muscle.

Referring to FIG. 35K, a fulcrum 154 is positioned at about the distal end of the neo chord and proximal end of the neo papillary muscle. At least the leaflet suture 138 passes across the fulcrum, so that proximal retraction on the leaflet suture pulls the atrium direction limit of travel of the flail leaflet in the direction of the ventricle. The fulcrum 154 may be the edge of a distal opening of a lumen of an adjustment catheter which is advanced distally over the leaflet suture and potentially also the ventricle anchor suture. The fulcrum may alternatively comprise an eye or loop on the distal end of a fulcrum support such as a hypo tube or support wire. Alternatively, the fulcrum 154 may be on a suture lock, through which both of the anchor suture and leaflet suture may pass.

Prior to engaging the suture lock, The leaflet suture is slowly proximally retracted to progressively limit prolapse of the flail leaflet into the left atrium. Mitral regurgitation is observed on fluoro, and the leaflet suture is retracted until MR has been eliminated or sufficiently minimized.

Figure 35L:
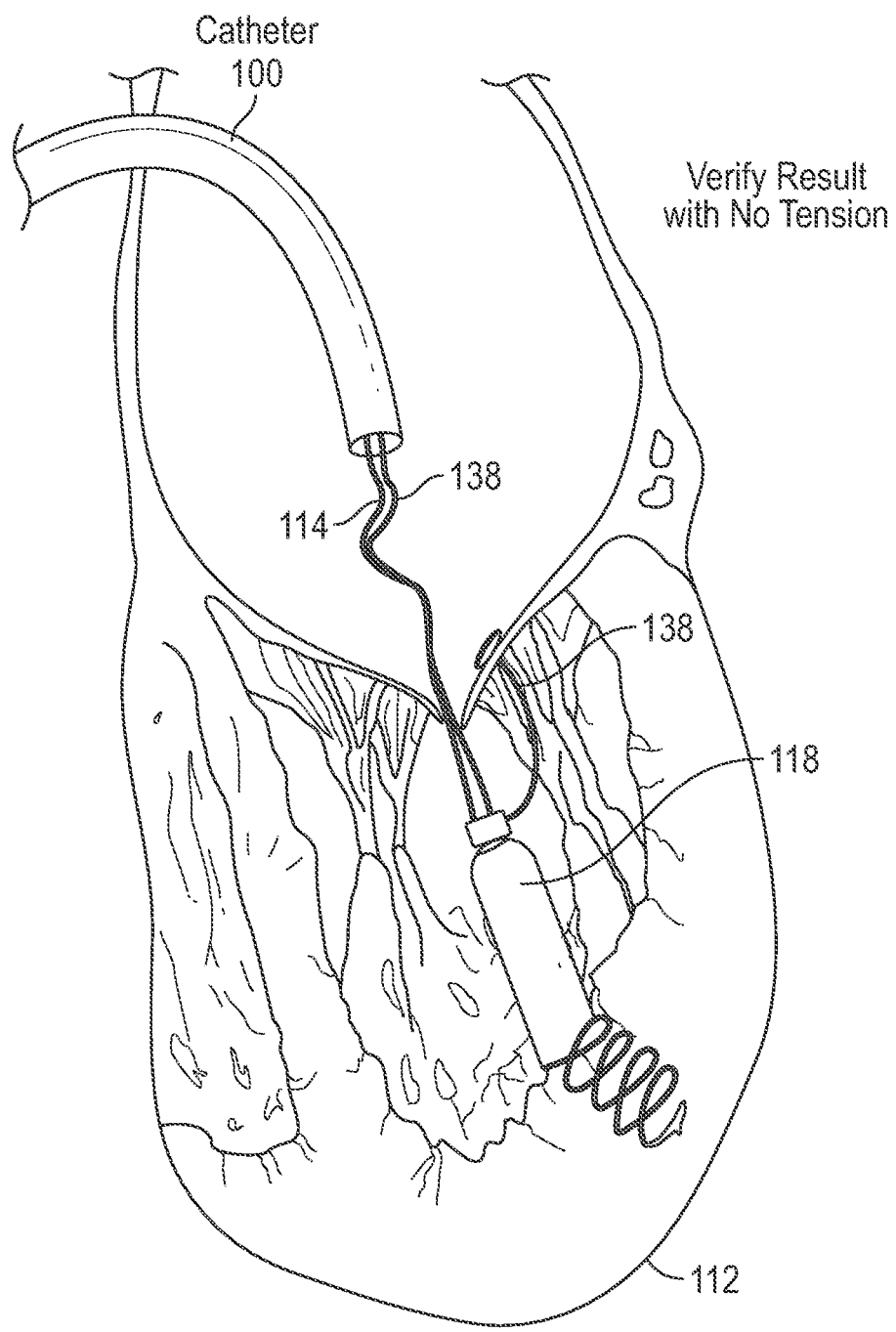
FIG. 35L illustrates verifying mitral valve function prior to removal of the deployment system.
Figure 35M:
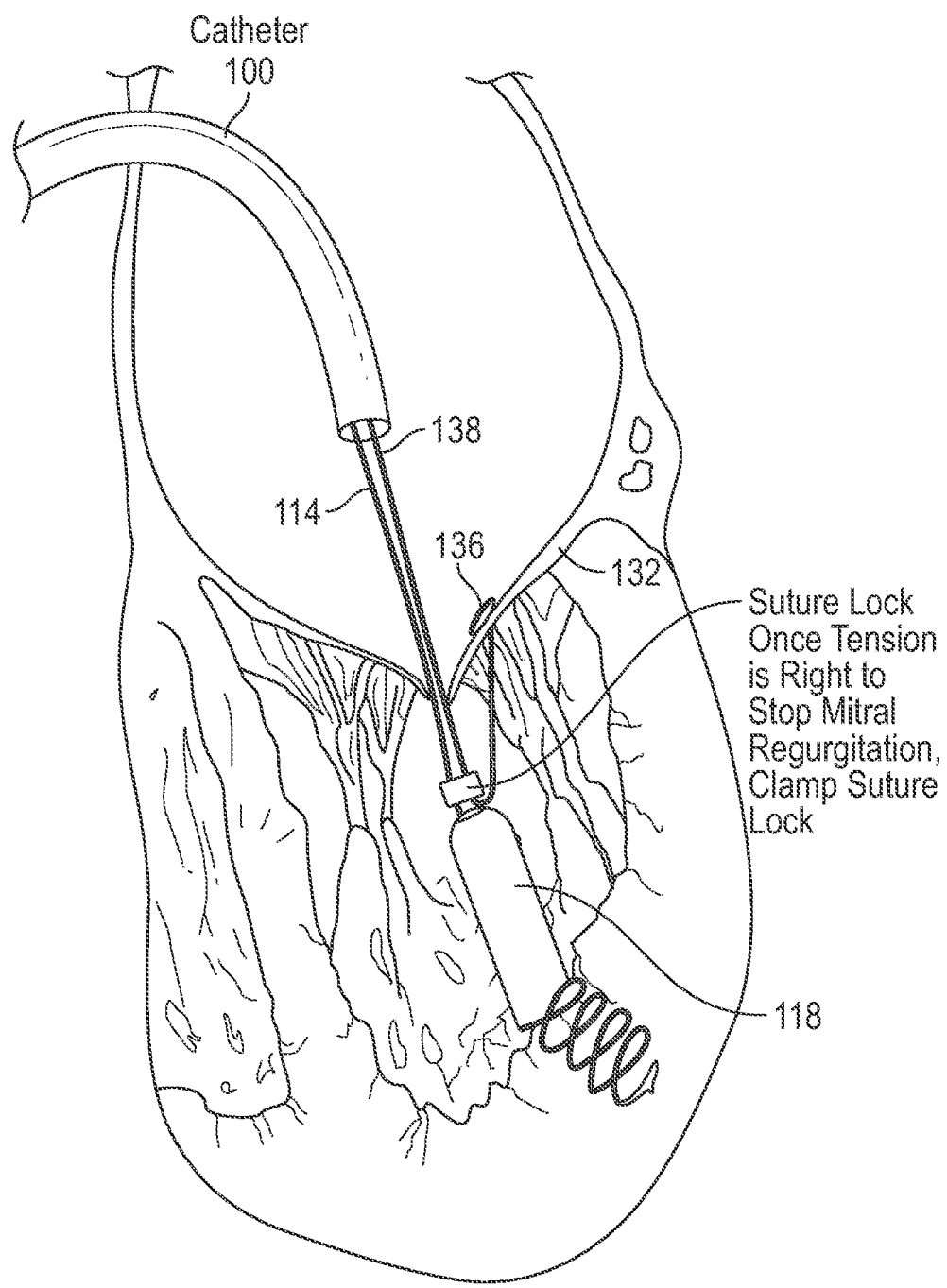
FIG. 35M illustrates the attachment of the leaflet suture to the ventricle suture following desired tensioning.
Figure 35N:
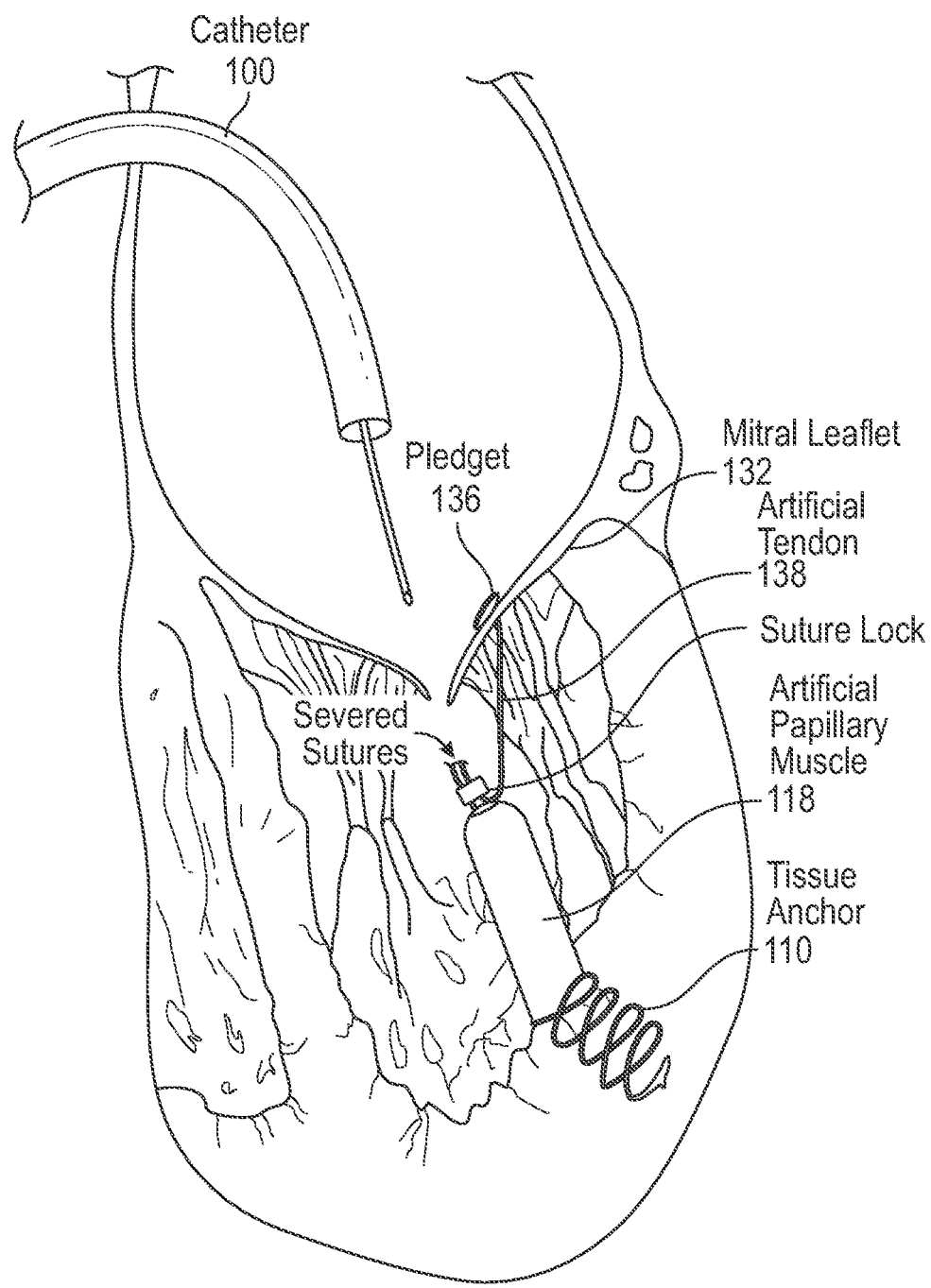
FIG. 35N illustrates severing of the leaflet suture and ventricle sutures, leaving the neo cord construct in place.
Figure 35O:
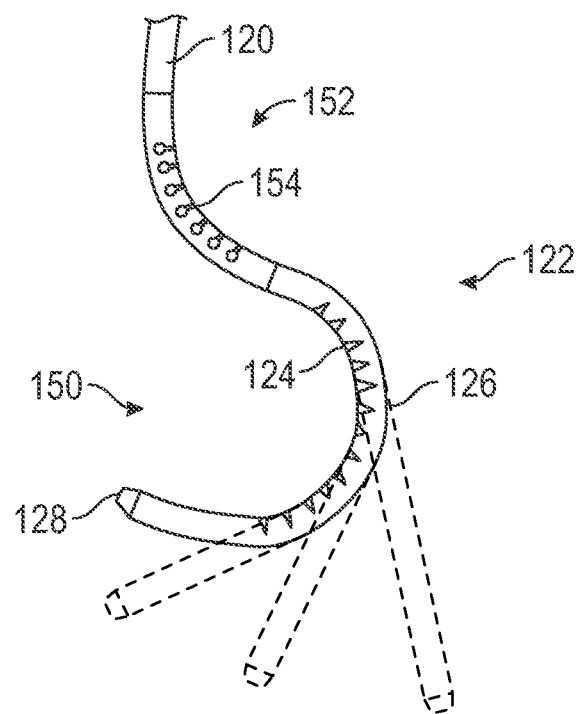
FIG. 35O illustrates a distal, steerable portion of a leaflet puncture catheter, having a compound deflected configuration.

Referring to FIG. 35L, the catheter 100 maybe advanced distally to induce slack in the anchor suture and leaflet suture, thereby minimizing any influence of the catheter 100 on leaflet function. This enables the physician to evaluate the effect on MR at the current tension level on the leaflet suture. The leaflet suture may be retracted or advanced to further adjust the leaflet range of travel, as desired.

Once the desired cardiac function has been achieved, the suture lock may be engaged, using known techniques, to fix the maximum distance between the tissue anchor 108 and the leaflet anchor. See FIG. 35 M. Alternatively, if the adjustment catheter was utilized as the fulcrum, a suture lock or knot may be advanced distally through the catheter into position in the vicinity of the distal end of the neo cord and the proximal end of the Neo papillary muscle, and secured.

Referring to FIG. 35 N, the leaflet suture 138 and anchor suture 114 proximally of the suture lock may be severed using down techniques, and the catheter 100 withdrawn from the patient. This leaves a neo cord and neo papillary muscle construct in place within the left ventricle.

Referring to FIG. 35 0, there is illustrated a distal deflection zone 122 on a modified leaflet capture catheter 120. As with the deflection zone illustrated in FIG. 35 C, the implementation of FIG. 35 0 includes a plurality of axially compressible slots 124 opposing a non-collapsible spine 126. Upon proximal retraction of a pull wire, this construct produces a primary concavity 150. As has been discussed, the shortest distance D at maximum flexion of the deflection zone 122 will generally be in the range of from about 0.5 to about 1.5 cm.

Depending upon the desired performance, there may be provided a secondary concavity 152 operable by axially collapsing the second plurality of slots 154. Flexion of the secondary concavity 152 may be accomplished by proximal retraction of a second pull wire. Alternatively, the primary concavity 150 and secondary concavity 152 may be simultaneously flexed by pulling a single pull wire.

In the illustrated embodiment, the secondary concavity 152 is concave in the same plane as, and in an opposite direction from the primary concavity 150. Alternatively, the second concavity 152 can be concave in the same direction as the primary concavity 150. In either configuration, the primary concavity may reside in a first plane, and the secondary concavity 152 may reside in a second plane rotationally offset from the first plane, depending upon the desired performance. Additional details of compound curvature catheter shafts can be seen in US patent publication 2014/0243877, the disclosure of which is hereby incorporated in its entirety herein by reference.

Figure 36A:
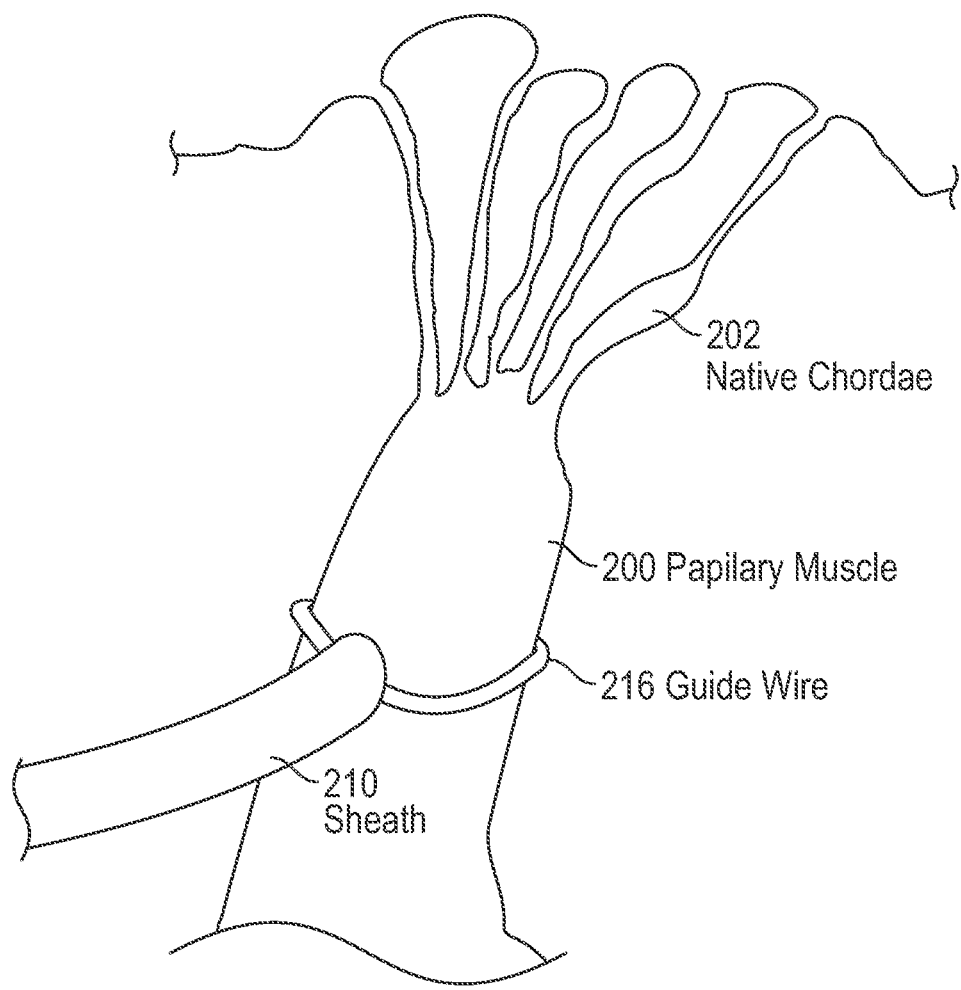
Figure 36B:
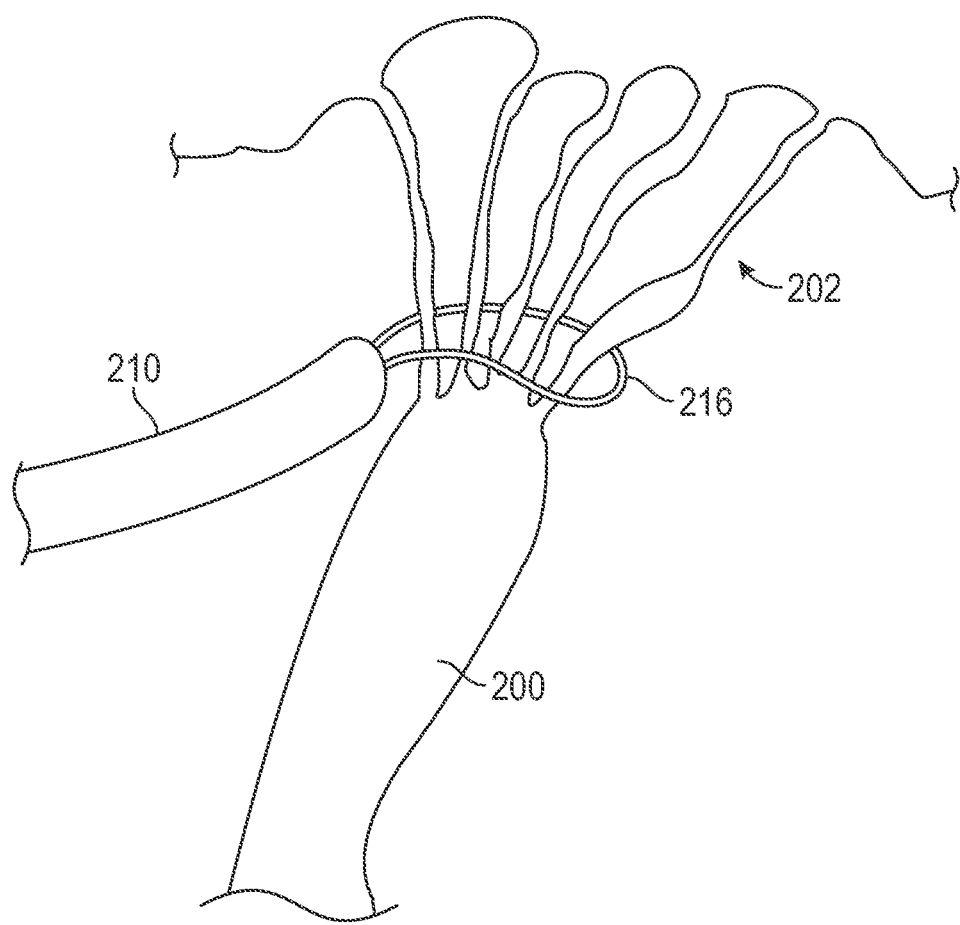
FIG. 36B shows the looped papillary pulled up onto the chords in an area where a cutting step is preferably performed.
Figure 37:
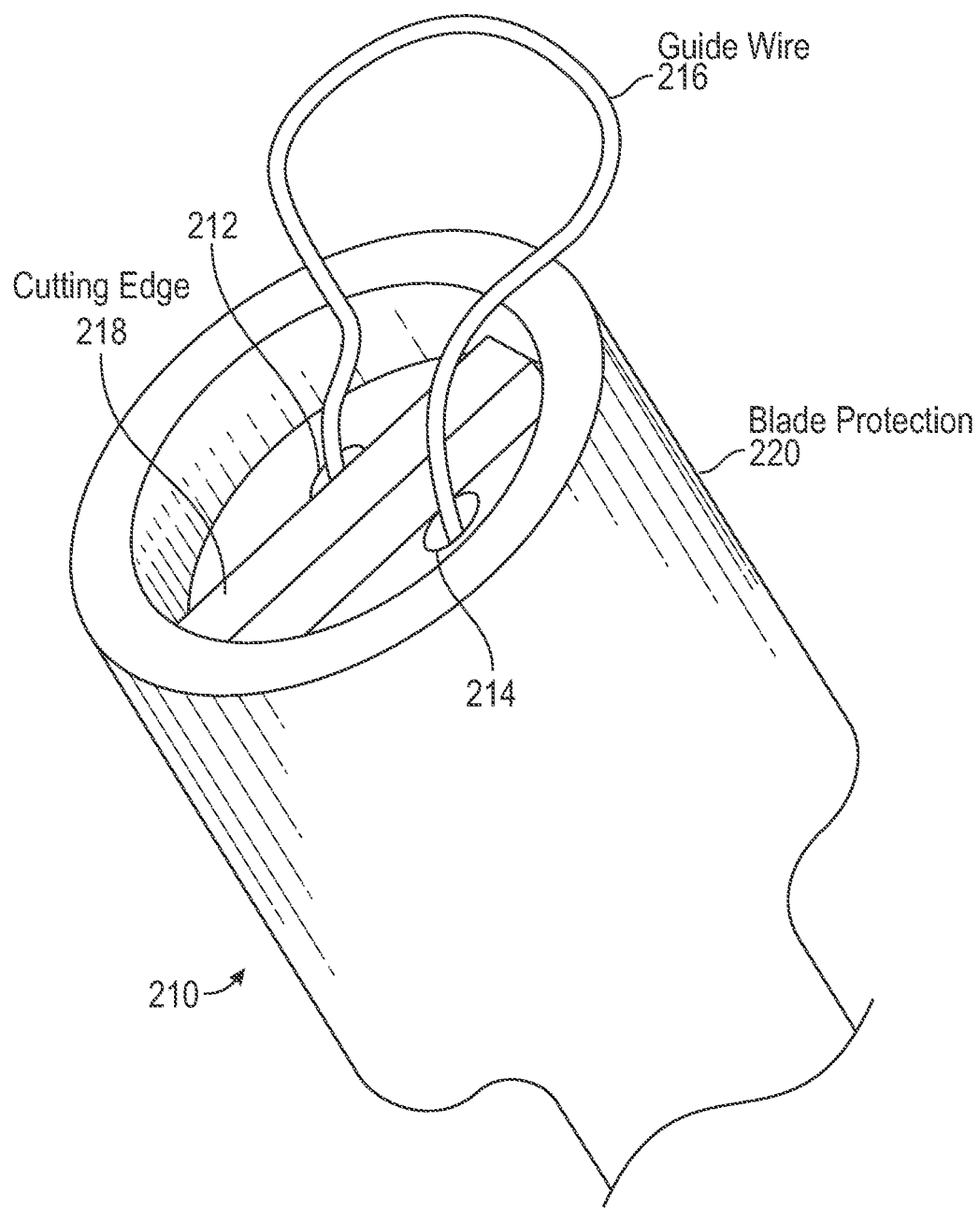
FIG. 37 illustrates one embodiment of a chordae cutting tool.

With reference now to FIGS. 36A-37, in some embodiments, rather than treating pure degenerative mitral regurgitation, embodiments of the method and devices disclosed here can also be used to treat a subset of patients with functional mitral regurgitation, where the patients have a leaflet tethered leaflet type of defect. In this anatomy, there is adequate length of the mitral valve leaflets for the leaflets to close and seal against leak, but the leaflets are not able to move up to the plane of the mitral annulus because the chordae are too short. This type of anatomy typically occurs because the annulus dilates and or the ventricle enlarges, while the chordae remain approximately the same length. Treatment of these patients can be performed by cutting all or a portion of the native chords as a step during the procedure.

In an embodiment, the chord cutting step is performed as the initial step, prior to the device implantation steps. This can prevent the possibility of accidental damage to the implant, but can create a condition of severe regurgirtation during the procedure. Alternatively, the native chords can be cut at any point during the implantation of prosthetic chords, or after the other steps of implantation of the prosthetic chords is complete. Cutting as a final step can create the disadvantage that it is not feasible to assess the exact result until after the chords have been implanted.

In certain embodiments, the native chordae are cut after placing the initial leaflet and ventricular anchors, but prior to final tensioning. In certain embodiments, this is achieved by first, prior to chord implantation, isolating the native chords by passing a guidewire around each papillary muscle, snaring the end of the wire and then advancing a sheath over the wire, in this way creating a snug loop around the papillary muscles. These loops can remain intact during the normal implantation of the ventricular and leaflet anchors. Once the ventricular and leaflet anchors are in place, using one of the devices and methods described here, and preferably partially tensioned, the native chords are cut. This can be achieved by manipulating the loops around the papillary muscles such that they move up past the papillary heads to the base of the chordae and cutting them. In one embodiment, the guidewire is simply pulled into the guide creating a cutting action. In another embodiment, a blade type tool that fits within the guide and has lumens for the guidewires is provided. By pulling both ends of the guidewire the chordae are pulled against the blade and cut. Many other tissue cutting devices have been described in the art and would be applicable to the devices and method described here. After the native chordae are cut the tension on the implant is adjusted. If the result is satisfactory it can be made permanent by locking and cutting as described in this application or by similar methods. If the result is not satisfactory additional chordae may be added or other mitral repair procedures may be performed in conjunction.

Looping the papillary muscle instead of looping the chordae directly ensures that all the chordae are captured, because all the normal chordae attach to the heads of the papillary muscles. Cutting using a looped guidewire is one method of cutting the native chordae but other methods and apparatuses can be used such as various types of transvascular suture cutters.

With reference now to FIGS. 36A-37, FIG. 36A is a picture of a looped papillary muscle 200 in the configuration it is first captured in. FIG. 36B shows the looped papillary 200 pulled up onto the chords 202 in the area where the cutting step is preferably performed. FIG. 37 illustrates one embodiment of the chordae cutting tool 210. The illustrated embodiment contains two lumens 212, 214, one for each end of a looped guidewire 216, a cutting edge 218 and an element 220 to protect the cutting edge 218 from contacting the sheath 210 and other portions of the device and patient that are not intended to be cut. As noted above, cutting using a looped guidewire is one method of cutting the native chordae but other methods and apparatuses can be used such as various types of transvascular suture cutters.

Although this disclosure describes certain embodiments and examples, many aspects of the above-described systems and methods may be combined differently and/or modified to form still further embodiments or acceptable examples. All such modifications and variations are intended to be included herein within the scope of this disclosure. Indeed, a wide variety of designs and approaches are possible and are within the scope of this disclosure.

Also, although there may be some embodiments within the scope of this disclosure that are not expressly recited above or elsewhere herein, this disclosure contemplates and includes all embodiments within the scope of what this disclosure shows and describes. Further, this disclosure contemplates and includes embodiments comprising any combination of any structure, material, step, or other feature disclosed anywhere herein with any other structure, material, step, or other feature disclosed anywhere herein.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

For purposes of this disclosure, certain aspects, advantages, and features are described herein. Not necessarily all such aspects, advantages, and features may be achieved in accordance with any particular embodiment. Those skilled in the art will recognize that the disclosure may be embodied or carried out in a manner that achieves one advantage or a group of advantages as taught herein without necessarily achieving other advantages as may be taught or suggested herein.

The disclosure herein of any particular feature, aspect, method, property, characteristic, quality, attribute, element, or the like in connection with various embodiments can be used in all other embodiments set forth herein. Also, any methods described herein may be practiced using any device suitable for performing the recited steps.

Moreover, while components and operations may be depicted in the drawings or described in the specification in a particular arrangement or order, such components and operations need not be arranged and performed in the particular arrangement and order shown, nor in sequential order, nor include all of the components and operations, to achieve desirable results. Other components and operations that are not depicted or described can be incorporated in the embodiments and examples. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

In summary, various illustrative embodiments and examples are described herein. Although the systems and methods have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow as well as their full scope of equivalents.

What is claimed is:

1. A method of transvascular prosthetic chordae tendinae implantation, comprising:
advancing a catheter into a left atrium, through a mitral valve, and into a left ventricle;
deploying a ventricular anchor from the catheter and into a wall of the left ventricle, leaving a ventricular suture attached to the ventricular anchor and extending proximally through the catheter;
advancing a leaflet anchor into a mitral valve leaflet to secure the mitral valve leaflet to a leaflet suture, with the leaflet suture extending proximally through the catheter; and
securing the leaflet suture to the ventricular suture to limit a range of travel of the mitral valve leaflet in a direction of the left atrium,
wherein the ventricular suture is attached to the ventricular anchor through a ventricular tension element.

2. The method as in claim 1, wherein advancing the leaflet anchor comprises securing the leaflet anchor to the mitral valve leaflet within the range of travel of from about 3 mm to about 10 mm from a leaflet coaptive edge.

3. The method as in claim 1, wherein deploying the ventricular anchor comprises attaching the ventricular anchor to a ventricular septum.

4. The method as in claim 1, wherein deploying the ventricular anchor comprises advancing an anchor driver through the mitral valve, rotating the anchor driver to secure the ventricular anchor, and proximally retracting the anchor driver to expose the ventricular suture carried by the ventricular anchor.

5. The method as in claim 1, wherein securing the leaflet suture to the ventricular suture comprises applying a suture lock to the ventricular suture and the leaflet suture.

6. The method as in claim 1, further comprising applying tension to the leaflet suture prior to securing the leaflet suture to the ventricular suture, to improve leaflet function.

7. The method as in claim 6, comprising applying sufficient tension to the leaflet suture to pull a limit of leaflet travel during systole to approximately to a level of an annulus.

8. The method as in claim 1, wherein securing the leaflet suture to the ventricular suture comprises engaging a knot to secure the leaflet suture and the ventricular suture.

9. The method as in claim 8, additionally comprising a step of cutting the leaflet suture and the ventricular suture proximally of the knot, leaving the leaflet suture and the ventricular suture to function as a native chordae.

10. The method as in claim 1, additionally comprising identifying a mitral valve that is incompetent due to leaflet tethering and cutting at least a portion of a native chordae of the mitral valve.

11. The method as in claim 1, further comprising an initial step of identifying a patient including at least three characteristics selected from a group consisting of:

the patient has been diagnosed with primary or degenerative mitral regurgitation;
the patient has been diagnosed with secondary or functional Mitral Regurgitation;
the patient has been diagnosed with Mixomotous Mitral Regurgitation;
the patient has been diagnosed with a flail leaflet, ruptured chordae, or leaflet prolapse;
the patient has Mitral regurgitation grade 1 or more;
the patient has annular diameter from A2 leaflet to P2 leaflet at least 5 mm less than sum of length of P2+A2 leaflet;
the patient has annular diameter from A2 to P2 leaflet of at least 10 mm; and
the patient has an access vessel diameter of at least 2 mm.

12. The method as in claim 11, wherein the patient additionally has at least one characteristic selected from a group consisting of:

the patient has been evaluated by a heart team including at least one cardiac surgeon and determined not to be an appropriate candidate for conventional open surgical repair;
the patient has STS predicted operative mortality (STS Score) of 2 or greater;
the patient was offered and refused open surgical repair;
the patient is age between 18 and 90;
the patient will not accept blood transfusion;
the patient has had prior open chest surgery; and
the patient has an ejection fraction of at least 10 percent.

13. A method of transvascular prosthetic chordae tendinae implantation, comprising:

advancing a catheter into a left atrium, through a mitral valve, and into a left ventricle;
deploying a ventricular anchor from the catheter and into a wall of the left ventricle, leaving a ventricular suture attached to the ventricular anchor and extending proximally through the catheter;
advancing a leaflet anchor into a mitral valve leaflet to secure the mitral valve leaflet to a leaflet suture, with the leaflet suture extending proximally through the catheter; and
securing the leaflet suture to the ventricular suture to limit a range of travel of the mitral valve leaflet in a direction of the left atrium,
wherein the ventricular suture is attached to the ventricular anchor through a ventricular tension element,
wherein the ventricular tension element comprises ePTFE.

14. The method as in claim 13, wherein advancing the leaflet anchor into the mitral valve leaflet comprises securing the leaflet anchor to the mitral valve leaflet within the range of travel of from about 3 mm to about 10 mm from a leaflet coaptive edge.

15. The method as in claim 13, wherein deploying the ventricular anchor from the catheter and into the wall of the left ventricle comprises attaching the ventricular anchor to a ventricular septum.

16. The method as in claim 13, wherein securing the leaflet suture to the ventricular suture comprises applying a suture lock to the ventricular suture and the leaflet suture.

17. The method as in claim 13, further comprising applying tension to the leaflet suture prior to securing the leaflet suture to the ventricular suture, to improve leaflet function.

18. The method as in claim 13, comprising applying sufficient tension to the leaflet suture to pull a limit of leaflet travel during systole to approximately to a level of an annulus.

19. The method as in claim 13, wherein securing the leaflet suture to the ventricular suture comprises engaging a knot to secure the leaflet suture and the ventricular suture.

20. The method as in claim 19, additionally comprising a step of cutting the leaflet suture and the ventricular suture proximally of the knot, leaving the leaflet suture and the ventricular suture to function as a native chordae.

* * * * *